(12) United States Patent
Bryans et al.

(10) Patent No.: US 7,745,630 B2
(45) Date of Patent: *Jun. 29, 2010

(54) TRIAZOLYL PIPERIDINE ARGININE VASOPRESSIN RECEPTOR MODULATORS

(76) Inventors: Justin Stephen Bryans, Ramsgate Road, Sandwich, Kent (GB) CT13 9NJ; Patrick Stephen Johnson, Ramsgate Road, Sandwich, Kent (GB) CT13 9NJ; Lee Richard Roberts, Ramsgate Road, Sandwich, Kent (GB) CT13 9NJ; Thomas Ryckmans, Ramsgate Road, Sandwich, Kent (GB) CT13 9NJ ( * ) Notice: Subject to any disclaimer, the term of this patent is extended or adjusted under 35 U.S.C. 154(b) by 898 days.

This patent is subject to a terminal disclaimer.

(21) Appl. No.: 11/009,768

(22) Filed: Dec. 10, 2004

(65) Prior Publication Data

US 2005/0154024 A1 Jul. 14, 2005

Related U.S. Application Data

(60) Provisional application No. 60/539,509, filed on Jan. 27, 2004, provisional application No. 60/570,336, filed on May 12, 2004.

(30) Foreign Application Priority Data

| Dec. 22, 2003 | (GB) | 0329693.6 |
| Apr. 20, 2004 | (GB) | 0408789.6 |

(51) Int. Cl.
- *A61K 31/454* (2006.01)
- *C07D 401/04* (2006.01)
- *C07D 401/14* (2006.01)

(52) U.S. Cl. .......................... 546/210; 514/326
(58) Field of Classification Search ................ 546/193, 546/210; 514/326
See application file for complete search history.

(56) References Cited

U.S. PATENT DOCUMENTS

| 4,481,360 A | 11/1984 | Gall et al. |
| 2007/0219187 A1* | 9/2007 | Bessis et al. ............. 514/228.8 |

FOREIGN PATENT DOCUMENTS

| EP | 0335144 | 10/1989 |
| EP | 1293503 | 3/2003 |
| EP | 1 293 503 A | 9/2003 |
| WO | WO 01/58880 A | 8/2001 |
| WO | WO 0158880 | 8/2001 |
| WO | WO 01/87855 A | 11/2001 |
| WO | WO 02066149 | 8/2002 |
| WO | WO 02088108 | 11/2002 |
| WO | WO 03053437 | 7/2003 |
| WO | WO 03104207 | 12/2003 |
| WO | WO 2004021984 | 3/2004 |
| WO | WO 2004037809 | 5/2004 |
| WO | WO 2004074291 | 9/2004 |
| WO | WO 2005028452 | 3/2005 |

OTHER PUBLICATIONS

Dorwald F. A. Side Reactions in Organic Synthesis, 2005, Wiley: VCH, Weinheim p. IX of Preface p. 1-15.*
Matthews et. al. "Synthesis and Biological Evaluation of Novel Indoloazepine Derivatives as Non-peptide Vasopressin V2 Receptor Antagonists." Bioorganic & Medicinal Chemistry Letters 13 (2003) 753-756.*
Zhang et. al. "Synthesis and evaluation of spirobenzazepines as potent vasopressin receptor antagonists" Bioorganic & Medicinal Chemistry Letters 14 (2004) 2987-2989.*
Lemmens-Gruber et. al. "Drugs of the future: Review Vasopressin antagonists" Cellular and Molecular Life Sciences 63 (2006) 1766-1779.*
Stefan Schaefer and Peter Kolkhof "Failure is an option: learning from unsuccessful proof-of-concept trials" Drug Discovery Today, vol. 13, Nos. 21/22 Nov. 2008, pp. 913-916.*
Andres, et. al. "Pharmacological characterization of F-180: a selective human V1a vasopressin receptor agonist of high affinity" British Journal of Pharmacology (2002) 135, 1828 -1836.*
Francois Clemence, et al., "Synthèse et activité analgésique dans la série des triazoles-1,2,4": *European J. Med.—Chim. Ther.*, 1985-20, No. 3, pp. 257-266.
Kakefuda, Akio et al: "Discovery of 4,5-Dipnyl-1,2,4- triazole Derivatives as a Novel Class of Selective Antagonists for the Human VIA Receptor" Bioorganic & Medicinal Chemistry, 10(6), 1905-1912 CODEN: BMECEP; ISSN: 0968-0896, 2002, XP002281248 cited in the application table 1.
Kakefuda A et al: "Synthesis and pharmacological evaluation of 5-(4-biphenyl)-3-methyl-4 phenyl-1,2,4- triazole derivatives as a novel class of selective antagonists for the human vasopressinV1A receptor" Journal of Medicinal and Pharmaceutical Chemisty, Americal Chemical Society Easton, US, vol. 45. No. 12, 2002, pp. 2589-2598, XP002237488 cited in the application table 1.

(Continued)

*Primary Examiner*—Rita J Desai
*Assistant Examiner*—David K O'Dell
(74) *Attorney, Agent, or Firm*—Gregg C. Benson; John A. Wichtowski

(57) ABSTRACT

Compounds of formula (I),

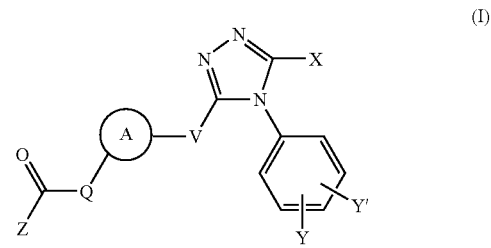

or pharmaceutically acceptable derivatives thereof, wherein: Z, O, A, V, Y and Y' are as defined herein; are useful for treating dysmenorreah.

15 Claims, No Drawings

OTHER PUBLICATIONS

Clemence F. et al. "Synthese at active analgesique dans la serie des triazoles 1,2,4", European Journal of Medicinal Chemistry, vol. 20, No. 3, 1985, pp. 257-266.

Kakefuda, A. et al., Discovery of 4,5-Diphenyl-1,2,4-triazole Derivatives as a Novel Class of Selective Antagonists for the Human $V_{1A}$ Receptor, Bioorganic & Medicinal Chemistry 10 (2002) 1905-1912.

Kakefuda, A. et al., Synthesis and Pharmacological Evaluation of 5-(4-Biphenyl)3-methyl-4-phenyl-1,2,4-triazole Derivatives as a Novel Class of Selective Antagonists for the Human Vasopressin $V_{1a}$ Receptor, J. Med. Chem. 2002, 45, 2589-2598.

WO 02/066149 takes the place of EP 1370349 which is the English equivalent to Chilean Applic. No. 237-2002.

WO 02/088108 takes the place of EP 1383759 which is the English equivalent to Chilean Applic. No. 897-2002.

WO 2004/021984 is the English equivalent of Chilean Applic. 1791-2003.

WO 2005/028452 is the equivalent to EP 1673355 which is the English equivalent to Chilean Applic. 2414-2004.

* cited by examiner

TRIAZOLYL PIPERIDINE ARGININE VASOPRESSIN RECEPTOR MODULATORS

This application claims priority to GB Application No. 0329693.6, filed Dec. 22, 2003, U.S. Provisional Application No. 60/539,509, filed Jan. 27, 2004, GB Application No. 0408789.6, filed Apr. 20, 2004, and U.S. Provisional Application No. 60/570,336, filed May 12, 2004.

This invention relates to triazole derivatives and to processes for the preparation of, intermediates used in the preparation of, compositions containing and the uses of, such derivatives.

The triazole derivatives of the present invention are vasopressin antagonists. In particular they are antagonists of the V1a receptor and have a number of therapeutic applications, particularly in the treatment of dysmenorrhoea (primary and secondary).

There is a high unmet need in the area of menstrual disorders and it is estimated that up to 90% of all menstruating women are affected to some degree. Up to 42% of women miss work or other activities due to menstrual pain and it has been estimated that around 600 million work hours a year are lost in the U.S. as a result {Coco, A. S. (1999). Primary dysmenorrhoea. [Review] [30 refs]. *American Family Physician*, 60, 489-96}.

Menstrual pain in the lower abdomen is caused by myometrial hyperactivity and reduced uterine blood flow. These pathophysiological changes result in abdominal pain that radiates out to the back and legs. This may result in women feeling nauseous, having headaches and suffering from insomnia. This condition is called dysmenorrhoea and can be classified as either primary or secondary dysmenorrhoea.

Primary dysmenorrhoea is diagnosed when no abnormality causing the condition is identified. This affects up to 50% of the female population {Coco, A. S. (1999). Primary dysmenorrhoea. [Review] [30 refs]. *American Family Physician*, 60, 489-96; Schroeder, B. & Sanfilippo, J. S. (1999). Dysmenorrhoea and pelvic pain in adolescents. [Review] [78 refs]. *Pediatric Clinics of North America*, 46, 555-71}. Where an underlying gynaecological disorder is present, such as endometriosis, pelvic inflammatory disease (PID), fibroids or cancers, secondary dysmenorrhoea will be diagnosed. Secondary dysmenorrhoea is diagnosed in only approximately 25% of women suffering from dysmenorrhoea. Dysmenorrhoea can occur in conjunction with menorrhagia, which accounts for around 12% of referrals to gynaecology outpatients departments.

Currently, women suffering from primary dysmenorrhoea are treated with non-steroidal anti-inflammatory drugs (NSAID's) or the oral contraceptive pill. In cases of secondary dysmenorrhoea surgery may be undertaken to correct the underlying gynaecological disorder.

Women suffering from dysmenorrhoea have circulating vasopressin levels which are greater than those observed in healthy women at the same time of the menstrual cycle. Inhibition of the pharmacological actions of vasopressin, at the uterine vasopressin receptor, may prevent dysmenorrhoea.

The compounds of the present invention are therefore potentially useful in the treatment of a wide range of disorders, particularly aggression, Alzheimer's disease, anorexia nervosa, anxiety, anxiety disorder, asthma, atherosclerosis, autism, cardiovascular disease (including angina, atherosclerosis, hypertension, heart failure, edema, hypernatremia), cataract, central nervous system disease, cerebrovascular ischemia, cirrhosis, cognitive disorder, Cushing's disease, depression, diabetes mellitus, dysmenorrhoea (primary and secondary), emesis (including motion sickness), endometriosis, gastrointestinal disease, glaucoma, gynaecological disease, heart disease, intrauterine growth retardation, inflammation (including rheumatoid arthritis), ischemia, ischemic heart disease, lung tumor, micturition disorder, mittlesmerchz, neoplasm, nephrotoxicity, non-insulin dependent diabetes, obesity, obsessive/compulsive disorder, ocular hypertension, preclampsia, premature ejaculation, premature (preterm) labour, pulmonary disease, Raynaud's disease, renal disease, renal failure, male or female sexual dysfunction, septic shock, sleep disorder, spinal cord injury, thrombosis, urogenital tract infection or urolithiasis.

Particularly of interest are the following diseases or disorders:

anxiety, cardiovascular disease (including angina, atherosclerosis, hypertension, heart failure, edema, hypernatremia), dysmenorrhoea (primary and secondary), endometriosis, emesis (including motion sickness), intrauterine growth retardation, inflammation (including rheumatoid arthritis), mittlesmerchz, preclampsia, premature ejaculation, premature (preterm) labour and Raynaud's disease.

The compounds of the invention, and their pharmaceutically acceptable salts and solvates, have the advantage that they are selective inhibitors of the V1a receptor (and so are likely to have reduced side effects), they may have a more rapid onset of action, they may be more potent, they may be longer acting, they may have greater bioavailability or they my have other more desirable properties than the compounds of the prior art.

According to the present invention there is provided a compound of formula (I),

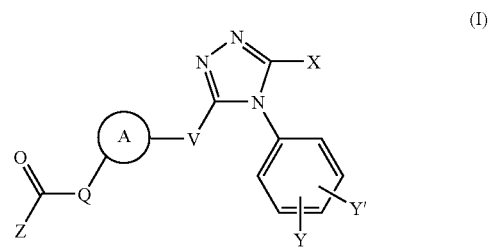

or a pharmaceutically acceptable derivative thereof, wherein:

X represents —[CH$_2$]$_a$—R or —[CH$_2$]$_a$—O—[CH$_2$]$_b$—R;
   a represents a number selected from 0 to 6;
   b represents a number selected from 0 to 6;
   R represents H, CF$_3$ or Het;
      Het represents a 5- or 6-membered saturated, partially saturated or aromatic heterocyclic ring comprising either (a) 1 to 4 nitrogen atoms, (b) 1 oxygen atom or 1 sulphur atom, or (c) 1 oxygen atom or 1 sulphur atom and 1 or 2 nitrogen atoms, optionally substituted with one or more groups independently selected from W;

Y represents one or more substituents independently selected from —[O]$_c$—[CH$_2$]$_d$—R$^1$, which may be the same or different at each occurrence;
   c at each occurrence independently represents a number selected from 0 or 1;
   d at each occurrence independently represents a number selected from 0 to 6;
   R$^1$ at each occurrence independently represents H, halo, CF$_3$, CN or Het$^1$;

Het¹ at each occurrence independently represents a 5- or 6-membered unsaturated heterocyclic ring, comprising either (a) 1 to 4 nitrogen atoms, (b) 1 oxygen atom or 1 sulphur atom, or (c) 1 oxygen atom or 1 sulphur atom and 1 or 2 nitrogen atoms;

V represents a direct link or —O—;

Ring A represents a 5- to 7-membered saturated heterocyclic ring comprising either (a) 1 to 4 nitrogen atoms, (b) 1 oxygen atom or 1 sulphur atom, or (c) 1 oxygen atom or 1 sulphur atom and 1 or 2 nitrogen atoms, or it represents a phenylene group; ring A being optionally substituted with one or more groups selected from $C_{1-6}$ alkyl, phenyl or hydroxy;

Q represents a direct link or —N($R^2$)—;
  $R^2$ represents hydrogen or $C_{1-6}$ alkyl;

Z represents —[O]$_e$—[CH$_2$]$_f$—$R^3$, a phenyl ring (optionally fused to a benzene ring or Het², and the group as a whole being optionally substituted with one or more groups independently selected from W), or Het³ (optionally fused to an benzene ring or Het⁴, and the group as a whole being optionally substituted with one or more groups independently selected from W);
  $R^3$ represents $C_{1-6}$ alkyl (optionally substituted with one or more groups independently selected from W), $C_{3-6}$ cycloalkyl, $C_{3-6}$ cycloalkenyl, phenyl (optionally substituted with one or more groups independently selected from W), Het⁵ or NR⁴R⁵;
  e represents a number selected from 0 or 1;
  f represents a number selected from 0 to 6;
  Het² and Het⁵ independently represent a 5- or 6-membered saturated, partially saturated or aromatic heterocyclic ring, comprising either (a) 1 to 4 nitrogen atoms, (b) 1 oxygen atom or 1 sulphur atom, or (c) 1 oxygen atom or 1 sulphur atom and 1 or 2 nitrogen atoms, optionally substituted with one or more groups selected from W;
  Het³ represents a 4 to 6-membered saturated, partially saturated or aromatic heterocyclic ring, comprising either (a) 1 to 4 nitrogen atoms, (b) 1 oxygen atom or 1 sulphur atom, or (c) 1 oxygen atom or 1 sulphur atom and 1 or 2 nitrogen atoms, optionally substituted with one or more groups selected from W;
  Het⁴ represents a 6-membered aromatic heterocyclic ring, comprising either (a) 1 to 4 nitrogen atoms, (b) 1 oxygen atom or 1 sulphur atom, or (c) 1 oxygen atom or 1 sulphur atom and 1 or 2 nitrogen atoms, optionally substituted with one or more groups selected from W;
  $R^4$ and $R^5$ independently represent hydrogen, $C_{1-6}$ alkyl, $C_{1-6}$ alkyloxy, $C_{3-8}$ cycloalkyl (optionally fused to $C_{3-8}$ cycloalkyl) or Het⁶;
  $R^4$ and $R^5$ being optionally independently substituted with one of more groups selected from $C_{1-6}$ alkyl, $C_{1-6}$ alkyloxy, $C_{3-8}$ cycloalkyl (optionally fused to $C_{3-8}$ cycloalkyl), or phenyl;
  Het⁶ represents a 5- or 6-membered saturated, partially saturated or aromatic heterocyclic ring, comprising either (a) 1 to 4 nitrogen atoms, (b) 1 oxygen atom or 1 sulphur atom, or (c) 1 oxygen atom or 1 sulphur atom and 1 or 2 nitrogen atoms, optionally substituted with one or more groups selected from W;

W independently at each occurrence represents halo, [O]$_g$R⁶, SO$_2$R⁶, SR⁶, SO$_2$NR⁶R⁷, [O]$_h$[CH$_2$]$_i$CF$_3$, [O]$_j$CHF$_2$, phenyl (optionally substituted with halo, $C_{1-6}$ alkyl or $C_{1-6}$ alkyloxy), CN, phenoxy (optionally substituted with halo), OH, benzyl, NR⁶R⁷, NCOR⁶, benzyloxy, oxo, CONHR⁶, NSO$_2$R⁶R⁷, COR⁶, $C_{1-6}$alkylene-NCOR⁷, Het⁷;

$R^6$ represents hydrogen, $C_{1-6}$alkyl, $C_{3-6}$cycloalkyl, $C_{3-6}$cycloalkenyl or $C_{1-6}$alkylene-O—$C_{1-6}$alkyl;
$R^7$ represents hydrogen or $C_{1-6}$alkyl;
i represents a number selected from 0 to 6;
h represents a number selected from 0 or 1;
g represents a number selected from 0 or 1;
j represents a number selected from 0 or 1;
Het⁷ represents a 5- or 6-membered saturated, partially saturated or aromatic heterocyclic ring, comprising either (a) 1 to 4 nitrogen atoms, (b) 1 oxygen atom or 1 sulphur atom, or (c) 1 oxygen atom or 1 sulphur atom and 1 or 2 nitrogen atoms, optionally substituted by $R^6$ and/or $R^7$ and/or an oxo group.

In an alternative embodiment there is provided a compound of formula (I'):

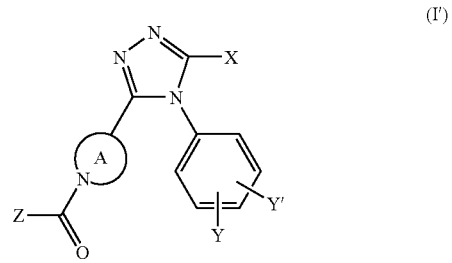

or a pharmaceutically acceptable derivative thereof, wherein:

X represents —[CH$_2$]$_a$—R or —[CH$_2$]$_a$—O—[CH$_2$]$_b$—R;
  a represents a number selected from 0 to 6;
  b represents a number selected from 0 to 6;
  R represents H, CF$_3$ or Het;
    Het represents a 5- or 6-membered heterocyclic ring comprising either (a) 1 to 4 nitrogen atoms, (b) 1 oxygen atom or 1 sulphur atom, or (c) 1 oxygen atom or 1 sulphur atom and 1 or 2 nitrogen atoms;

Y represents —[O]$_c$—[CH$_2$]$_d$—R¹;
Y' represents —[O]$_{c'}$—[CH$_2$]$_{d'}$—R¹';
  c and c' independently represent a number selected from 0 or 1;
  d and d' independently represent a number selected from 0 to 6;
  $R^1$ and $R^{1'}$ independently represent H, halo, CF$_3$ or Het¹;
    Het¹ represents a 5- or 6-membered unsaturated heterocyclic ring comprising either (a) 1 to 4 nitrogen atoms, (b) 1 oxygen atom or 1 sulphur atom, or (c) 1 oxygen atom or 1 sulphur atom and 1 or 2 nitrogen atoms;

Ring A represents a 5- or 6-membered saturated heterocyclic ring comprising at least one nitrogen atom;

Z represents —[O]$_e$—[CH$_2$]$_f$—$R^2$, a phenyl ring (optionally fused to a phenyl ring or a 5- or 6-membered saturated, partially unsaturated or aromatic heterocyclic ring, and/or optionally substituted with one or more groups independently selected from W), or a 6-membered aromatic heterocyclic ring (optionally fused to an phenyl ring or a 6-membered aromatic heterocyclic ring, and/or optionally substituted with one or more groups independently selected from W);
  $R^2$ represents $C_{1-6}$ alkyl or $C_{3-6}$ cycloalkyl;
  e represents a number selected from 0 or 1;
  f represents a number selected from 0 to 6;

W represents halo, [O]$_g$R³, SO$_2$R³, SR³, SO$_2$NR³R⁴, [O]$_h$[CH$_2$]$_i$CF$_3$, OCHF$_2$, phenyl, CN, phenoxy (optionally substituted with halo), OH, benzyl, NCOR³, benzyloxy, oxy, CONHR³, NSO₂R³R⁴, COR³, $C_{1-6}$alkylene-NCOR³, Het²;

R³ represents hydrogen, $C_{1-6}$alkyl, $C_{3-6}$cycloalkyl or $C_{1-6}$alkylene-O—$C_{1-6}$alkyl;

R⁴ represents hydrogen or $C_{1-6}$alkyl;

i represents a number selected from 0 to 6 h represents a number selected from 0 or 1;

g represents a number selected from 0 or 1;

Het² represents a 5- or 6-membered saturated, partially unsaturated or aromatic heterocyclic group comprising either (a) 1 to 4 nitrogen atoms, (b) 1 oxygen atom or 1 sulphur atom, or (c) 1 oxygen atom or 1 sulphur atom and 1 or 2 nitrogen atoms, the heterocyclic group being optionally substituted by R³ and/or R⁴ and/or an oxy group.

In the above definitions, halo means fluoro, chloro, bromo or iodo. Alkyl, alkylene and alkyloxy groups, containing the requisite number of carbon atoms, can be unbranched or branched. Examples of alkyl include methyl, ethyl, n-propyl, i-propyl, n-butyl, i-butyl, sec-butyl and t-butyl. Examples of alkyloxy include methoxy, ethoxy, n-propoxy, i-propoxy, n-butoxy, 1-butoxy, sec-butoxy and t-butoxy. Examples of alkylene include methylene, 1,1-ethylene, 1,2-ethylene, 1,1-propylene, 1,2-propylene, 1,3-propylene and 2,2-propylene. Het represents a heterocyclic group, examples of which include tetrahydrofuranyl, tetrahydrothiophenyl, pyrrolidinyl, tetrahydropyranyl, tetrahydrothiopyranyl, piperidinyl, 1,4-dioxanyl, 1,4-oxathianyl, morpholinyl, 1,4-dithianyl, piperazinyl, 1,4-azathianyl, 3,4-dihydro-2H-pyranyl, 5,6-dihydro-2H-pyranyl, 2H-pyranyl, 1,2,3,4-tetrahydropyridinyl, 1,2,5,6-tetrahydropyridinyl, pyrrolyl, furanyl, thiophenyl, pyrazolyl, imidazolyl, isoxazolyl, oxazolyl, isothiazolyl, thiazolyl, 1,2,3-triazolyl, 1,3,4-triazolyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, tetrazolyl, pyridinyl, pyridazinyl, pyrimidinyl and pyrazinyl.

A preferred compound is one in which X represents $CH_2OCH_3$. More preferred is a compound in which X represents —$[CH_2]_aR$.

A preferred compound is one in which a represents a number selected from 0 to 5. More preferred is a compound in which a represents a number selected from 0 to 4. Still more preferred is a compound in which a represents a number selected from 0 to 3. Still more preferred is a compound in which a represents a number selected from 0 to 2. Most preferred is a compound in which a represents the number 1.

A preferred compound is one in which R represents H. A more preferred compound is one in which R represents Het. Stoll more preferred is a compound in which R represents triazolyl.

A preferred compound is one in which Y represents one or two substituents. A more preferred compound is one in which Y represents a single substituent.

A preferred compound is one in which Y represents halo. A more preferred compound is one in which Y represents chloro and/or fluoro.

A preferred compound is one in which V represents a direct link. A preferred compound is one in which Q is a direct link. A more preferred compound is one in which both V and Q represent a direct link.

A preferred compound is one in which Ring A contains 2 nitrogen atoms. A more preferred compound is one in which Ring A contains 1 nitrogen atom.

A preferred compound is one in which Ring A represents a 5-membered ring. A more preferred compound is one in which Ring A represents a 6-membered ring. A still more preferred compound is one in which Ring A represents piperidinylene.

A preferred compound is one in which Ring A is attached to V via a nitrogen atom. A more preferred compound is one in which Ring A is attached to Q via a nitrogen atom. A preferred compound is one in which Ring A is attached to both Q and V via a nitrogen atom.

A preferred compound is one in which Z represents Het³. Het³ may represent an optionally substituted group selected from indazolyl, indolyl, indenyl, pyrazolyl, piperidinyl, pyridinyl, pyrimidinyl, pyrrolyl, thiazolyl, benzothienyl, benzothiazolyl, quinolinyl, benzoxazinyl, isoxazolyl, imidazolyl, furyl, benzofuryl, cinnolinyl, morpholinyl, chromenyl, or derivatives thereof. A more preferred compound is one in which Z represents phenyl.

A preferred compound is one in which Z is mono or di substituted. A more preferred compound is one in which Z is mono substituted.

A preferred compound is one in which Z is substituted by tri-fluoromethyl. A more preferred compound is one in which Z is substituted by halo. A more preferred compound is one in which Z is substituted by chloro and/or fluoro.

Specific preferred compounds according to the invention are those listed in the Examples section below, and the pharmaceutically acceptable salts thereof. In particular:

(3-Chloro-phenyl)-{4-[4-(4-chloro-phenyl)-5-[1,2,3]triazol-2-ylmethyl-4H-[1,2,4]triazol-3-yl]-piperidin-1-yl}-methanone;

(4-Chloro-phenyl)-{4-[4-(4-chloro-phenyl)-5-[1,2,3]triazol-2-ylmethyl-4H-[1,2,4]triazol-3-yl]-piperidin-1-yl}-methanone;

(5-Chloro-2-fluoro-phenyl)-{4-[4-(4-chloro-phenyl)-5-[1,2,3]triazol-2-ylmethyl-4H-[1,2,4]triazol-3-yl]-piperidin-1-yl}-methanone;

{4-[4-(4-Chloro-phenyl)-5-[1,2,3]triazol-2-ylmethyl-4H-[1,2,4]triazol-3-yl]-piperidin-1-yl}-(3,5-difluoro-phenyl)-methanone;

{4-[4-(4-Chloro-phenyl)-5-[1,2,3]triazol-2-ylmethyl-4H-[1,2,4]triazol-3-yl]-piperidin-1-yl}-(3-fluoro-phenyl)-methanone;

{4-[4-(4-Chloro-phenyl)-5-[1,2,3]triazol-2-ylmethyl-4H-[1,2,4]triazol-3-yl]-piperidin-1-yl}-(2,3-difluoro-phenyl)-methanone;

(3-Chloro-2-fluoro-phenyl)-{4-[4-(4-chloro-phenyl)-5-[1,2,3]triazol-2-ylmethyl-4H-[1,2,4]triazol-3-yl]-piperidin-1-yl}-methanone;

(3-Chloro-4-fluoro-phenyl)-{4-[4-(4-chloro-phenyl)-5-[1,2,3]triazol-2-ylmethyl-4H-[1,2,4]triazol-3-yl]-piperidin-1-yl}-methanone;

{4-[4-(4-Chloro-phenyl)-5-[1,2,3]triazol-2-ylmethyl-4H-[1,2,4]triazol-3-yl]-piperidin-1-yl}-(4-trifluoromethyl-phenyl)-methanone;

{4-[4-(4-Chloro-phenyl)-5-[1,2,3]triazol-2-ylmethyl-4H-[1,2,4]triazol-3-yl]-piperidin-1-yl}-(3-trifluoromethyl-phenyl)-methanone;

{4-[4-(4-Chloro-phenyl)-5-[1,2,3]triazol-2-ylmethyl-4H-[1,2,4]triazol-3-yl]-piperidin-1-yl}-(2-trifluoromethyl-phenyl)-methanone;

(3-Chloro-5-fluoro-phenyl)-{4-[4-(4-chloro-phenyl)-5-[1,2,3]triazol-2-ylmethyl-4H-[1,2,4]triazol-3-yl]-piperidin-1-yl}-methanone;

{4-[4-(4-Chloro-phenyl)-5-[1,2,3]triazol-2-ylmethyl-4H-[1,2,4]triazol-3-yl]-piperidin-1-yl}-(4-difluoromethyl-phenyl)-methanone;

{4-[4-(4-Chloro-phenyl)-5-[1,2,3]triazol-2-ylmethyl-4H-[1,2,4]triazol-3-yl]-piperidin-1-yl}-(1H-indazol-3-yl)-methanone;

and pharmaceutically acceptable derivatives thereof.

Pharmaceutically acceptable derivatives of the compounds of formula (I) according to the invention include salts, solvates, complexes, polymorphs, prodrugs, stereoisomers, geometric isomers, tautomeric forms, and isotopic variations of compounds of formula (I). Preferably, pharmaceutically acceptable derivatives of compounds of formula (I) comprise salts, solvates, esters and amides of the compounds of formula (I). More preferably, pharmaceutically acceptable derivatives of compounds of formula (I) are salts and solvates.

The pharmaceutically acceptable salts of the compounds of formula (I) include the acid addition and base salts thereof.

Suitable acid addition salts are formed from acids which form non-toxic salts. Examples include the acetate, aspartate, benzoate, besylate, bicarbonate/carbonate, bisulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, D- and L-lactate, malate, maleate, malonate, mesylate, methylsulphate, naphthylate, 2-napsylate, nicotinate, nitrate, orotate, oxalate, palmitate, palmoate, phosphate, hydrogen phosphate, dihydrogen phosphate, saccharate, stearate, succinate, sulphate, D- and L-tartrate, tosylate and trifluoroacetate salts. A particularly suitable salt is the besylate derivative of the compounds of the present invention.

Suitable base salts are formed from bases, which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

For a review on suitable salts see Stahl and Wermuth, Handbook of Pharmaceutical Salts: Properties, Selection and Use, Wiley-VCH, Weinheim, Germany (2002).

A pharmaceutically acceptable salt of a compound of formula (I) may be readily prepared by mixing together solutions of the compound of formula (I) and the desired acid or base, as appropriate. The salt may precipitate from solution and be collected by filtration or may be recovered by evaporation of the solvent. The degree of ionisation in the salt may vary from completely ionised to almost non-ionised.

The compounds of the invention may exist in both unsolvated and solvated forms. The term "solvate" is used herein to describe a molecular complex comprising the compound of the invention and one or more pharmaceutically acceptable solvent molecules, for example, ethanol. The term "hydrate" is employed when said solvent is water.

Included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components what may be in stoichiometric or non-stoichiometric amounts. The resulting complexes may be ionised, partially ionised, or non-ionised. For a review of such complexes, see J Pharm Sci, 64 (8), 1269-1288 by Haleblian (August 1975).

Hereinafter all references to compounds of formula (I) and pharmaceutically acceptable derivatives include references to salts, solvates and complexes thereof and to solvates and complexes of salts thereof.

The compounds of the invention include compounds of formula (I) as hereinbefore defined, polymorphs, prodrugs, and isomers thereof (including optical, geometric and tautomeric isomers) as hereinafter defined and isotopically-labelled compounds of formula (I).

As stated, the invention includes all polymorphs of the compounds of formula (I) as hereinbefore defined.

Also within the scope of the invention are so-called "prodrugs" of the compounds of formula (I). Thus certain derivatives of compounds of formula (I) which may have little or no pharmacological activity themselves can, when administered into or onto the body, be converted into compounds of formula (I) having the desired activity, for example, hydrolytic cleavage. Such derivatives are referred to as "prodrugs". Further information on the use of prodrugs may be found in "Pro-drugs as Novel Delivery Systems, Vol. 14, ACS Symposium Series (T Higuchi and W Stella) and "Bioreversible Carriers in Drug Design", Pergamon Press, 1987 (ed. E B Roche, American Pharmaceutical Association).

Prodrugs in accordance with the invention can, for example, be produced by replacing appropriate functionalities present in the compounds of formula (I) with certain moieties know to those skilled in the art as "pro-moieties" as described, for example, in "Design of Prodrugs" by H Bundgaard (Elsevier, 1985).

Some examples of prodrugs in accordance with the invention include:
  (i) where the compound of formula (I) contains a carboxylic acid functionality (—COOH), an ester thereof, for example, replacement of the hydrogen with $C_{1-8}$ alkyl;
  (ii) where the compound of formula (I) contains an alcohol functionality (—OH), an ether thereof, for example, replacement of the hydrogen with $C_{1-6}$ alkanoyloxymethyl; and
  (iii) where the compound of formula (I) contains a primary or secondary amino functionality (—$NH_2$ or —NHR where R≠H), an amide thereof, for example, replacement of one or both hydrogens with $C_{1-10}$ alkanoyl.

Further examples of replacement groups in accordance with the foregoing examples and examples of other prodrug types may be found in the aforementioned references.

Finally, certain compounds of formula (I) may themselves act as prodrugs of other compounds of formula (I).

Also within the scope of the invention are the metabolites of the compounds of formula (I) when formed in vivo.

Compounds of formula (I) containing one or more asymmetric carbon atoms can exist as two or more stereoisomers. Where a compound of formula (I) contains an alkenyl or alkenylene group, geometric cis/trans (or Z/E) isomers are possible, and where the compound contains, for example, a keto or oxime group or an aromatic moiety, tautomeric isomerism ('tautomerism') may occur. It follows that a single compound may exhibit more than one type of isomerism.

Included within the scope of the present invention are all stereoisomers, geometric isomers and tautomeric forms of the compounds of formula (I), including compounds exhibiting more than one type of isomerism, and mixtures of one or more thereof. Also included are acid addition or base salts wherein the counter ion is optically active, for example, D-lactate or L-lysine, or racemic, for example, DL-tartrate or DL-arginine.

Cis/trans isomers may be separated by conventional techniques well known to those skilled in the art, for example, fractional crystallisation and chromatography.

Conventional techniques for the preparation/isolation of individual enantiomers include chiral synthesis from a suitable optically pure precursor or resolution of the racemate (or the racemate of a salt or derivative) using, for example, chiral HPLC.

Alternatively, the racemate (or racemic precursor) may be reacted with a suitable optically active compound, for example, an alcohol, or, in the case where the compounds of formula (I) contains an acidic or basic moiety, an acid or base such as tartaric acid or 1-phenylethylamine. The resulting diastereomeric mixture may be separated by chromatography and/or fractional crystallisation and one or both of the diastereomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture.

Stereoisomeric conglomerates may be separated by conventional techniques known to those skilled in the art—see, for example, "Stereochemistry of Organic Compounds" by E L Eliel (Wiley, New York, 1994).

The present invention also includes all pharmaceutically acceptable isotopic variations of a compound of the formula (I) one or more atoms is replaced by atoms having the same atomic number, but an atomic mass or mass number different from the atomic mass or mass number usually found in nature.

Examples of isotopes suitable for inclusion in the compounds of the invention include isotopes of hydrogen such as $^2$H and $^3$H, carbon such as $^{11}$C, $^{13}$C and $^{14}$C, nitrogen such as $^{13}$N and $^{15}$N, oxygen such as $^{15}$O, $^{17}$O and $^{18}$O, phosphorus such as $^{32}$P, sulphur such as $^{35}$S, fluorine such as $^{18}$F, iodine such as $^{123}$I and $^{125}$I, and chlorine such as $^{36}$Cl.

Certain isotopically-labelled compounds of formula (I), for example those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labelled compounds of formula (I) can generally be prepared by conventional techniques known to those skilled in the art or by processes analogous to those described in the accompanying Examples and Preparations using appropriate isotopically-labelled reagents in place of the non-labelled reagent previously employed.

Pharmaceutically acceptable solvates in accordance with the invention include those wherein the solvent of crystallisation may be isotopically substituted, e.g. $D_2O$, $d_6$-acetone and $d_6$-DMSO.

The compounds of the invention are useful in therapy. Therefore, a further aspect of the invention is the use of a compound of formula (I), or a pharmaceutically salt or solvate thereof, as a medicament.

The compounds of the invention show activity as V1a antagonists. In particular they are useful in the treatment of a number of conditions including aggression, Alzheimer's disease, anorexia nervosa, anxiety, anxiety disorder, asthma, atherosclerosis, autism, cardiovascular disease (including angina, atherosclerosis, hypertension, heart failure, edema, hypernatremia), cataract, central nervous system disease, cerebrovascular ischemia, cirrhosis, cognitive disorder, Cushing's disease, depression, diabetes mellitus, dysmenorrhoea (primary and secondary), emesis (including motion sickness), endometriosis, gastrointestinal disease, glaucoma, gynaecological disease, heart disease, intrauterine growth retardation, inflammation (including rheumatoid arthritis), ischemia, ischemic heart disease, lung tumor, micturition disorder, mittlesmerchz, neoplasm, nephrotoxicity, non-insulin dependent diabetes, obesity, obsessive/compulsive disorder, ocular hypertension, preclampsia, premature ejaculatino, premature (preterm) labor, pulmonary disease, Raynaud's disease, renal disease, renal failure, male or female sexual dysfunction, septic shock, sleep disorder, spinal cord injury, thrombosis, urogenital tract infection or urolithiasis sleep disorder, spinal cord injury, thrombosis, urogenital tract infection, urolithiasis. Particularly of interest is dysmenorrhoea (primary or secondary), more particularly, primary dysmenorrhoea.

Therefore, a further aspect of the invention is the method of treatment of a mammal, including a human being, to treat a disorder for which a V1a antagonist is indicated, comprising administering a therapeutically effective amount of a compound of formula (I), or a pharmaceutically acceptable salt or solvate thereof, to the mammal. In particular, the compounds of formula (I) are useful in treating anxiety, cardiovascular disease (including angina, atherosclerosis, hypertension, heart failure, edema, hypernatremia), dysmenorrhoea (primary and secondary), endometriosis, emesis (including motion sickness), intrauterine growth retardation, inflammation (including rheumatoid arthritis), mittlesmerchz, preclampsia, premature ejaculation, premature (preterm) labour or Raynaud's disease. Even more particularly, they are useful in treating dysmenorrhoea (primary or secondary).

A further aspect of the present invention is the use of a compound of formula (I), or a pharmaceutically acceptable salt or solvate thereof, in the manufacture of a medicament for the treatment of a disorder for which a V1a receptor antagonist is indicated.

All of the compounds of the formula (I) can be prepared by the procedures described in the general methods presented below or by the specific methods described in the Examples section and the Preparations section, or by routine modifications thereof. The present invention also encompasses any or one or more of these processes for preparing the compounds of formula (I), in addition to any novel intermediates used therein.

Unless otherwise provided herein:
WSCDI means 1-(3-dimethylaminopropyl)-3-ethylcarbodiimide hydrochloride, DCC means N,N'-dicyclohexylcarbodiimide, HOAT means 1-hydroxy-7-aza benzotriazole, and HOBT means 1-hydroxybenzotriazole hydrate;

PyBOP® means Benzotriazol-1-yloxytris(pyrrolidino) phosphoniumhexa fluoro phosphate, PyBrOP® means bromo-tris-pyrrolidino-phosphoniumhexafluoro phosphate, and HBTU means O-benzotriazol-1-yl-N,N,N', N'-tetramethyluronium hexafluoro phosphate;

mCPBA means meta-chloroperbenzoic acid, AcOH means acetic acid, HCl means hydrochloric acid, TFA means trifluoroacetic acid, and p-TSA means p-toluenesulphonic acid;

$Et_3N$ means triethylamine and NMM means N-methylmorpholine;

$K_2CO_3$ means potassium carbonate and KO-$^t$Bu mean potassium tert-butoxide;

NaOH, KOH and LiOH mean sodium, potassium and lithium hydroxide respectively;

Boc means tert-butoxycarbonyl and CBz means benzyloxycarbonyl;

PTFE means polytetrafluoroethane;

MeI means methyl iodide;

MeTosylate means methyl p-toluenesulphonate;

MeOH means methanol, EtOH means ethanol and n-BuOH means n-butyl alcohol;

EtOAc means ethyl acetate, MeCN means acetonitrile, THF means tetrahydrofuran, DMSO means dimethyl sulphoxide, DCM means dichloromethane, DMF means N,N-dimethylformamide, NMP means N-methyl-2-pyrrolidinone, and DMA means dimethylacetamide;

Me means methyl, Et means ethyl, Cl means chloro, and OH means hydroxy;

cat means catalyst or catalytic.

In the following general methods, R, $R^1$, $R^2$, $R^3$, ring A, V, X, Q, Z, Y, Y', Het, $Het^1$, and $Het^2$ are as previously defined for a compound of the formula (I) unless otherwise stated. When Q represents $NR^2$, or Q represents a direct link attached to a nitrogen atom within ring A, then compounds of formula (I) may be prepared according to Scheme 1.

1.5-2.0 eq. of acetal (e.g. N,N-dimethylacetamide dimethyl acetal, triethyl orthopropionate), in THF or DMF at room temperature to 60° C. for about 18 hours, followed by p-TSA, or TFA (cat), in toluene at reflux for 18 hours.

Step (b): Formation of triazole (IV) may be achieved by reaction of compound (III) with a suitable aniline, in the presence of a suitable acid catalyst, such as TFA or p-TSA, in a suitable high boiling solvent (e.g. toluene, or xylene), at an elevated temperature. Preferred conditions: 0.5-1.0 eq. TFA, 1.0-2.0 eq. aniline in toluene at about reflux temperature for up to 18 hours.

Step (c): Deprotection of compound (IV) is undertaken using standard methodology, as described in "Protecting Groups in Organic Synthesis" by T. W. Greene and P. Wutz. When PG represents BOC, the preferred conditions are: 4M HCl in dioxan in MeOH, dioxan or DCM at between room temperature and about 50° C., for up to 18 hours;

Or, 2.2M HCl in MeOH for up to 18 hours at room temperature;

Or, TFA in DCM at room temperature for about 1 hour.

Alternatively, when PG represents BOC, compound (V) may be prepared directly from compound (III) by treatment

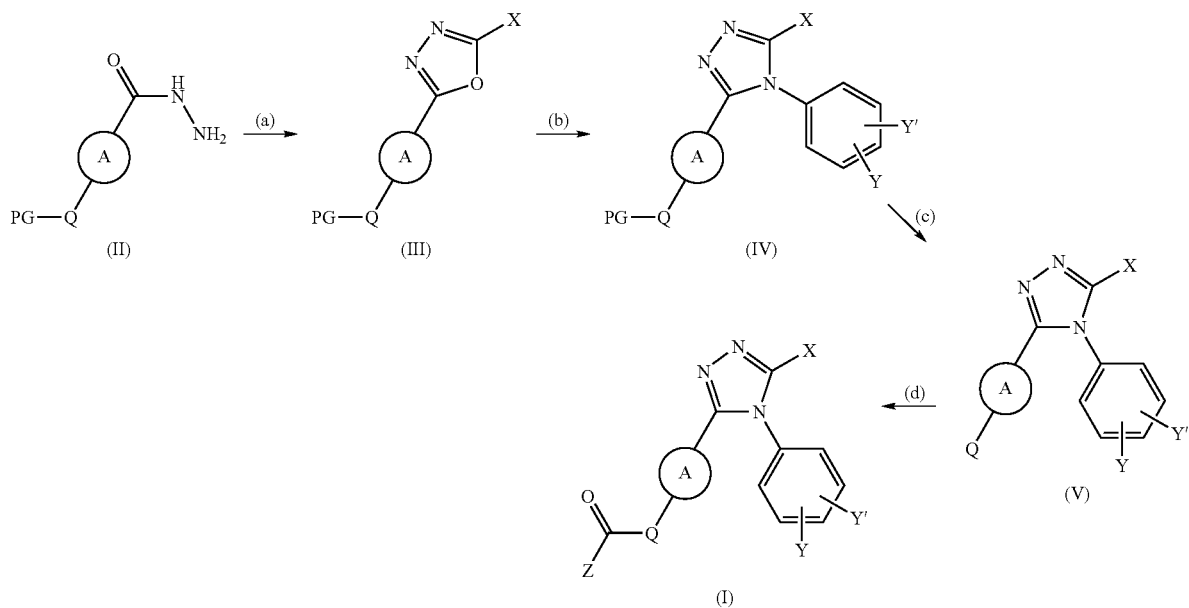

Scheme 1

PG represents a suitable N protecting group, typically a benzyl, BOC or CBz group, and preferably BOC Compounds of formula (II) may be obtained as described in WO 9703986 A1 19970206, or by reaction of the corresponding lower alkyl ester (e.g. methyl or ethyl) with hydrazine under standard conditions, as exemplified in the preparations below.

Step (a): Compounds of formula (III) may be prepared by reaction of hydrazine (II) with a suitable acetal (e.g. N,N-dimethylacetamide dimethyl acetal) in a suitable solvent such as THF, or DMF, at between room temperature and about 60° C., for up to 18 hours. The resulting intermediate may then be treated under acid catalysis (e.g. p-TSA, or TFA) in a high boiling solvent (e.g. toluene, or xylene) for about 18 hours, to provide the compound of formula (III). Preferred conditions:

with an excess of TFA, typically 1.1-1.5 eq.) and the appropriate aniline in toluene, at the reflux temperature of the reaction, for up to 4 days.

Step (d): Compounds of formula (I) may be prepared by reaction of amine (V) with a suitable acid or acid chloride

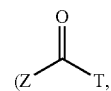

where T represents OH or Cl). The coupling may be undertaken by using either:
(i) an acyl chloride,

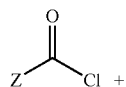

amine (V), with an excess of acid base in a suitable solvent; or
(ii) an acid $ZCO_2H$ with a conventional coupling agent+ amine (V) optionally in the presence of a catalyst, with an excess of base in a suitable solvent.

Typically the conditions are as follows:
(i) acid chloride

amine (V) (optionally with an excess of 3° amine such as $Et_3N$, Hünig's base or NMM) in DCM or THF, without heating, for 1 to 24 hours; or (ii) acid $ZCO_2H$, WSCDI/DCC and HOBT/HOAT, amine, an excess of NMM, $Et_3N$, or Hünig's base, in THF, DCM, DMA or EtOAc, at room temperature for 4 to 48 hours; or acid $ZCO_2H$, PYBOP®/PyBrOP®/O-benzotriazol-1-yl-N,N, N',N'-tetra methyl uronium hexafluorophosphate, excess amine, excess of NMM, $Et_3N$, or Hünig's base, in THF, DCM, DMA or EtOAc, at room temperature for 4 to 24 hours.

Preferred conditions are:
1 eq. amine (V), 1.0-1.5 eq.

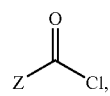

1.5-5 eq. NMM, $Et_3N$ or Hünig's base in DCM at room temperature for up to 18 hours;

Or, 1 eq. amine (V), 1.2 eq. $ZCO_2H$, 1.2-1.5 eq. HOBT, 1.2-1.5 eq. WSCDI, 2-4 eq. $Et_3N$, in DCM at room temperature for 24 hours;

Or, 1 eq. amine (V), 1.2-1.5 eq. $ZCO_2H$, 1.2-2.0 eq. HBTU, 5 eq. $Et_3N$ or NMM in DMA or DCM, at between room temperature and 60° C. for up to 24 hours.

Compounds of formula (IV), wherein Q represents $NR^2$, or Q represents a direct link attached to a nitrogen atom within ring A which is in turn attached to the triazole ring through a nitrogen atom, may alternatively be prepared as described in Scheme 2 below, and are represented as (IVA).

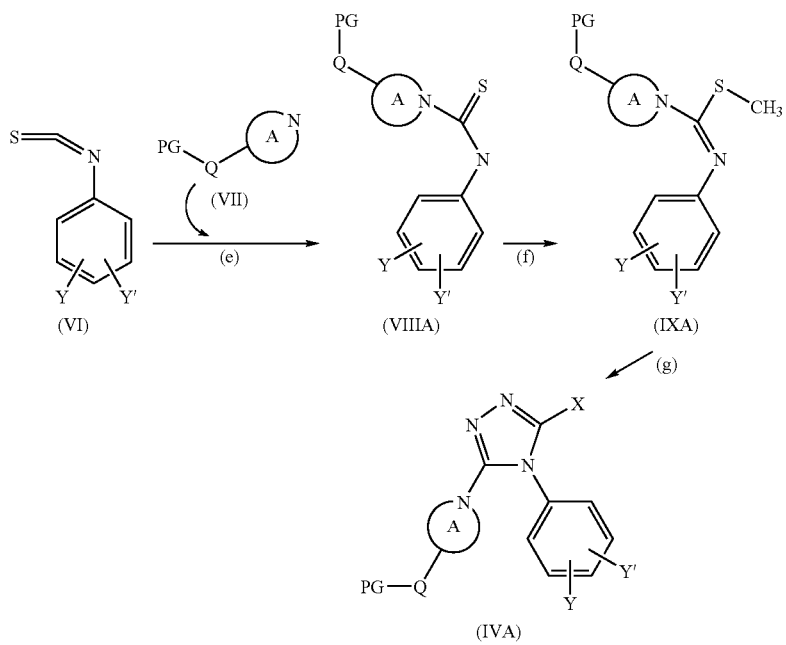

Scheme 2.

Step (e): Compounds of formula (VIIIA) may be prepared by reaction of approximately equimolar amounts of isothiocyanate (VI) and amine (VII), in a suitable solvent (e.g. EtOH, or DCM) at room temperature for between 2 and 72 hours. Preferred conditions: 1-1.1 eq. (VI), 1 eq. (VII), in EtOH or DCM, at room temperature for 0.5-2 hours.

Compounds of formulae (VI) and (VII) are commercially available, or may be prepared from known compounds using standard chemical transformations.

Step (f): Compounds of formula (IXA) may be prepared by methylation of thiourea (VIIIA), using a suitable methylating agent (e.g. MeI, or MeTosylate), in the presence of a suitable base (e.g. KO$^t$-Bu) in a suitable solvent (e.g. THF, or ether) at between 0° C. and the reflux temperature of the reaction, for about 18 hours. Preferred conditions: 1 eq. (VIIIA), 1-1.2 eq. KO$^t$-Bu, 1-1.2 eq. MeI or MeTosylate, in THF, at between 10° C. and room temperature for up to 18 hours.

Step (g): Compounds of formula (IVA) may be prepared by reaction of compounds (IXA) with a suitable hydrazide (XCONHNH$_2$), optionally under acidic catalysis (e.g. TFA, or p-TSA) in a suitable solvent (e.g. THF, or n-BuOH), at between room temperature and the reflux temperature of the reaction. Preferred conditions: 0.5 eq. TFA, excess hydrazide (XCONHNH$_2$), in THF at reflux for up to 18 hours.

Compounds of formula (VIIIA), wherein Q represents NR$^2$, or Q represents a direct link attached to a nitrogen atom within ring A, which in turn is attached to the triazole ring through a nitrogen atom, may alternatively be prepared as shown in Scheme 3.

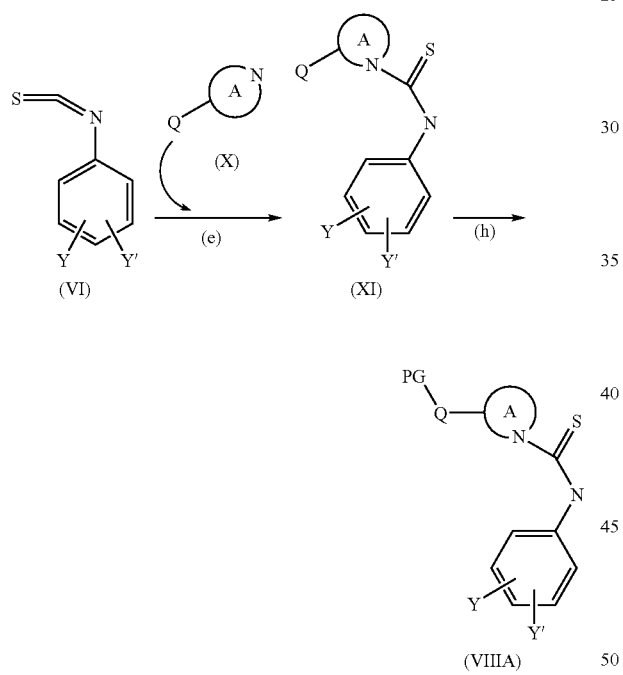

Compounds of formula (X) are commercially available, or may be prepared from known compounds using standard chemical transformations.

Compounds of formula (XI) may be prepared from isothiocyanate (VI) and amine (X), by analogy with the methods previously described for Step (e) above.

Step (h): Compounds of formula (VIIIA) may be obtained by protection of the reactive nitrogen atom, using standard methodology, as described in "Protecting Groups in Organic Synthesis" by T. W. Greene and P. Wutz. When PG is BOC, the preferred conditions are: 1 eq. amine (XI), 1 eq. di-t-butyl dicarbonate, in DCM and dioxan, at room temperature, for about 3 hours.

Compounds of formula (VIII), wherein Q represents NR$^2$, or Q represents a direct link attached to a nitrogen atom within ring A, which in turn is attached to the triazole ring through a carbon atom, may be prepared as described in Scheme 4, and are represented as (VIIIB).

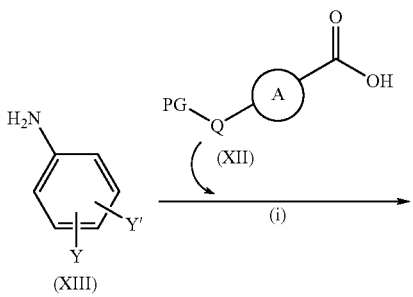

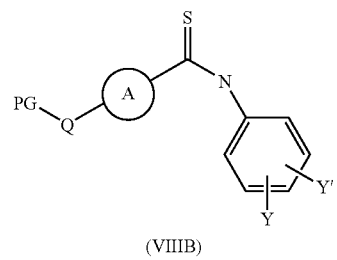

Step (i): Compounds of formula (XIV) may be prepared by coupling of aniline (XIII) with acid (XII), by analogy with the methods previously described in Step (d). Preferred conditions: 1 eq. acid (XII), 1.1 eq. amine (XIII), 1.2 eq. WSCDI, 3 eq. Et$_3$N in MeCN at room temperature, for about 3 days.

Step (j): The compound of formula (VIIIB) is prepared by thionation of compound (XIV) by treatment with a suitable thionating agent, such as Lawesson's reagent, in a high boiling solvent (e.g. toluene) at between room temperature and the reflux temperature of the reaction. Preferred conditions: 1 eq. (XIV), 0.5 eq. Lawesson's reagent in toluene, for between room temperature and reflux, for up to 18 hours.

Compounds of formula (III), wherein Q represents NR$^2$, or Q represents a direct link which is attached to a nitrogen atom within ring A, may alternatively be prepared as shown in Scheme 5.

Compounds of formula (III), wherein X represents CH$_2$N-linked-Het, may alternatively be prepared as shown in Scheme 6.

Scheme 5.

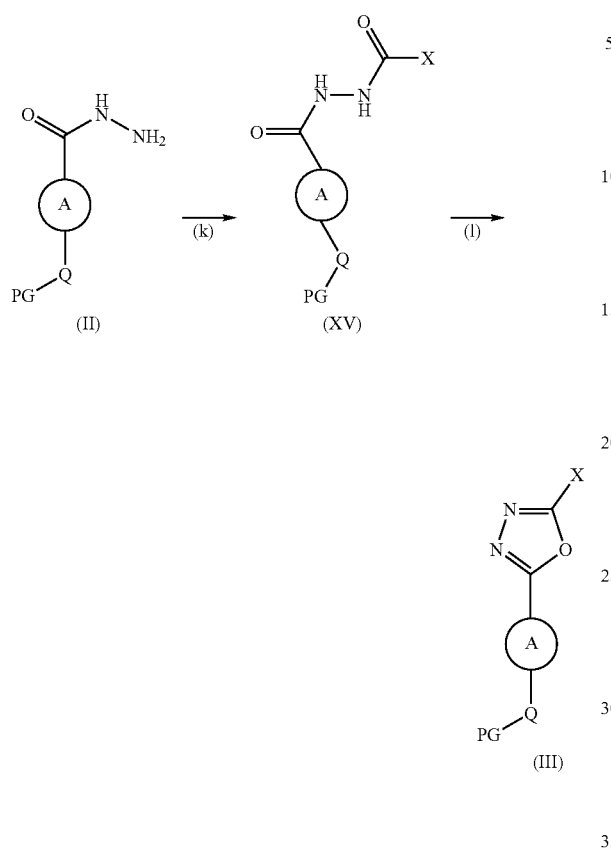

Scheme 6

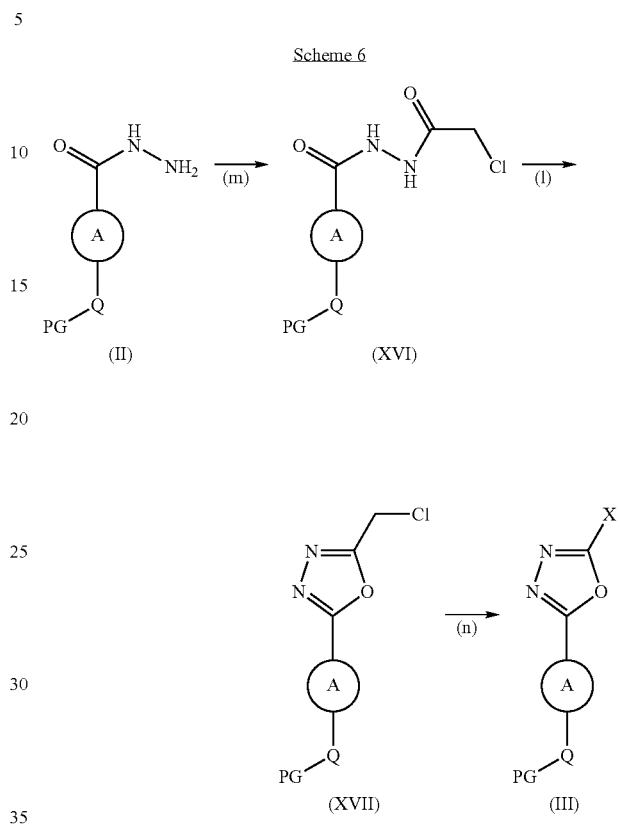

Step (k): Di-acylhydrazides (XV) may be prepared by coupling hydrazides (II) with acid or acid chloride

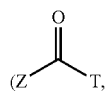

where T represents Cl or OH), by analogy with the methods previously described in Step (d). Preferred conditions: 1 eq. hydrazide (II), 1.1 eq. XCO$_2$H, 1.1 eq. WSCDI, 1.1 eq. HOBT, 1.2 eq. Et$_3$N, in DMF at room temperature for 18 hours.

Step (l): Oxadiazole (III) may be prepared by cyclisation of compound (XV), typically under acid catalysis (e.g. polyphosphoric acid, POCl$_3$, triflic anhydride/pyridine, or 1-methylimidazole), optionally in a suitable solvent (e.g. DCM), at between 0° C. and the reflux temperature of the reaction. Preferred conditions: 1 eq. (XV), excess pyridine or 1-methylimidazole, 1.5-2 eq triflic anhydride, in DCM, at between 0° C. and room temperature for up to 3 hours.

Compounds of formula (XV) may alternatively be prepared by coupling acid (XII) with a suitable hydrazide (XCONHNH$_2$), by analogy with the methods previously described in Step (d). Preferred conditions: 1 eq. acid (XII), 1 eq. hydrazide, 1.02 eq. WSDCI, in DCM at between 0° C. and room temperature.

Step (m): The compounds of formula (XVI) may be prepared by reaction of hydrazide (II) with chloroacetyl chloride, in the presence of a suitable 3° amine base (e.g. Et$_3$N, or NMM) in a suitable solvent (e.g. EtOAc, or DCM) at between 0° C. and room temperature, for about 18 hours. Preferred conditions: 1 eq. (II), 1 eq. acetyl chloride, 1.1 eq. NMM; in DCM, at 10° C. to room temperature, for up to 18 hours.

Compounds of formula (XVII) may be prepared by cyclisation compound (XVI), by analogy with the methods previously described in Step (I) above.

Step (n): Compounds of formula (III) may be prepared by reaction of compound (XVII) with a suitable Het (containing a reactive N atom), in the presence of a suitable base (e.g. Et$_3$N, or K$_2$CO$_3$), in a suitable solvent (e.g. DMF, or MeCN), at between room temperature and the reflux temperature of the reaction, for about 18 hours. Preferred conditions: 1 eq. (XVII), 1.4 eq. K$_2$CO$_3$, 2 eq. Het, in DMF at room temperature, for 18 hours.

Compounds of formula (I), wherein Q represents NR$^2$, or Q represents a direct link which is attached to a nitrogen atom within ring A, may alternatively be prepared as shown in Scheme 7.

Scheme 7

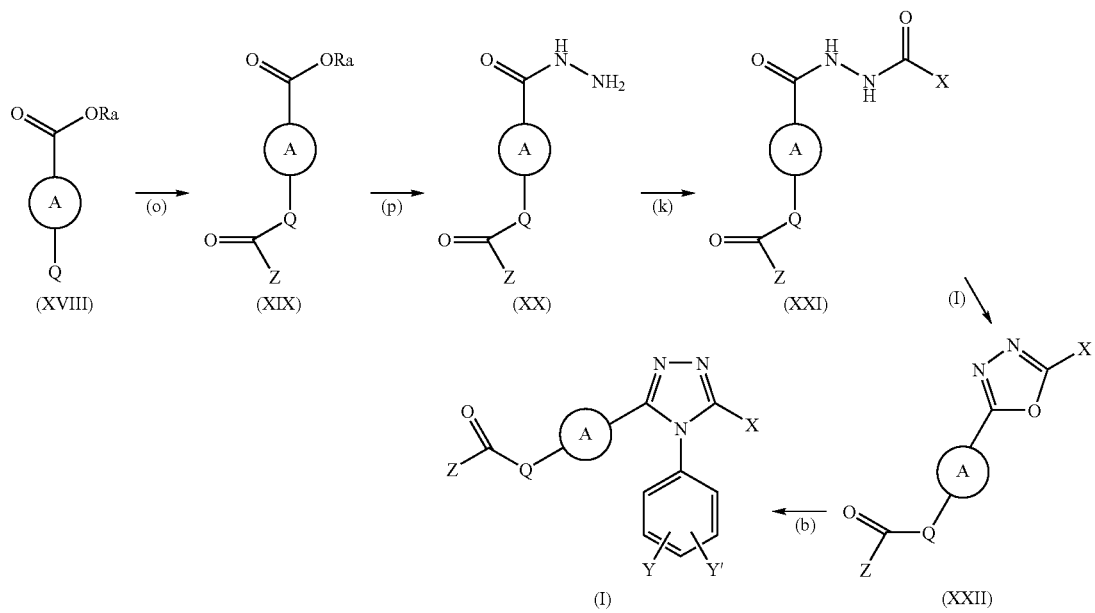

Ra represents $C_{1-4}$ alkyl or benzyl, and is preferably Me or Et.

Step (o): The compound of formula (XIX) may be prepared by reaction of amine (XVIII) with a suitable acid or acid chloride

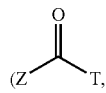

where T represents OH or Cl), by analogy with the methods previously described in Step (d). Preferred conditions: 1 eq. (XVIII), 0.9 eq. ZCOCl, 1.1 eq. $Et_3N$, in DCM, at between 10° C. and room temperature, for about 3 hours.

Step (p): The hydrazide of formula (XX) may be prepared by treating ester (XIX) with excess hydrazine in a suitable solvent (e.g. EtOH, or MeOH), at the reflux temperature of the reaction, for up to 18 hours. Preferred conditions: 1 eq. (XIX), 2-4 eq. hydrazine, in MeOH at reflux, for between 10 and 48 hours.

Compounds of formula (XXI) may be prepared by reaction of hydrazide (XX) with

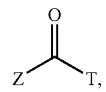

using the methods previously described in Step (k).

Compounds of formula (XXII) may be prepared by cyclisation of compound (XXI), using the methods previously described in Step (I).

Compounds of formula (I) may be prepared from oxadiazole (XXII) with a suitable aniline, as previously described in Step (b).

Alternatively, compounds of formula (XXII) may be prepared directly from compound (XX) by reaction with an appropriate acetal (e.g. triethyl orthopropionate, N,N-dimethylacetamide dimethyl acetal) by analogy with the methods previously described in Step (a).

Compounds of formula (XXII), wherein X represents $CH_2$—N-linked-Het, may alternatively be prepared as shown in Scheme 8.

Scheme 8

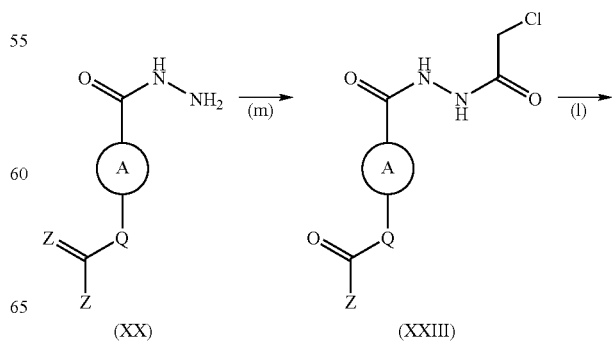

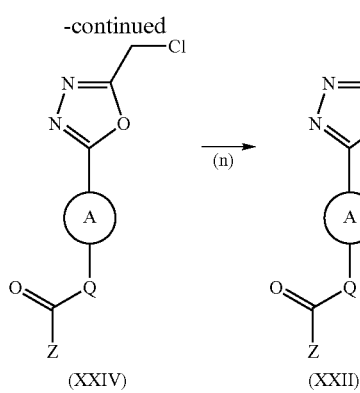

Compounds of formula (XXIII) may be prepared by reaction of hydrazide (XX) with chloroacetyl chloride, by analogy with the methods previously described in Step (m).

Oxadiazole (XXIV) may be prepared by cyclisation of compound (XXIII), by analogy with the methods previously described in Step (I).

Compound (XXII) may be prepared by reaction of compound (XXIV) with a suitable Het (containing a reactive N atom), as previously described in Step (n).

Compounds of formula (I), wherein ring A is attached to the triazole ring through a nitrogen atom, may alternatively be prepared as shown in Scheme 9.

Scheme 9

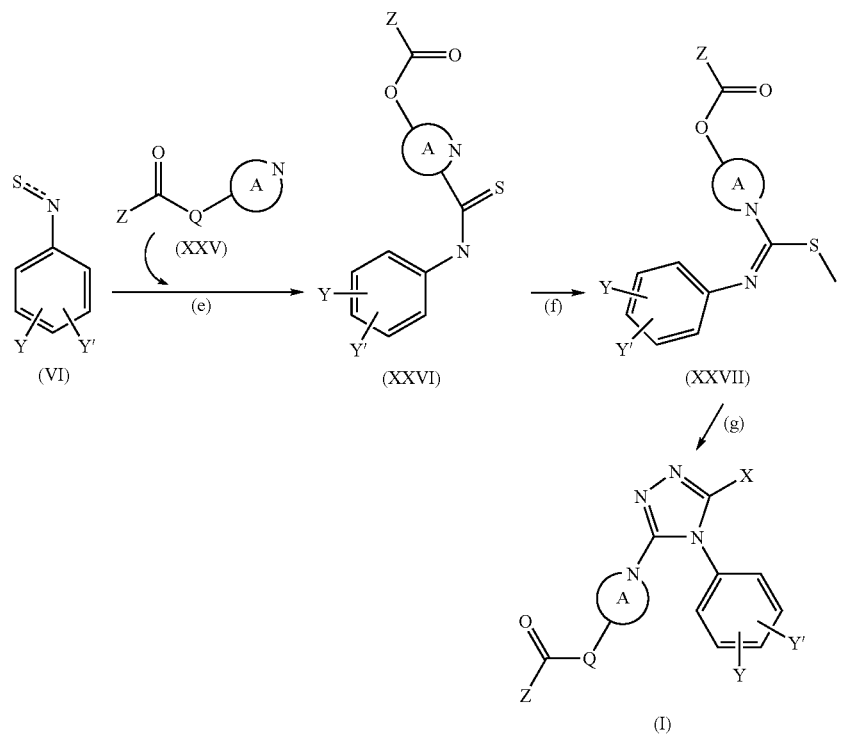

Compounds of formula (XXV) are either commercially available or may be prepared from commercially available compounds, using standard chemical transformations.

Compounds of formula (XXVI) may be prepared by reaction of compound (XXV) with the appropriate isothiocyanate (VI), by analogy with the methods previously described in Step (e).

The compound of formula (XXVII) may be prepared by alkylation of compound (XXVI), by analogy with the methods previously described in Step (f).

The compound of formula (I) may be prepared by reaction of compound (XXVII) with a suitable hydrazide, as previously described in Step (g).

Compounds of formula (I), wherein Q represents a direct link which is attached to a carbon atom in ring A, which in turn is attached to the triazole ring via a nitrogen atom in ring A, and Z represents $NR^4R^5$, may be prepared as shown in Scheme 10.

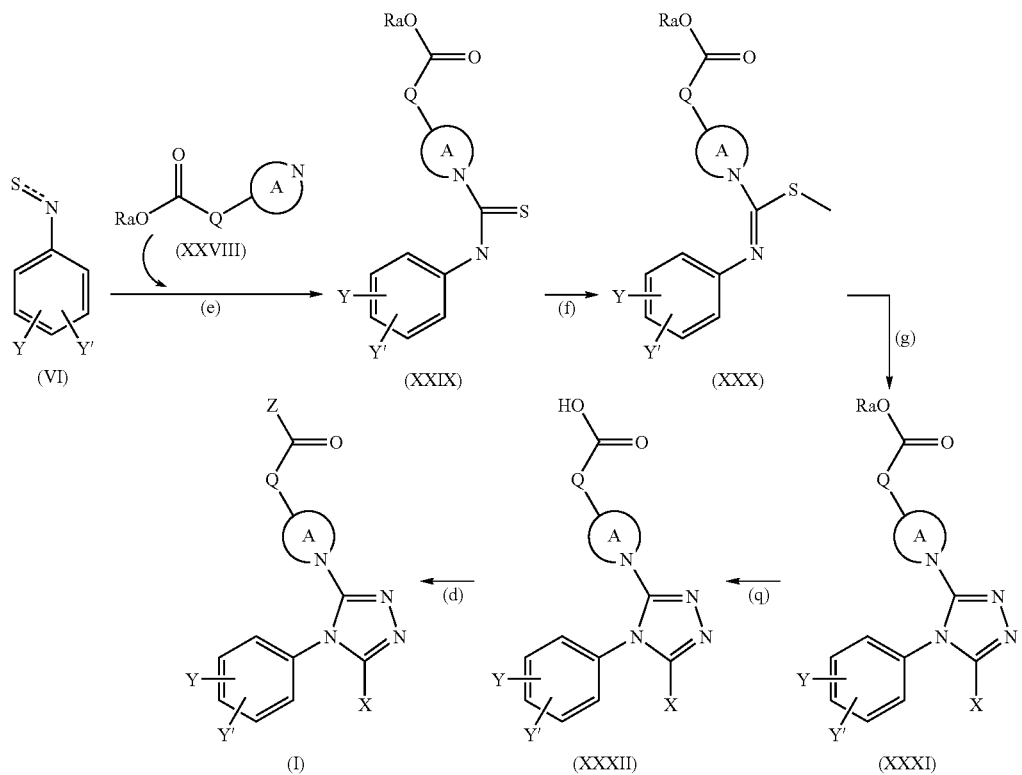

Ra represents C1-4 alkyl or benzyl, and is preferably Me or Et.

Compounds of formula (XXVIII) are either commercially available or may be prepared from commercially available compounds, using standard chemical transformations.

Compounds of formula (XXIX) may be prepared by reaction of compound (XXVIII) with the appropriate isothiocyanate (VI), by analogy with the methods previously described in Step (e).

The compound of formula (XXX) may be prepared by alkylation of compound (XXIX), by analogy with the methods previously described in Step (f).

The compound of formula (XXXI) may be prepared by reaction of compound (XXX) with a suitable hydrazide, as previously described in Step (g).

Step (q): Hydrolysis of ester (XXXI) using a suitable acid or base catalyst, preferably an alkali metal base (e.g. NaOH, KOH, or LiOH) in a suitable aqueous solvent (e.g. dioxan, or MeOH) at between room temperature and the reflux temperature of the reaction, for between 2 and 48 hours. Preferred conditions: 1 eq. (XXXI), 5-10 eq. NaOH solution, in dioxan at between room temperature and reflux, for between 2 and 16 hours.

Compounds of formula (I) may be prepared by reaction of Z—H (containing a reactive N atom) with acid (XXXII), by analogy with the methods previously described for Step (d). Preferred conditions: 1 eq. acid (XXXII), 1.5 eq. amine (ZH), 4 eq. Et$_3$N, 1.5 eq. WSCDI, 1.5 eq. HOBT, in DCM at room temperature, for 24 hours.

Compounds of formula (XXXII) may alternatively be prepared by hydrolysis of the corresponding nitrile compound (XXXIII), under standard conditions (e.g. 5 eq. KOH, 1 eq. nitrile (XXXIII), in ethanol/ethylene glycol dimethyl ether at reflux).

Compounds of formula (XXXIII) may be prepared as shown in Scheme 11.

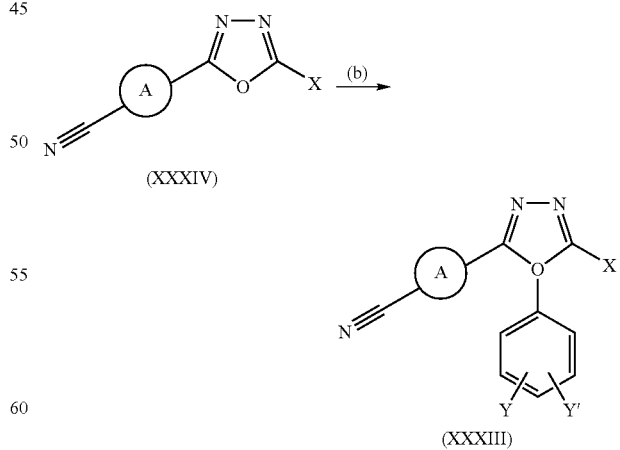

Compounds of formula (XXXIII), wherein Q is a direct link and ring A is attached to the triazole ring through a nitrogen atom, may be prepared from the appropriate isothiocyanate (VI) and an A ring containing nitrile,

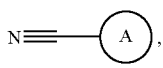

by analogy with the methods described in Scheme 9.

Compounds of formula (I), wherein V represents an oxygen atom, may be prepared as shown in Scheme 12.

ture for about 18 hours. Preferred conditions: 1 eq. (XXXVII), 4 eq. mCPBA, in DCM at room temperature for 18 hours.

Step (v): Compounds of formula (I) may be prepared by reaction of sulphoxide (XXXVIII) with an excess of alcohol (XXXIX) in the presence of a suitable base (e.g. NaH, or KOt-Bu), in a suitable solvent (e.g. THF, or ether) at between 0° and room temperature for up to 18 hours. Preferred con- Scheme 12

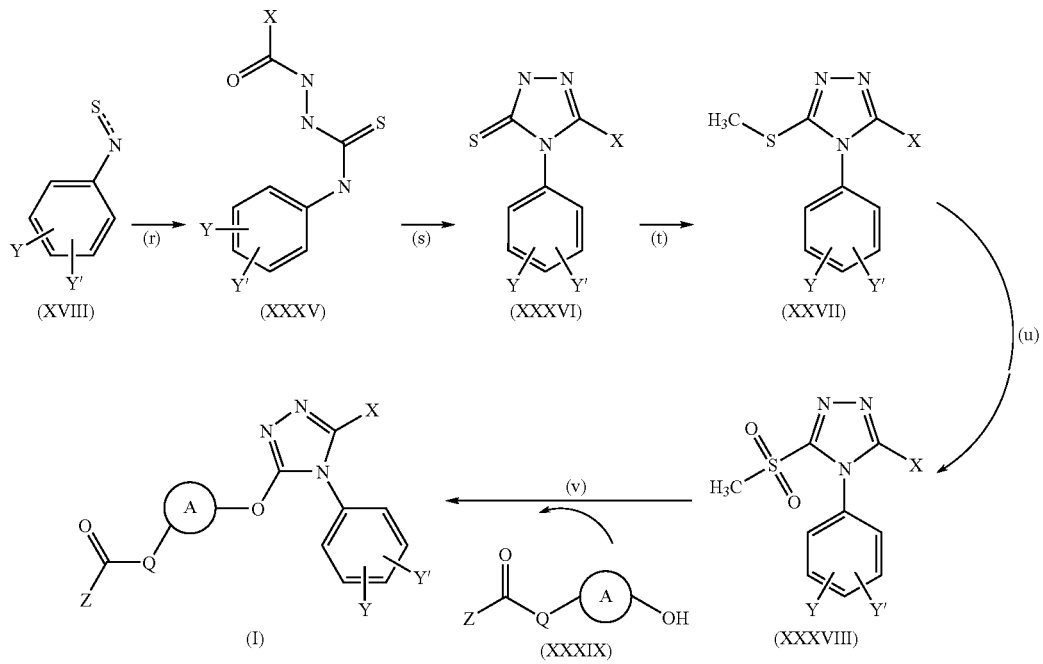

Step (r): The compound of formula (XXXV) may be prepared by reaction of hydrazide (XCONHNH$_2$) with isothiocyanate (VI) by analogy with the methods previously described in Step (e). Preferred conditions: 1 eq. isothiocyanate, 1 eq. hydrazide, in EtOH at room temperature for 72 hours.

Step (s): Compounds of formula (XXXVI) may be prepared by cyclisation of compound (XXXV) under acid or base conditions, preferably base catalysis (e.g. alkali metal hydroxide) in aqueous solvent (e.g. water/EtOH), at an elevated temperature, for about 24 hours. Preferred conditions: 1 eq. (XXXV), 10 eq. NaOH$_{(aq)}$ in EtOH at 80° C. for 18 hours.

Step (t): Alkylation of compound (XXXVI) to provide compound (XXXVII) may be achieved by treatment with a suitable alkylating agent (e.g. MeI, or Me-Tosylate), by analogy with the methods previously described in Step (f). Preferred conditions: 1 eq. (XXXVI), 1 eq. KOt-Bu, 1 eq. Me-Tosylate, in THF at between room temperature and reflux for 3 hours.

Step (u): Compounds of formula (XXXVIII) may be obtained by oxidation of compound (XXXVII) by treatment with a suitable oxidising agent (e.g. mCPBA, or hydrogen peroxide) in a suitable solvent (e.g. DCM) at room temperaditions: 1 eq. (XXXVIII), 2 eq. NaH, 2 eq. alcohol (XXXIX), in THF for 18 hours at room temperature.

Compounds of formula (XXXIX) are either commercially available or may be prepared from commercially available compounds, using standard chemical transformations.

Certain compounds of formulae (I) (III), (IV), (V), (XXII), and (XXXI) may undergo functional group interconversions (e.g. alkylation, or hydrolysis) to provide alternative compounds of formulae (I) (III), (IV), (V), (XXII), or (XXXI), respectively.

Compounds of the invention intended for pharmaceutical use may be administered as crystalline or amorphous products. They may be obtained, for example, as solid plugs, powders, or films by methods such as precipitation, crystallisation, freeze drying, spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a formulation in association with one or more pharmaceutically acceptable excipients. The term 'excipient' is used herein to describe any ingredient other than the compound(s) of the invention. The choice of excipient will to a large extent depend on factors such as the particular mode of administration, the effect of the excipient on solubility and stability, and the nature of the dosage form.

A further aspect of the invention is a pharmaceutical formulation including a compound of formula (I), or a pharmaceutically acceptable salt or solvate thereof, together with a pharmaceutically acceptable excipient, diluent or carrier. In a further embodiment there is provided the pharmaceutical formulation for administration either prophylactically or when pain commences.

Pharmaceutical compositions suitable for the delivery of compounds of the present invention and methods for their preparation will be readily apparent to those skilled in the art. Such compositions and methods for their preparation may be found, for example, in *Remington's Pharmaceutical Sciences,* 19th Edition (Mack Publishing Company, 1995).

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, solid solution, liposome, films, ovules, sprays and liquid formulations.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986, by Liang and Chen (2001).

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet.

Other possible ingredients include anti-oxidants, colourants, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in *Pharmaceutical Dosage Forms: Tablets,* Vol. 1, by H. Lieberman and L. Lachman (Marcel Dekker, New York, 1980).

Consumable oral films for human or veterinary use are typically pliable water-soluble or water-swellable thin film dosage forms which may be rapidly dissolving or mucoadhesive and typically comprise a compound of formula (I), a film-forming polymer, a binder, a solvent, a humectant, a plasticiser, a stabiliser or emulsifier, a viscosity-modifying agent and a solvent. Some components of the formulation may perform more than one function.

The compound of formula (I) may be water-soluble or insoluble. A water-soluble compound typically comprises from 1 weight % to 80 weight %, more typically from 20 weight % to 50 weight %, of the solutes. Less soluble compounds may comprise a greater proportion of the composition, typically up to 88 weight % of the solutes. Alternatively, the compound of formula (I) may be in the form of multiparticulate beads.

The film-forming polymer may be selected from natural polysaccharides, proteins, or synthetic hydrocolloids and is typically present in the range 0.01 to 99 weight %, more typically in the range 30 to 80 weight %.

Other possible ingredients include anti-oxidants, colorants, flavourings and flavour enhancers, preservatives, salivary stimulating agents, cooling agents, co-solvents (including oils), emollients, bulking agents, anti-foaming agents, surfactants and taste-masking agents.

Films in accordance with the invention are typically prepared by evaporative drying of thin aqueous films coated onto a peelable backing support or paper. This may be done in a drying oven or tunnel, typically a combined coater dryer, or by freeze-drying or vacuuming.

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in *Pharmaceutical Technology On-line,* 25(2), 1-14, by Verma et al (2001). The use of chewing gum to achieve controlled release is described in WO 00/35298.

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and poly(dl-lactic-coglycolic) acid (PGLA) microspheres.

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958, by Finnin and Morgan (October 1999).

Other means of topical administration include delivery by electroporation, iontophoresis, phonophoresis, sonophoresis and microneedle or needle-free (e.g. Powderject™, Bioject™, etc.) injection.

Formulations for topical administration may be formulated to be immediate and/or modified release. Modified release formulations include delayed-, sustained-, pulsed-, controlled-, targeted and programmed release.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 µg to 20 mg of the compound of the invention per actuation and the actuation volume may vary from 1 µl to 100 µl. A typical formulation may comprise a compound of formula (I), propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, PGLA. Modified release formulations include delayed-, sustained-, pulsed-, controlled-, targeted and programmed release.

In the case of dry powder inhalers and aerosols, the dosage unit is determined by means of a valve, which delivers a metered amount. The overall daily dose will typically be in the range 0.01 µg to 15 mg which may be administered in a single dose or, more usually, as divided doses throughout the day.

The compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

The compounds of the invention may also be administered directly to the eye or ear, typically in the form of drops of a micronised suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

Inasmuch as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions.

Thus the kit of the invention comprises two or more separate pharmaceutical compositions, at least one of which contains a compound of formula (I) in accordance with the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

For administration to human patients, the total daily dose of the compounds of the invention is typically in the range 0.01 mg to 15 mg depending, of course, on the mode of administration. The total daily dose may be administered in single or divided doses and may, at the physician's discretion, fall outside of the typical range given herein.

These dosages are based on an average human subject having a weight of about 60 kg to 70 kg. The physician will readily be able to determine doses for subjects whose weight falls outside this range, such as infants and the elderly.

For the avoidance of doubt, references herein to 'treatment' include references to curative, palliative and prophylactic treatment.

The compounds of the present invention may be tested in the screens set out below:

1.0 $V_{1A}$ Filter Binding Assay 1.1 Membrane Preparation

Receptor binding assays were performed on cellular membranes prepared from CHO cells stably expressing the human $V_{1A}$ receptor, (CHO-h$V_{1A}$). The CHO-h$V_{1A}$ cell line was kindly provided under a licensing agreement by Marc Thibonnier, Dept. of Medicine, Case Western Reserve University School of Medicine, Cleveland, Ohio. CHO-h$V_{1A}$ cells were routinely maintained at 37° C. in humidified atmosphere with 5% $CO_2$ in DMEM/Hams F12 nutrient mix supplemented with 10% fetal bovine serum, 2 mM L-glutamine, 15 mM HEPES and 400 µg/ml G418. For bulk production of cell pellets, adherent CHO-h$V_{1A}$ cells were grown to confluency of 90-100% in 850 $cm^2$ roller bottles containing a medium of DMEM/Hams F12 Nutrient Mix supplemented with 10,% fetal bovine serum, 2 mM L-glutamine and 15 mM HEPES. Confluent CHO-h$V_{1A}$ cells were washed with phosphate-buffered saline (PBS), harvested into ice cold PBS and centrifuged at 1,000 rpm. Cell pellets were stored at −80° C. until use. Cell pellets were thawed on ice and homogenised in membrane preparation buffer consisting of 50 mM Tris-HCl, pH 7.4, 5 mM $MgCl_2$ and supplemented with a protease inhibitor cocktail, (Roche). The cell homogenate was centrifuged at 1000, rpm, 10 min, 4° C. and the supernatant was removed and stored on ice. The remaining pellet was homogenised and centrifuged as before. The supernatants were pooled and centrifuged at 25,000×g for 30 min at 4° C. The pellet was resuspended in freezing buffer consisting of 50 mM Tris-HCl, pH 7.4, 5 mM $MgCl_2$ and 20% glycerol and stored in small aliquots at −80° C. until use. Protein concentration was determined using Bradford reagent and BSA as a standard.

1.2 $V_{1A}$ Filter Binding

Protein linearity followed by saturation binding studies were performed on each new batch of membrane. Membrane concentration was chosen that gave specific binding on the linear portion of the curve. Saturation binding studies were then performed using various concentrations of [$^3$H]-arginine vasopressin, [$^3$H]-AVP (0.05 nM-100 nM) and the $K_d$ and $B_{max}$ determined.

Compounds were tested for their effects on [$^3$H]-AVP binding to CHO-h$V_{1A}$ membranes, ($^3$H-AVP; specific activity 65.5 Ci/mmol; NEN Life Sciences). Compounds were solubilised in dimethylsulfoxide (DMSO) and diluted to working concentration of 10% DMSO with assay buffer containing 50 mM Tris-HCL pH 7.4, 5 mM $MgCl_2$ and 0.05% BSA. 25 µl compound and 25 µl [$^3$H]-AVP, (final concentration at or below $K_d$ determined for membrane batch, typically 0.5 nM-0.6 nM) were added to a 96-well round bottom polypropylene plate. The binding reaction was initiated by the addition of 200 µl membrane and the plates were gently shaken for 60 min at room temperature. The reaction was terminated by rapid filtration using a Filtermate Cell Harvester (Packard Instruments) through a 96-well GF/B UniFilter Plate which had been presoaked in 0.5% polyethyleneimine to prevent peptide sticking. The filters were washed three times with 1 ml ice cold wash buffer containing 50 mM Tris-HCL pH 7.4 and 5 mM $MgCl_2$. The plates were dried and 50 µl Microscint-0 (Packard instruments) was added to each well. The plates were sealed and counted on a TopCount Microplate Scintillation Counter (Packard Instruments). Non-specific binding (NSB) was determined using 1 µM unlabelled d(CH2)5Tyr(Me)AVP ([β-mercapto-β,β-cyclopentamethylenepropionyl, 0-Me-Tyr$^2$,Arg$^8$]-vasopressin) (βMCPVP), (Sigma). The radioligand binding data was analysed using a four parameter logistic equation with the min forced to 0%. The slope was free fitted and fell between −0.75 and −1.25 for valid curves. Specific binding was calculated by subtracting the mean NSB cpm from the mean Total cpm. For test compounds the amount of ligand bound to the receptor was expressed as % bound=(sample cpm−mean NSB cpm)/specific binding cpm×100. The % bound was plotted against the concentration of test compound and a sigmoidal curve was fitted. The inhibitory dissociation constant ($K_i$) was calculated using the Cheng-Prusoff equation: $K_i=IC_{50}/(1+[L]/K_d)$ where [L] is the concentration of ligand present in the well and $K_d$ is the dissociation constant of the radioligand obtained from Scatchard plot analysis.

2.0 $V_{1A}$ Functional Assay; Inhibition of AVP/V1A-R Mediated $Ca^{2+}$ Mobilization by FLIPR (Fluorescent Imaging Plate Reader) (Molecular Devices)

Intracellular calcium release was measured in CHO-h$V_{1A}$ cells using FLIPR, which allows the rapid detection of calcium following receptor activation. The CHO-h$V_{1A}$ cell line was kindly provided under a licensing agreement by Marc Thibonnier, Dept. of Medicine, Case Western Reserve University School of Medicine, Cleveland, Ohio. CHO—$V_{1A}$ cells were routinely maintained at 37° C. in humidified atmosphere with 5% $CO_2$ in DMEM/Hams F12 nutrient mix supplemented with 10% fetal bovine serum, 2 mM L-glutamine, 15 mM HEPES and 400 µg/ml G418. On the afternoon before the assay cells were plated at a density of 20,000 cells per well into black sterile 96-well plates with clear bottoms to allow cell inspection and fluorescence measurements from the bottom of each well. Wash buffer containing Dulbecco's phosphate buffered saline (DPBS) and 2.5 mM probenecid and loading dye consisting of cell culture medium containing 4 µM Fluo-3-AM (dissolved in DMSO and pluronic acid), (Molecular Probes) and 2.5 mM probenecid was prepared fresh on the day of assay. Compounds were solubilised in DMSO and diluted in assay buffer consisting of DPBS containing 1% DMSO, 0.1% BSA and 2.5 mM probenecid. The cells were incubated with 100 µl loading dye per well for 1 hour at 37° C. in humidified atmosphere with 5% $CO_2$. After dye loading the cells were washed three times in 100 µl wash buffer using a Denley plate washer. 100 µl wash buffer was left in each well. Intracellular fluorescence was measured using FLIPR. Fluorescence readings were obtained at 2 s intervals with 50 µl of the test compound added after 30 s. An additional 155 measurements at 2 s intervals were then taken to detect any compound agonistic activity. 50 µl of arginine vasopressin (AVP) was then added so that the final assay volume was 200 µl. Further fluorescence readings were collected at 1 s intervals for 120 s. Responses were measured as peak fluorescence intensity (FI). For pharmacological characterization a basal FI was subtracted from each fluorescence response. For AVP dose response curves, each response was expressed as a % of the response to the highest concentration of AVP in that row. For $IC_{50}$ determinations, each response was expressed as a % of the response to AVP. $IC_{50}$ values were converted to a modified $K_b$ value using the Cheng-Prusoff equation which takes into account the agonist concentration, [A], the agonist $EC_{50}$ and the slope: $K_b = IC_{50}/(2+[A]/A_{50})^{1/n}-1$ where [A] is the concentration of AVP, $A_{50}$ is the $EC_{50}$ of AVP from the dose response curve and n=slope of the AVP dose response curve.

The compounds of the invention may be administered alone or in combination with one or more other compounds of the invention or in combination with one or more other drugs (or as any combination thereof). The compounds of the present invention may be administered in combination with an oral contraceptive. Thus in a further aspect of the invention, there is provided a pharmaceutical product containing an V1a antagonist and an oral contraceptive as a combined preparation for simultaneous, separate or sequential use in the treatment of dysmenorrhoea.

The compounds of the present invention may be administered in combination with a PDE5 inhibitor. Thus in a further aspect of the invention, there is provided a pharmaceutical product containing a V1a antagonist and a PDEV inhibitor as a combined preparation for simultaneous, separate or sequential use in the treatment of dysmenorrhoea.

PDEV inhibitors useful for combining with V1a antagonists include, but are not limited to:

(i) The PDE5 inhibitors mentioned in International Patent Application publication nos. WO03/000691; WO02/64590; WO02/28865; WO02/28859; WO02/38563; WO02/36593; WO02/28858; WO02/00657; WO02/00656; WO02/10166; WO02/00658; WO01/94347; WO01/94345; WO00/15639 and WO00/15228;

(ii) The PDE5 inhibitors mentioned in U.S. Pat. Nos. 6,143,746; 6,143,747 and 6,043,252;

(iii) the pyrazolo[4,3-d]pyrimidin-7-ones disclosed in EP-A-0463756; the pyrazolo [4,3-d]pyrimidin-7-ones disclosed in EP-A-0526004; the pyrazolo[4,3-d]pyrimidin-7-ones disclosed in published international patent application WO 93/06104; the isomeric pyrazolo[3,4-d]pyrimidin-4-ones disclosed in published international patent application WO 93/07149; the quinazolin-4-ones disclosed in published international patent application WO 93/12095; the pyrido [3,2-d]pyrimidin-4-ones disclosed in published international patent application WO 94/05661; the purin-6-ones disclosed in published international patent application WO 94/00453; the pyrazolo [4,3-d]pyrimidin-7-ones disclosed in published international patent application WO 98/49166; the pyrazolo[4,3-d]pyrimidin-7-ones disclosed in published international patent application WO 99/54333; the pyrazolo[4,3-d]pyrimidin-4-ones disclosed in EP-A-0995751; the pyrazolo[4,3-d]pyrimidin-7-ones disclosed in published international patent application WO 00/24745; the pyrazolo[4,3-d]pyrimidin-4-ones disclosed in EP-A-0995750; the hexahydropyrazino [2',1': 6,1]pyrido [3,4-b]indole-1,4-diones disclosed in published international application WO95/19978; the pyrazolo[4,3-d]pyrimidin-4-ones disclosed in WO00/27848; the imidazo[5,1-f][1,2,4]triazin-ones disclosed in EP-A-1092719 and in published international application WO 99/24433 and the bicyclic compounds disclosed in published international application WO 93/07124; the pyrazolo [4,3-d]pyrimidin-7-ones disclosed in published international application WO 01/27112; the pyrazolo[4,3-d]pyrimidin-7-ones disclosed in published international application WO 01/27113; the compounds disclosed in EP-A-1092718 and the compounds disclosed in EP-A-1092719; the tricyclic compounds disclosed in EP-A-1241170; the alkyl sulphone compounds disclosed in published international application WO 02/074774; the compounds disclosed in published international application WO 02/072586; the compounds disclosed in published international application WO 02/079203 and the compounds disclosed in WO 02/074312.

(iv) Preferably 5-[2-ethoxy-5-(4-methyl-1-piperazinylsulphonyl)phenyl]-1-methyl-3-n-propyl-1,6-dihydro-7H-pyrazolo[4,3-d]pyrimidin-7-one (sildenafil, e.g. as sold as Viagra®) also known as 1-[[3-(6,7-dihydro-1-methyl-7-oxo-3-propyl-1H-pyrazolo[4,3-d]pyrimidin-5-yl)-4-ethoxyphenyl]sulphonyl]-4-methylpiperazine (see EP-A-0463756); 5-(2-ethoxy-5-morpholinoacetylphenyl)-1-methyl-3-n-propyl-1,6-dihydro-7H-pyrazolo[4,3-d]pyrimidin-7-one (see EP-A-0526004); 3-ethyl-5-[5-(4-ethylpiperazin-1-ylsulphonyl)-2-n-propoxyphenyl]-2-(pyridin-2-yl)methyl-2,6-dihydro-7H-pyrazolo[4,3-d]pyrimidin-7-one (see WO98/49166); 3-ethyl-5-[5-(4-ethylpiperazin-1-ylsulphonyl)-2-(2-methoxyethoxy)pyridin-3-yl]-2-(pyridin-2-yl)methyl-2,6-dihydro-7H-pyrazolo[4,3-d]pyrimidin-7-one (see WO99/54333); (+)-3-ethyl-5-[5-(4-ethylpiperazin-1- ylsulphonyl)-2-(2-methoxy-1(R)-methylethoxy)pyridin-3-yl]-2-methyl-2,6-dihydro-7H-pyrazolo[4,3-d]pyrimidin-7-one, also known as 3-ethyl-5-{5-[4-ethylpiperazin-1-ylsulphonyl]-2-([(1R)-2-methoxy-1-methylethyl]oxy)pyridin-3-yl}-2-methyl-2,6-dihydro-7H-pyrazolo[4,3-d]pyrimidin-7-one (see WO99/54333); 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, also known as 1-{6-ethoxy-5-[3-ethyl-6,7-dihydro-2-(2-methoxyethyl)-7-oxo-2H-pyrazolo[4,3-d]pyrimidin-5-yl]-3-pyridylsulphonyl}-4-ethylpiperazine (see WO 01/27113, Example 8); 5-[2-iso Butoxy-5-(4-ethylpiperazin-1-ylsulphonyl)pyridin-3-yl]-3-ethyl-2-(1-methylpiperidin-4-yl)-2,6-dihydro-7H-pyrazolo[4,3-d]pyrimidin-7-one see WO 01/27113, Example 15); 5-[2-Ethoxy-5-(4-ethylpiperazin-1-ylsulphonyl)pyridin-3-yl]-3-ethyl-2-phenyl-2,6-dihydro-7H-pyrazolo[4,3-d]pyrimidin-7-one (see WO 01/27113, Example 66); 5-(5-Acetyl-2-propoxy-3-pyridinyl)-3-ethyl-2-(1-isopropyl-3-azetidinyl)-2,6-dihydro-7H-pyrazolo[4,3-d]pyrimidin-7-one (see WO 01/27112, Example 124); 5-(5-Acetyl-2-butoxy-3-pyridinyl)-3-ethyl-2-(1-ethyl-3-azetidinyl)-2,6-dihydro-7H-pyrazolo[4,3-d]pyrimidin-7-one (see WO 01/27112, Example 132); (6R, 12aR)-2,3,6,7,12,12a-hexahydro-2-methyl-6-(3,4-methylenedioxyphenyl)pyrazino[2', 1':6,1]pyrido[3,4-b]indole-1,4-dione (tadalafil, IC-351, Cialis®), i.e. the compound of examples 78 and 95 of published international application WO95/19978, as well as the compound of examples 1, 3, 7 and 8; 2-[2-ethoxy-5-(4-ethylpiperazin-1-yl-1-sulphonyl)-phenyl]-5-methyl-7-propyl-3H-imidazo[5,1-f][1,2,4]triazin-4-one (vardenafil, LEVITRA®) also known as 1-[[3-(3,4-dihydro-5-methyl-4-oxo-7-propylimidazo[5,1-f]-as-triazin-2-yl)-4-ethoxyphenyl]sulphonyl]-4-ethylpiperazine, i.e. the compound of examples 20, 19, 337 and 336 of published international application WO99/24433; the compound of example 11 of published international application WO93/07124 (EISAI); compounds 3 and 14 from Rotella D P, *J. Med. Chem.*, 2000, 43, 1257; 4-(4-chlorobenzyl)amino-6,7,8-trimethoxyquinazoline; N-[[3-(4,7-dihydro-1-methyl-7-oxo-3-propyl-1H-pyrazolo[4,3-d]-pyrimidin-5-yl)-4-propoxyphenyl]sulfonyl]-1-methyl2-pyrrolidinepropanamide ["DA-8159" (Example 68 of WO00/27848)]; and 7,8-dihydro-8-oxo-6-[2-propoxyphenyl]-1H-imidazo[4,5-g]quinazoline and 1-[3-[1-[(4-fluorophenyl)methyl]-7,8-dihydro-8-oxo-1H-imidazo[4,5-g]quinazolin-6-yl]-4-propoxyphenyl]carboxamide.

(v) 4-bromo-5-(pyridylmethylamino)-6-[3-(4-chlorophenyl)-propoxy]-3(2H)pyridazinone; 1-[4-[(1,3-benzodioxol-5-ylmethyl)amiono]-6-chloro-2-quinozolinyl]-4-piperidine-carboxylic acid, monosodium salt; (+)-cis-5,6a,7,9,9,9a-hexahydro-2-[4-(trifluoromethyl)-phenylmethyl-5-methyl-cyclopent-4,5]imidazo[2,1-b]purin-4(3H)one; furazlocillin; cis-2-hexyl-5-methyl-3,4,5,6a,7,8,9,9a-octahydrocyclopent[4,5]-imidazo[2,1-b]purin-4-one; 3-acetyl-1-(2-chlorobenzyl)-2-propylindole-6-carboxylate; 3-acetyl-1-(2-chlorobenzyl)-2-propylindole-6-carboxylate; 4-bromo-5-(3-pyridylmethylamino)-6-(3-(4-chlorophenyl) propoxy)-3-(2H)pyridazinone; I-methyl-5(5-morpholinoacetyl-2-n-propoxyphenyl)-3-n-propyl-1,6-dihydro-7H-pyrazolo(4,3-d)pyrimidin-7-one; 1-[4-[(1,3-benzodioxol-5-ylmethyl)amino]-6-chloro-2-quinazinyl]-4-piperidinecarboxylic acid, monosodium salt; Pharmaprojects No. 4516 (Glaxo Wellcome); Pharmaprojects No. 5051 (Bayer); Pharmaprojects No. 5064 (Kyowa Hakko; see WO 96/26940); Pharmaprojects No. 5069 (Schering Plough); GF-196960 (Glaxo Wellcome); E-8010 and E-4010 (Eisai); Bay-38-3045 & 38-9456 (Bayer); FR229934 and FR226807 (Fujisawa); and Sch-51866.

Preferably the PDEV inhibitor is selected from sildenafil, tadalafil, vardenafil, DA-8159 and 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one.

Most preferably the PDE5 inhibitor is sildenafil and pharmaceutically acceptable salts thereof. Sildenafil citrate is a preferred salt.

The compounds of the present invention may be administered in combination with an NO donor. Thus in a further aspect of the invention, there is provided a pharmaceutical product containing a V1a antagonist and a NO donor as a combined preparation for simultaneous, separate or sequential use in the treatment of dysmenorrhoea.

The compounds of the present invention may be administered in combination with L-arginine, or as an arginate salt. Thus in a further aspect of the invention, there is provided a pharmaceutical product containing a V1a antagonist and L-arginine as a combined preparation for simultaneous, separate or sequential use in the treatment of dysmenorrhoea.

The compounds of the present invention may be administered in combination with a COX inhibitor. Thus in a further aspect of the invention, there is provided a pharmaceutical product containing a V1a antagonist and a COX inhibitor as a combined preparation for simultaneous, separate or sequential use in the treatment of dysmenorrhoea.

COX inhibitors useful for combining with the compounds of the present invention include, but are not limited to:
(i) ibuprofen, naproxen, benoxaprofen, flurbiprofen, fenoprofen, fenbufen, ketoprofen, indoprofen, pirprofen, carprofen, oxaprozin, prapoprofen, miroprofen, tioxaprofen, suprofen, alminoprofen, tiaprofenic acid, fluprofen, bucloxic acid, indomethacin, sulindac, tolmetin, zomepirac, diclofenac, fenclofenec, alclofenac, ibufenac, isoxepac, furofenac, tiopinac, zidometacin, acetyl salicylic acid, indometacin, piroxicam, tenoxicam, nabumetone, ketorolac, azapropazone, mefenamic acid, tolfenamic acid, diflunisal, podophyllotoxin derivatives, acemetacin, droxicam, floctafenine, oxyphenbutazone, phenylbutazone, proglumetacin, acemetacin, fentiazac, clidanac, oxipinac, mefenamic acid, meclofenamic acid, flufenamic acid, niflumic acid, flufenisal, sudoxicam, etodolac, piprofen, salicylic acid, choline magnesium trisalicylate, salicylate, benorylate, fentiazac, clopinac, feprazone, isoxicam and 2-fluoro-a-methyl[1,1'-biphenyl]-4-acetic acid, 4-(nitrooxy)butyl ester (See Wenk, et al., *Europ. J. Pharmacol.* 453: 319-324 (2002));
(ii) meloxicam, (CAS registry number 71125-38-7; described in U.S. Pat. No. 4,233,299), or a pharmaceutically acceptable salt or prodrug thereof;
(iii) Substituted benzopyran derivatives that are described in U.S. Pat. No. 6,271,253. Also benzopyran derivatives described in U.S. Pat. Nos. 6,034,256 and 6,077,850 along with International Publication No's WO 98/47890 and WO 00/23433;
(iv) Chromene COX2 selective inhibitors described in U.S. Pat. No. 6,077,850 and U.S. Pat. No. 6,034,256;
(v) The compounds described in International Patent Application Publication No's WO 95/30656, WO 95/30652, WO 96/38418 and WO 96/38442, and the compounds described in European Patent Application Publication No. 799823, along with the pharmaceutically acceptable derivatives thereof;

(vi) celecoxib (U.S. Pat. No. 5,466,823), valdecoxib (U.S. Pat. No. 5,633,272), deracoxib (U.S. Pat. No. 5,521,207), rofecoxib (U.S. Pat. No. 5,474,995), etoricoxib (International Patent Application Publication No. WO 98/03484), JTE-522 (Japanese Patent Application Publication No. 9052882), or a pharmaceutically acceptable salt or prodrug thereof;

(vii) Parecoxib (described in U.S. Pat. No. 5,932,598), which is a therapeutically effective prodrug of the tricyclic Cox-2 selective inhibitor valdecoxib (described in U.S. Pat. No. 5,633,272), in particular sodium parecoxib;

(viii) ABT-963 (described in International Patent Application Publication No. WO 00/24719)

(ix) Nimesulide (described in U.S. Pat. No. 3,840,597), flosulide (discussed in J. Carter, *Exp. Opin. Ther. Patents*, 8(1), 21-29 (1997)), NS-398 (disclosed in U.S. Pat. No. 4,885,367), SD 8381 (described in U.S. Pat. No. 6,034,256), BMS-347070 (described in U.S. Pat. No. 6,180,651), S-2474 (described in European Patent Publication No. 595546) and MK-966 (described in U.S. Pat. No. 5,968,974);

(x) The compounds and pharmaceutically acceptable derivatives described in U.S. Pat. Nos. 6,395,724, 6,077,868, 5,994,381, 6,362,209, 6,080,876, 6,133,292, 6,369,275, 6,127,545, 6,130,334, 6,204,387, 6,071,936, 6,001,843, 6,040,450, International Patent Application Publication No WO 96/03392, International Patent Application Publication No WO 96/24585, U.S. Pat. Nos. 6,340,694, 6,376,519, 6,153,787, 6,046,217, 6,329,421, 6,239,137, 6,136,831, 6,297,282, 6,239,173, 6,303,628, 6,310,079, 6,300,363, 6,077,869, 6,140,515, 5,994,379, 6,028,202, 6,040,320, 6,083,969, 6,306,890, 6,307,047, 6,004,948, 6,169,188, 6,020,343, 5,981,576, 6,222,048, 6,057,319, 6,046,236, 6,002,014, 5,945,539, 6,359,182, International Patent Application Publication No. WO97/13755, International Patent Application Publication No. WO 96/25928, International Patent Application Publication No. WO 96/374679, International Patent Application Publication No. WO 95/15316, International Patent Application Publication No. WO 95/15315, International Patent Application Publication No. WO 96/03385, International Patent Application No. WO 95/00501, International Patent Application No. WO 94/15932, International Patent Application Publication No. WO 95/00501, International Patent Application Publication No. WO 94/27980, International Patent Application Publication No. WO 96/25405, International Patent Application Publication No. WO 96/03388, International Patent Application Publication No. WO 96/03387, U.S. Pat. No. 5,344,991, International Patent Application Publication No. WO 95/00501, International Patent Application Publication No. WO 96/16934, International Patent Application Publication No. WO 96/03392, International Patent Application Publication No. WO 96/09304, International Patent Application Publication No. WO 98/47890, and International Patent Application Publication No. WO 00/24719.

The contents of any of the U.S. patents, and in particular the general formulae of the therapeutically active compounds of the claims and exemplified compounds therein, are incorporated herein in their entirety by reference thereto.

The following Preparations and Examples illustrate the preparation of compounds of formula (I).

$^1$H Nuclear magnetic resonance (NMR) spectra were in all cases consistent with the proposed structures. Characteristic chemical shifts (δ) are given in parts-per-million downfield from tetramethylsilane using conventional abbreviations for designation of major peaks: e.g. s, singlet; d, doublet; t, triplet; q, quartet; m, multiplet; br, broad. The mass spectra (m/z) were recorded using either electrospray ionisation (ESI) or atmospheric pressure chemical ionisation (APCI). The following abbreviations have been used for common solvents: $CDCl_3$, deuterochloroform; $D_6$-DMSO, deuterodimethylsulphoxide; $CD_3OD$, deuteromethanol; THF, tetrahydrofuran. "Ammonia" refers to a concentrated solution of ammonia in water possessing a specific gravity of 0.88. Where thin layer chromatography (TLC) has been used it refers to silica gel TLC using silica gel 60 F254 plates, $R_f$ is the distance traveled by a compound divided by the distance traveled by the solvent front on a TLC plate. When microwave radiation is employed, the two microwaves used are the Emrys Creator and the Emrys Liberator, both supplied by Personal Chemistry Ltd. The power range is 15-300 W at 2.45 GHz. The actual power supplied varies during the course of the reaction in order to maintain a constant temperature.

Preparation 2: 4-(5-Methyl-[1,3,4]oxadiazol-2-yl)-piperidine-1-carboxylic acid tert-butyl ester

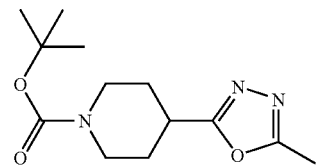

To a solution of 9.0 g of 4-Hydrazinocarbonyl-piperidine-1-carboxylic acid tert-butyl ester (see reference WO 9703986 A1 19970206) (37 mmoles, 1 eq.) in 40 ml of THF, were added 8.1 ml of (55.4 mmoles, 1.5 eq.). The reaction mixture was then stirred at 50° C. for 4 hours under nitrogen. The solvent was removed under reduced pressure, the residue dissolved in 40 ml of toluene, and 400 mg of para toluene sulfonic acid were added. The mixture was then heated at 100° C. under nitrogen for 18 hours, the volatiles were removed under reduced pressure and the residue was partitioned between methylene chloride and an aqueous solution of sodium bicarbonate. The organic phase was dried over magnesium sulfate and filtered. The volatiles were removed under reduced pressure and the residue was purified by column chromatography on silica gel using methylene chloride/methanol as eluant (98:2 v/v to 95:5 v/v) to afford 8.07 g of the title compound as a white solid (81%).

$^1$H NMR (400 MHz, $CD_3OD$): δ 1.42 (s, 9H), 1.70 (m, 2H), 2.05 (m, 2H), 2.50 (s, 3H), 3.00 (m, 2H), 3.15 (m, 1H), 4.05 (m, 2H); LCMS: m/z APCI$^+$, 268 [MH]$^+$; Found; C, 58.26%; H, 7.96%; N, 15.78%; $C_{13}H_{21}N_3O_3$ requires C, 58.41%, H, 7.92%, N, 15.72%

Preparation 2a: 4-[4-(4-Chloro-phenyl)-5-methyl-4H-[1,2,4]triazol-3-yl]-piperidine

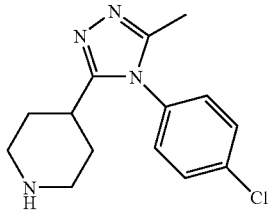

4.0 g of the compound of preparation 1 (15 mmoles, 1 eq.) were dissolved in 100 ml of toluene. 2.1 g of para chloro aniline (16.5 mmoles, 1.1 eq.) were added, followed by 2 ml of TFA. The solution was heated at 110° C. for 16 hours, 2 ml of TFA were added, and the solution was heated at 110° C. for a further 48 hours. The reaction mixture was then cooled, an aqueous solution of sodium bicarbonate added and the organic phase was decanted. The aqueous phase was basified with potassium carbonate and extracted four times with methylene chloride (50 ml). The methylene chloride solution was dried over magnesium sulfate and the solvent was removed in vacuo, to afford 2.90 g of the title compound as a white solid.

$^1$H NMR (400 MHz, CDCl$_3$): δ 1.60-2.00 (m), 2.20 (s, 3H), 2.40-2.80 (m, 5H), 3.10 (m, 2H), 7.10 (d, 2H), 7.55 (d, 2H); LCMS: m/z APCI$^+$, 277 [MH]$^+$

Preparation 2b: 4-[4-(4-Chlorophenyl)-5-methyl-4H-1,2,4-triazol-3-yl]piperidine hydrochloride

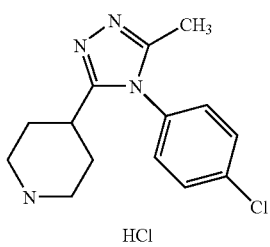

Hydrochloric acid in dioxan (4M, 10 mL) was added to a cooled (5° C.) solution of the compound of preparation 1 (1.32 g, 4.76 mmol) in methanol (30 mL), and the solution was allowed to warm to room temperature with stirring for a further 90 minutes. Tlc analysis showed that starting material remained, so additional hydrochloric acid in dioxan (4M, 10 mL) was added and the reaction was stirred for a further 4 hours. The mixture was concentrated under reduced pressure and the residue was azeotroped with toluene (3×) to afford the title compound, 1.4 g.

$^1$H NMR (400 MHz, DMSO-d$_6$): δ 1.86 (m, 4H), 2.25 (m, 3H), 2.80-2.97 (m, 3H), 3.22 (m, 2H), 7.64 (m, 2H), 7.77 (d, 2H).

Preparation 3: 1-(3-Chloro-benzoyl)-piperidine-4-carboxylic acid ethyl ester

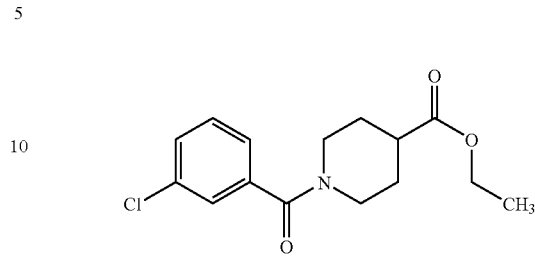

A solution of ethyl isonipecotate (27.6 g, 175 mmol) in dichloromethane (50 ml) was added dropwise over 10 minutes to a solution of 3-chlorobenzoyl chloride (20 ml, 160 mmol) and triethylamine (28 ml, 200 mmol) in dichloromethane (500 ml) cooled to between 10 and 15° C. The reaction was then stirred at room temperature for 3 hours and concentrated under reduced pressure. The residue was diluted with ether, the solution washed with 1N hydrochloric acid, sodium carbonate solution (×3) and brine. It was then dried over MgSO$_4$ and evaporated under reduced pressure, to give the title compound as a solid, 44.49.

$^1$H NMR (400 MHz, CDCl$_3$): δ 1.24 (t, 3H), 1.62-2.10 (m, 4H), 2.58 (m, 1H), 2.98-3.16 (m, 2H), 3.70 (m, 1H), 4.15 (q, 2H), 4.49 (m, 1H), 7.24 (m, 1H), 7.31-7.40 (m, 3H). LRMS: m/z (APCI$^+$) 296 [MH]$^+$

Preparation 4: 1-(3-Chloro-benzoyl)-piperidine-4-carboxylic acid hydrazide

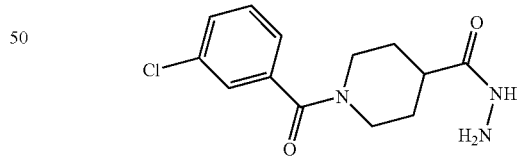

A mixture of the ester of preparation 3 (44.4 g, 0.15 mol) and hydrazine hydrate (30 ml, 0.58 mol) in methanol (120 ml) was heated under reflux for 10 hours, and then allowed to cool to room temperature. The mixture was concentrated under reduced pressure and the product crystallised from ethyl acetate/ether to afford the title compound as a solid, 32.5 g.

$^1$H NMR (400 MHz, CDCl$_3$): δ 1.62-1.98 (m, 4H), 2.36 (m, 1H), 2.78-3.09 (m, 2H), 3.64-4.00 (m, 2H), 4.65 (m, 1H), 7.04 (m, 1H), 7.26 (m, 1H), 7.36 (m, 3H). LRMS: m/z (APCI$^+$) 282 [MH]$^+$

Preparation 5: 1-(3-Chloro-benzoyl)-piperidine-4-carboxylic acid N'-(2-chloro-acetyl)-hydrazide

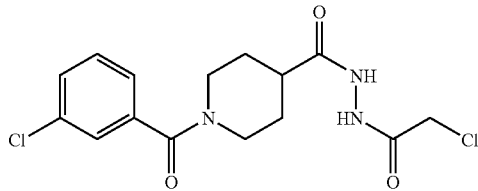

Chloroacetyl chloride (4.3 ml, 53 mmol) was added dropwise, over 30 minutes, to an ice-cooled solution of the hydrazide of preparation 4 (10 g, 35.5 mmol) and N-methyl morpholine (5.4 g, 53 mmol) in dichloromethane (200 ml), in order to maintain the internal temperature below 10° C. The reaction mixture was then allowed to warm to room temperature and was stirred for a further 18 hours. The reaction was diluted with ethyl acetate, washed with saturated sodium bicarbonate solution, and then brine. The solution was dried over MgSO$_4$, concentrated under reduced pressure and the residue was triturated with ether to afford the title compound as a white solid, 10.2 g.

$^1$H NMR (400 MHz, CD$_3$OD): δ 1.66-1.84 (m, 3H), 1.98 (m, 1H), 2.61 (m, 1H), 2.99 (m, 1H), 3.19 (m, 1H), 3.74 (m, 1H), 4.14 (s, 2H), 4.60 (m, 1H), 7.35 (dd, 1H), 7.46 (m, 3H). LRMS: m/z (ES$^+$) 358 [MH]$^+$

Preparation 6: [4-(5-Chloromethyl-[1,3,4]oxadiazol-2-yl)-piperidin-1-yl]-(3-chloro-phenyl)-methanone

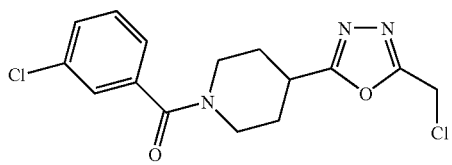

Trifluoroacetic anhydride (9.45 ml, 57 mmol) was added dropwise over 30 minutes to a cooled solution (0 to 5° C.) of the compound of preparation 5 (10.2 g, 28.5 mmol) and pyridine (11.5 ml, 142.5 mmol) in dichloromethane (300 ml). Once the addition was complete, the resulting pink suspension was stirred for a further 90 minutes at 10° C. The reaction mixture was poured carefully into saturated sodium bicarbonate solution (600 ml), and the layers were separated. The organic phase was washed with further saturated sodium bicarbonate solution (×2), dried over MgSO$_4$, and treated with decolourising charcoal. The mixture was then filtered and the filtrate evaporated under reduced pressure to afford the title compound, 13 g.

$^1$H NMR (400 MHz, CD$_3$OD): δ 1.80-1.97 (m, 2H), 2.08 (m, 1H), 2.22 (m, 1H), 3.15-3.40 (m, 3H), 3.76 (m, 1H), 4.56 (m, 1H), 4.84 (s, 2H), 7.37 (m, 1H), 7.48 (m, 3H). LRMS: m/z (APCI$^+$) 340 [MH]$^+$

Preparation 7: 4-[N'-(2-Chloro-acetyl)-hydrazinocarbonyl]-piperidine-1-carboxylic acid tert-butyl ester

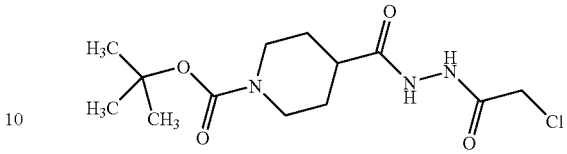

4-Hydrazinocarbonyl-piperidine-1-carboxylic acid tert-butyl ester (see reference WO 2000039125, prep 27)(25 g, 103 mmol) was dissolved in dichloromethane (300 ml) and 4-methylmorpholine (12.5 ml, 113 mmol) was then added. The mixture was cooled using an ice bath and chloroacetyl chloride (8.2 ml, 103 mmol) was added dropwise. The reaction was then allowed to warm to room temperature and was stirred for 4 hours. The reaction mixture was partitioned with aqueous sodium hydrogen carbonate solution, dried over magnesium sulphate, filtered and the filtrate was evaporated to give the title compound as an off white solid (29.6 g).

LRMS m/z APCI$^-$ 318 [M-H]$^-$

Preparation 8: 4-(5-Chloromethyl-[1,3,4]oxadiazol-2-yl)-piperidine-1-carboxylic acid tert-butyl ester

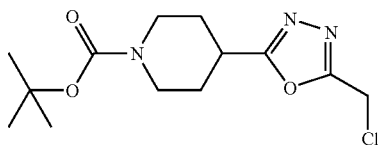

The hydrazide of preparation 7 (5.0 g, 15.6 mmol) was suspended in dichloromethane (200 ml) and then pyridine (6.4 ml, 78 mmol) was added before cooling the mixture to 10° C. Trifluoroacetic anhydride (6.6 ml, 39 mmol) was added dropwise over 15 minutes and then the mixture was stirred at room temperature for 3 hours. The reaction was then partitioned with water (50 ml), the organic layer was dried over magnesium sulphate, filtered and the filtrate was evaporated under reduced pressure. The residue was purified by chromatography on silica gel using methanol in dichloromethane as eluant (2:98) to afford the title compound as a white solid (2.95 g).

$^1$H NMR (400 MHz, CD$_3$OD): δ 1.45 (s, 9H), 1.74 (m, 2H), 2.19 (m, 2H), 3.04 (m, 2H), 3.24 (m, 1H), 4.09 (m, 2H), 4.85 (s, 2H)

Preparation 9a: 4-(5-[1,2,3]Triazol-2-ylmethyl-[1,3,4]oxadiazol-2-yl)-piperidine-1-carboxylic acid tert-butyl ester and

4-(5-[1,2,3]Triazol-1-ylmethyl-[1,3,4]oxadiazol-2-yl)-piperidine-1-carboxylic acid tert-butyl ester

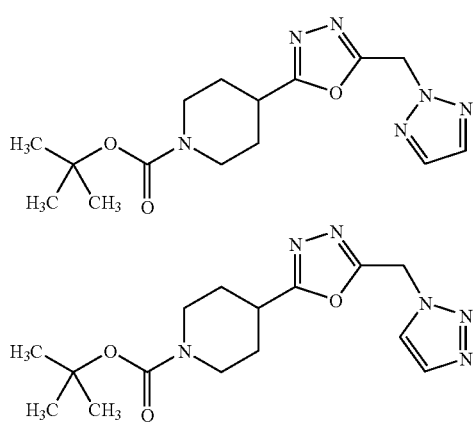

A mixture of the compound of preparation 8 (8 g, 26.5 mmol), triazole (3.7 g, 53 mmol) and potassium carbonate (5.2 g, 38 mmol) in N,N-dimethylformamide (60 ml) was stirred at room temperature for 18 hours. The mixture was then filtered, and the filtrate was concentrated under reduced pressure. The residue was partitioned between ethyl acetate and brine, the layers were separated and the organic solution was dried over $MgSO_4$ and concentrated under reduced pressure to afford the title compounds as a mixture of isomers.

$^1$H NMR (400 MHz, $CD_3OD$): δ 1.43 (s, 9H), 1.62-1.78 (m, 2H), 2.02 (m, 2H), 3.00 (m, 2H), 3.19 (m, 1H), 4.03 (m, 2H), 5.95, 5.99 (2×s, 2H), [7.77 (s), 7.80 (d), 8.18 (s) total 2H].

Preparation 9b: 4-(5-[1,2,3]Triazol-2-ylmethyl-[1,3,4]oxadiazol-2-yl)-piperidine-1-carboxylic acid tert-butyl ester Dichloromethane (500 mL) was added to a suspension of the hydrazide of preparation 170 (132.3 g, 375 mmol) in 1-methylimidazole (120 mL), and the resulting solution was cooled in an ice/acetone-bath. Triflic anhydride (92 mL, 561 mmol) was added dropwise over 2.5 hours, in order to maintain the reaction temperature below 0° C. Once the addition was complete, the reaction was stirred for a further 20 minutes. It was then quenched by the addition of 2M hydrochloric acid (350 mL). The phases were separated and the aqueous layer was extracted with dichloromethane (200 mL). The combined organic solutions were washed with brine, dried over $MgSO_4$ and evaporated under reduced pressure. The residue was purified by column chromatography on silica gel using dichloromethane as eluant to afford the title compound as a viscous oil.

Preparation 10: (3-Chloro-phenyl)-[4-(5-[1,2,3]triazol-2-ylmethyl-[1,3,4]oxadiazol-2-yl)-piperidin-1-yl]-methanone

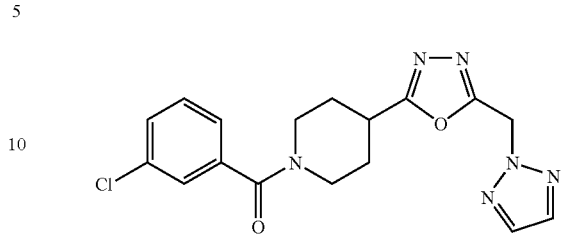

A mixture of the compound of preparation 6 (2 g, 5.9 mmol), triazole (810 mg, 11.75 mmol) and potassium carbonate (1.2 g, 8.85 mmol) in acetonitrile (20 ml) was stirred at room temperature for 30 minutes, followed by a further hour at 50° C. The reaction mixture was filtered, washed through with ethyl acetate and the filtrate was concentrated under reduced pressure. The residual brown oil was partitioned between ethyl acetate and water, the layers were separated, and the organic phase was washed with additional water, then brine. The solution was dried over $MgSO_4$ and evaporated under reduced pressure. The crude product was purified by column chromatography on silica gel using dichloromethane:methanol (100:0 to 95:5) to afford the title compound, (202 mg).

$^1$H NMR (400 MHz, $CD_3OD$): δ 1.76-1.90 (m, 2H), 2.02 (m, 1H), 2.18 (m, 1H), 3.12-3.38 (m, 3H), 3.72 (m, 1H), 4.50 (m, 1H), 5.97 (s, 2H), 7.37 (dd, 1H), 7.41-7.51 (m, 3H), 7.78 (s, 2H). LRMS: m/z ($ES^+$) 373, 375 $[MH]^+$

Preparation 11a: 4-[4-(4-Chloro-phenyl)-5-[1,2,3]triazol-2-ylmethyl-4H-[1,2,4]triazol-3-yl]-piperidine-1-carboxylic acid tert-butyl ester

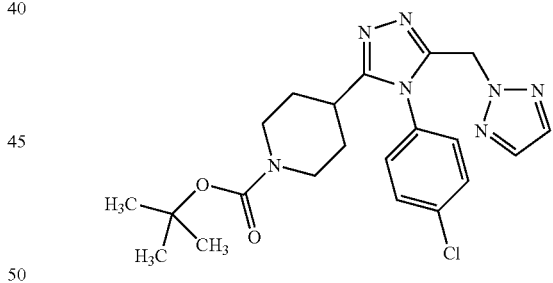

Trifluoroacetic acid (1 ml, 13.2 mmol) was added to a solution of the compounds of preparation 9a (8.8 g, 26.5 mmol) and 4-chloroaniline (5 g, 39.75 mmol) in toluene (200 ml) and the reaction mixture was stirred at reflux for 5 hours. The cooled mixture was diluted with dichloromethane, then washed with 1N sodium hydroxide solution and brine, and evaporated under reduced pressure. The residual brown oil was purified by column chromatography on silica gel using an elution gradient of dichloromethane:methanol:0.88 ammonia (100:0:0 to 90:10:1) and then re-columned using ethyl acetate:methanol:0.88 ammonia (100:0:0 to 90:10:1) to afford the title compound, (2.3 g).

$^1$H NMR (400 MHz, $CD_3OD$): δ 1.42 (s, 9H), 1.68-1.82 (m, 4H), 2.62-2.78 (m, 3H), 4.08 (m, 2H), 5.70 (s, 2H), 7.24 (d, 2H), 7.56 (d, 2H), 7.59 (s, 2H); LRMS: m/z ($APCI^+$) 444 $[MH]^+$

Preparation 11b: 4-[4-(4-chloro-phenyl)-5-[1,2,3]triazol-2-ylmethyl-4H-[1,2,4]triazol-3-yl]-piperidine-1-carboxylic acid tert-butyl ester N-Methylimidazole (4.66 g, 56.75 mmol) and dichloromethane (20 ml) were added to the bis-acyl hydrazide from preparation 170 (5.00 g, 14.19 mmol), and the resulting solution was cooled to −20° C. Trifluoromethanesulfonic acid anhydride (6.00 g, 21.28 mmol) was added, keeping the temperature below 0° C. Upon completion of the addition, the reaction was warmed to ambient temperature and stirred for 15 hours. The reaction was quenched with H₂O (10 ml), the phases were separated and the aqueous layer was re-extracted with dichloromethane (10 ml). The combined organic phases were dried over magnesium sulphate, filtered, and the dichloromethane was distilled and replaced with toluene under vacuum to give a toluene solution of the intermediate oxadiazole (~20 ml volume). 4-Chloroaniline (1.90 g, 14.90 mmol) was added to the toluene solution followed by trifluoroacetic acid (0.81 g, 7.09 mmol) and the reaction was stirred at 85° C. for 5.5 hours. The mixture was cooled to ambient temperature and stirred with 1.8N aqueous ammonia (14 ml) for 5 minutes. The phases were separated, the organic phase was diluted with tert-butyl methyl ether (20 ml) and then stirred for 15 hours. The resulting solid precipitate was collected by filtration, washing with tert-butyl methyl ether (2×5 ml), to give the title compound as a beige coloured solid (2.72 g). ¹H NMR (400 MHz, CDCl₃): δ 1.43 (s, 9H), 1.72 (d, 2H), 1.85 (bm, 2H), 2.56 (m, 1H), 2.66 (bm, 2H), 4.09 (bd, 2H), 5.64 (s, 2H), 7.01 (d, 2H), 7.43 (d, 2H), 7.50 (s, 2H).

Preparation 12a: 4-[4-(4-Chloro-phenyl)-5-[1,2,3]triazol-2-ylmethyl-4H-[1,2,4]triazol-3-yl]-piperidine

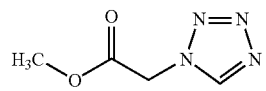

4M Hydrochloric acid in dioxan (10 ml) was added to a solution of the compound of preparation 11a (2.3 g, 5.2 mmol) in methanol (30 ml), and the reaction was stirred at room temperature for 2 hours. The solution was concentrated under reduced pressure, the residue was diluted with dichloromethane and basified with 1N sodium hydroxide solution to pH 10, and the layers were separated. The aqueous phase was re-extracted with dichloromethane and the combined organic solutions were dried over MgSO₄ and concentrated under reduced pressure to afford the title compound as a foam, (1.65 g).

¹H NMR (400 MHz, CD₃OD): δ 1.79 (m, 4H), 2.48 (m, 2H), 2.65 (m, 1H), 3.02 (m, 2H), 5.70 (s, 2H), 7.22 (d, 2H), 7.55 (d, 2H), 7.59 (s, 2H); LRMS: m/z (APCI⁺) 344 [MH]⁺

Preparation 12b: 4-[4-(4-Chloro-phenyl)-5-[1,2,3]triazol-2-ylmethyl-4H-[1,2,4]triazol-3-yl]-piperidine bis p-toluenesulfonate salt

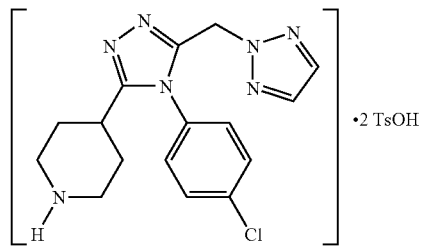

Ethyl acetate (30 ml) was added to a mixture of the compound from preparation 11b (6.5 g, 14.6 mmol) and p-toluenesulfonic acid monohydrate (8.4 g, 44.2 mmol) and the reaction was stirred at room temperature for 17 hours. The solid precipitate was collected by filtration, washing with ethyl acetate (20 ml) to give the title compound as a white solid, (9.32 g).

¹H NMR (400 MHz, DMSO-d₆): δ 1.85 (m, 4H), 2.26 (s, 6H), 2.83 (m, 3H), 3.24 (m, 2H), 5.68 (s, 2H), 7.10 (d, 4H), 7.32 (d, 2H), 7.47 (d, 4H), 7.54 (d, 2H), 7.65 (s, 2H), 8.29 (m, 1H), 8.49 (m, 1H).

LRMS: m/z (APCI⁺) 344 [MH]⁺

Preparation 13: Methyl 1H-tetrazol-1-ylacetate

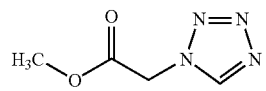

A mixture of tetrazol-1-yl acetic acid (5 g, 39 mmol) and 4M hydrochloric acid in dioxan (100 μL) in methanol (50 mL) was heated under reflux for 18 hours. The cooled mixture was evaporated under reduced pressure to provide the title compound.

¹H NMR (400 MHz, DMSO-d₆): δ 3.74 (s, 3H), 5.58 (s, 2H), 9.39 (s, 1H); LCMS: m/z APCI⁺143 [MH]⁺

Preparation 14: (3-Methyl-isoxazol-5-yl)-acetoyl chloride

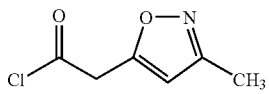

N,N-Dimethylformamide (few drops), followed by oxalyl chloride (9.5 mL, 106 mmol) were added dropwise to a cooled (10° C.) solution of (3-methyl-isoxazol-5-yl)-acetic acid (5 g, 35.4 mmol) in dichloromethane (50 mL), and the solution was allowed to warm to room temperature. The reaction was stirred for a further 3 hours, then concentrated under reduced pressure. The residue was azeotroped with toluene to afford the title compound.

¹H NMR (400 MHz, CDCl₃): δ 2.30 (s, 3H), 4.32 (s, 2H), 6.18 (s, 1H).

Preparation 15: Ethyl (2-methyl-1H-imidazol-1-yl)acetate

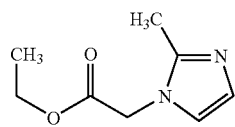

Potassium carbonate (8.42 g, 61 mmol) was added to a solution of 2-methylimidazole (5 g, 61 mmol) in tetrahydrofuran (100 mL) and the suspension was stirred for 30 minutes. Ethyl bromoacetate (6.75 mL, 61 mmol) was added and the reaction was stirred for a further 30 minutes at room temperature. The mixture was filtered, washing through with dichloromethane:methanol (90:10). The filtrate was evaporated under reduced pressure and the crude product was purified by column chromatography on silica gel using dichloromethane: methanol:0.88 ammonia (93:7:0.5) as eluant to afford the title compound as an oil, 5.28 g.

¹H NMR (400 MHz, CDCl₃): δ 1.26 (t, 3H), 2.35 (s, 3H), 4.22 (q, 2H), 4.58 (s, 2H), 6.81 (s, 1H), 6.94 (s, 1H). LCMS: m/z APCI⁺169 [MH]⁺

Preparation 16: 2-(1H-Tetrazol-1-yl)acetohydrazide

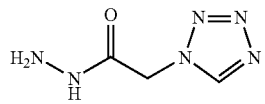

Hydrazine hydrate (3.2 g, 63 mmol) was added to a solution of the ester of preparation 13 (3 g, 21.1 mmol) in methanol (18 mL) and the mixture was heated under reflux for 18 hours. The cooled reaction was concentrated under reduced pressure and the residue was azeotroped with toluene to afford the title compound.

¹H NMR (400 MHz, DMSO-d₆): δ 5.18 (s, 2H), 9.38 (s, 1H). LCMS: m/z APCI⁺ 143 [MH]⁺

Preparation 17: [1,2,3]Triazol-1-yl-acetic acid ethyl ester and [1,2,3]triazol-2-yl-acetic acid ethyl ester

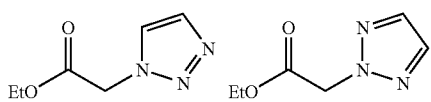

1,2,3-Triazole (19.00 kg, 275 mol) was charged over 30 minutes to a suspension of potassium carbonate (42.15 kg, 305 mol) in ethanol (80 L), and was rinsed in with ethanol (2 L). A solution of ethyl bromoacetate (45.8 kg, 274 mol) in ethanol (30 L) was added slowly and was rinsed in with ethanol (2 L). During this time the reaction temperature was maintained at <20° C. The reaction mixture was then warmed to room temperature and stirred overnight. The suspension was filtered; washing the residue with ethanol (25 L and 17 L) and then the filtrate was concentrated under reduced pressure. The concentrate was dissolved in ethyl acetate (120 L) and the solution was washed with 1N hydrochloric acid (1×40 L, 7×20 L, 4×15 L). The aqueous washings were combined and extracted with ethyl acetate (3×21 L). The organic phases were combined, dried over magnesium sulphate, filtered and concentrated to dryness giving a mixture of the title compounds (25 kg). ¹H NMR spectroscopic analysis indicated that this was a 6:5 mixture of N-2/N-1 isomers.

¹H NMR (400 MHz, CDCl₃): δ 1.25 (m, 3H), 4.13 (q, 2H, N-1 isomer), 4.25 (q, 2H, N-2 isomer), 5.20 (s, 2H, N-1 isomer), 5.22 (s, 2H, N-2 isomer), 7.70 (s, 2H, N-2 isomer), 7.77 (s, 2H, N-1 isomer).

Preparation 18: [1,2,3]Triazol-2-yl-acetic acid hydrazide

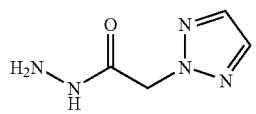

Hydrazine hydrate (8.65 kg, 270 mol) was added to a cooled (<10° C.) solution of the mixture of esters of preparation 17 (19 kg) in ethanol (69 L) keeping the temperature below 20° C. throughout the addition. The reaction mixture was stirred at between 14 and 19° C. for 3 hours, then more ethanol (25 L) was added and the product was collected by filtration, washing with ethanol (10 L). The crude solid was purified by recrystallisation from ethanol (120 L), followed by three recrystallisations from methanol (105 L, 120 L and 90 L) to give the title compound, (4.53 kg) after drying in vacuo.

¹H NMR (400 MHz, DMSO-d₆): δ 4.33 (s, 2H), 5.02 (s, 2H), 7.77 (s, 2H), 9.40 (s, 1H).

Preparation 19: 2-(2-Methyl-1H-imidazol-1-yl)acetohydrazide

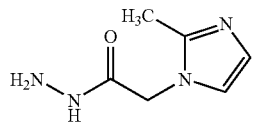

The title compound was obtained as a white solid from the compound of preparation 15 and hydrazine following a similar procedure to that described for preparation 16, except that 5 equivalents of hydrazine were used, and isopropanol was used as the reaction solvent.

¹H NMR (400 MHz, CD₃OD): δ 2.35 (s, 3H), 4.60 (s, 2H), 6.81 (s, 1H), 6.99 (s, 1H).

LCMS: m/z APCI⁺ 155 [MH]⁺

Preparation 20: 2-(3-Methyl-1,2,4-oxadiazol-5-yl)acetohydrazide

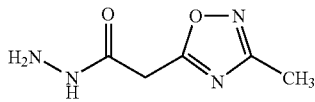

The title compound was obtained from 3-methyl 1,2,4-oxadiazol-5-yl-acetic acid methyl ester (NL 7807076) and hydrazine following a similar procedure to that described for preparation 16, except that 8 equivalents of hydrazine were used, and isopropanol was used as the reaction solvent.

$^1$H NMR (400 MHz, CDCl$_3$): δ 2.42 (s, 3H), 3.86 (s, 2H), 6.89 (br s, 1H), 8.18 (br s, 1H).

Preparation 21: 2-(Pyrimidin-2-yloxy)acetohydrazide

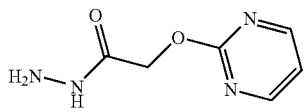

A mixture of ethyl 2-pyrimidinyloxyacetate (GB2373186, step i ex 368) (4.4 g, 24.15 mmol) and hydrazine hydrate (5 mL, 160 mmol) in isopropanol (30 mL) was heated under reflux for 1 hour. The mixture was then cooled and concentrated under reduced pressure and the residue was purified by column chromatography on silica gel using dichloromethane:methanol:0.88 ammonia (100:0:0 to 100:10:1) to provide the title compound, 600 mg.

$^1$H NMR (400 MHz, CDCl$_3$): δ 4.98 (s, 3H), 7.04 (m, 1H), 8.58 (d, 2H); LCMS: m/z APCI$^+$ 169 [MH]$^+$

Preparation 22: tert-Butyl 2-[(3-methylisoxazol-5-yl)acetyl]hydrazinecarboxylate

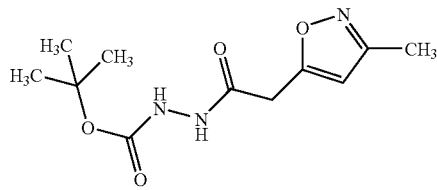

Triethylamine (24 mL, 17 mmol) was added slowly to a cooled (10° C.) solution of the acid chloride of preparation 14 (5.64 g, 35.4 mmol) in dichloromethane (200 mL), followed by tert-butyl carbazate (5.6 g, 42.5 mmol) and the reaction was stirred at room temperature for 18 hours. The reaction was diluted with ethyl acetate and the precipitate was filtered off. The filtrate was concentrated under reduced pressure and the residue was purified by column chromatography on silica gel using an elution gradient of ethyl acetate:pentane (50:50 to 100:0) to provide the title compound.

$^1$H NMR (400 MHz, CDCl$_3$): δ 1.47 (s, 9H), 2.30 (s, 3H), 3.77 (s, 2H), 6.15 (s, 1H), 6.45 (br s, 1H), 7.59 (br s, 1H).

Preparation 23: tert-Butyl 2-[3-(3,5-dimethylisoxazol-4-yl)propanoyl]hydrazinecarboxylate

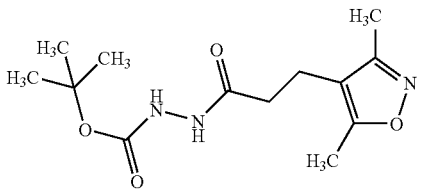

Oxalyl chloride (5.16 mL, 59.2 mmol) was added to a solution of β-(3,5-dimethyl-4-isoxazolyl)propionic acid (J. Org. Chem. 59(10); 1994; 2882) (2.5 g, 14.8 mmol) in dichloromethane (50 mL) and N,N-dimethylformamide (1 drop), and the solution was stirred at room temperature for 30 minutes. The mixture was concentrated under reduced pressure and the residue was azeotroped with dichloromethane (5×) to provide a brown liquid. This was dissolved in dichloromethane (25 mL), and tert-butyl carbazate (2.93 g, 22.2 mmol) was added portionwise. The mixture was diluted with further dichloromethane (23 mL) and the reaction was stirred for 18 hours at room temperature. The mixture was concentrated under reduced pressure, the residue was suspended in dichloromethane, the resulting precipitate was filtered off and the filtrate was evaporated under reduced pressure. The residue was purified by column chromatography on silica gel using an elution gradient of dichloromethane:methanol:0.88 ammonia (95:5:0.5 to 90:10:1) to provide the title compound as an oil, 3.08 g.

$^1$H NMR (400 MHz, CDCl$_3$): δ 1.45 (s, 9H), 2.21 (s, 3H), 2.36 (m, 4H), 2.45 (m, 1H), 2.60-2.73 (m, 2H), 6.48 (br s, 1H), 7.42 (br s, 1H). LCMS: m/z ES$^+$ 306 [MNa]$^+$

Preparation 24: 2-(3-Methylisoxazol-5-yl)acetohydrazide hydrochloride

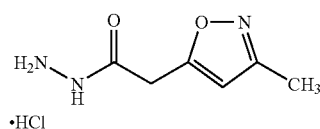

A mixture of the compound of preparation 22 (1.6 g, 6.3 mmol) in 4M hydrochloric acid in dioxan (20 mL) and methanol (60 mL) was stirred at room temperature for 3 hours. The solution was concentrated under reduced pressure to low volume, the resulting precipitate was filtered off, washed with dichloromethane and dried to afford the title compound, 810 mg.

$^1$H NMR (400 MHz, DMSO-d$_6$): δ 2.20 (s, 3H), 3.86 (s, 2H), 6.24 (s, 1H).

LCMS: m/z APCI$^+$ 156 [MH]$^+$

Preparation 25: 3-(3,5-Dimethylisoxazol-4-yl)propanohydrazide hydrochloride

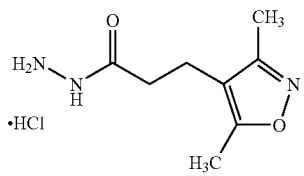

A solution of the compound of preparation 23 (3.08 g, 10.87 mmol) in 2.2M methanolic hydrochloric acid (50 mL) was stirred at room temperature for 18 hours. The solution was concentrated under reduced pressure and the residue was azeotroped with toluene. The crude product was triturated with pentane/ether and then ether, and the resulting solid was filtered off to provide the title compound as an off-white solid, 1.39 g.

$^1$H NMR (400 MHz, DMSO-$d_6$): δ 2.22 (s, 3H), 2.27 (t, 2H), 3.35 (s, 3H), 2.66 (t, 2H), 6.75 (br s, 1H). LCMS: m/z APCI$^+$ 184 [MH]$^+$

Preparation 26: tert-Butyl 2-(hydrazinocarbonyl)morpholine-4-carboxylate

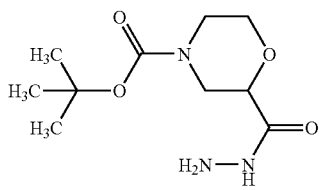

A mixture of 4-(tert-butyl) 2-methyl 2,4-morpholinecarboxylate (WO 03/018576, ex 1 part i) (2.03 g, 8.3 mmol), hydrazine hydrate (1.2 mL, 24 mmol) and methanol (50 mL) was heated under reflux for 4 days. The cooled mixture was evaporated under reduced pressure, the residue was partitioned between water and ethyl acetate, and the layers were separated. The organic phase was dried over MgSO$_4$ and evaporated under reduced pressure to provide the title compound, 1.92 g.

LCMS: m/z ES$^+$ 268 [MNa]$^+$

Preparation 27: tert-Butyl 3-(hydrazinocarbonyl)piperidine-1-carboxylate

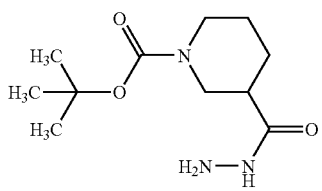

Hydrazine hydrate (75 mL, 1.5 mol) was added to a solution of piperidine-1-3-dicarboxylic acid 1 tert-butyl 3-ethyl ester (U.S. 2002 0099035, ex 12) (72 g, 280 mmol) in ethanol (250 mL) and the reaction was heated under reflux for 18 hours. The cooled mixture was concentrated under reduced pressure and the residue was partitioned between dichloromethane and water, and the layers were then separated. The aqueous phase was extracted with dichloromethane, and the combined organic solutions were dried over MgSO$_4$ and evaporated under reduced pressure. The product was azeotroped with ether to afford the title compound as a colourless gum, 59.8 g.

$^1$H NMR (400 MHz, CDCl$_3$): δ 1.40-1.50 (m, 11H), 1.63 (m, 1H), 1.83 (m, 2H), 2.25 (m, 1H), 2.97 (m, 1H), 3.16 (m, 1H), 3.78-3.98 (m, 3H), 7.40-7.60 (br s, 1H).

Preparation 28: Ethyl 1-(4-chlorobenzoyl)piperidine-4-carboxylate

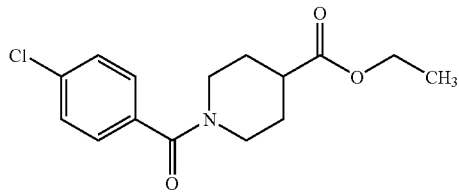

The title compound was obtained as a yellow oil from ethyl isonipecotate and 4-chlorobenzoyl chloride, following a similar procedure to that described for preparation 3.

$^1$H NMR. (400 MHz, CDCl$_3$): δ 1.24 (t, 3H), 1.62-2.06 (m, 4H), 2.59 (m, 1H), 3.03 (m, 2H), 3.72 (m, 1H), 4.17 (q, 2H), 4.54 (m, 1H), 7.36 (d, 2H), 7.39 (d, 2H). LCMS: m/z APCI$^+$ 296 [MH]$^+$

Preparation 29: 1-(4-Chlorobenzoyl)piperidine-4-carbohydrazide

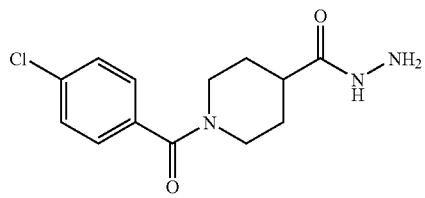

A solution of the compound of preparation 28 (148 g, 0.5 mol) in methanol (400 mL) was heated at 70° C. for 30 minutes. Hydrazine hydrate (50 g, 1.0 mol) was then added and the reaction was stirred at 60° C. for a further 3 hours. Tlc analysis showed that starting material remained, so additional hydrazine hydrate (50 mL, 1.0 mol) was added and the reaction was stirred for a further 48 hours at 75° C. The cooled mixture was concentrated under reduced pressure, the residue was suspended in dichloromethane (1 L) and washed with water (2×). The organic solution was dried over MgSO$_4$ and evaporated under reduced pressure to afford the title compound as a white solid, 119 g.

$^1$H NMR (400 MHz, CDCl$_3$): δ 1.65-1.94 (m, 4H), 2.35 (m, 1H), 2.80-3.06 (m, 2H), 3.79 (m, 1H), 4.65 (m, 1H), 7.10 (s, 1H), 7.38 (m, 4H). LCMS: m/z APCI$^+$ 282 [MH]$^+$

Preparation 30: 1-(4-Chlorobenzoyl)-N'-(trifluoroacetyl)piperidine-4-carbohydrazide

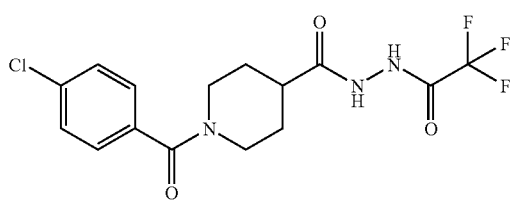

Trifluoroacetic anhydride (1.56 mL, 11.18 mmol) was added dropwise to an ice-cooled solution of the compound of preparation 29 (3.0 g, 10.65 mmol) and N-methylmorpholine (1.29 mL, 11.7 mmol) in dichloromethane (50 mL), and the reaction was stirred at room temperature for 18 hours. The resulting precipitate was filtered off, washed with dichloromethane and dried to afford the title compound, 1.78 g.

$^1$H NMR (400 MHz, DMSO-d$_6$): δ 1.56 (m, 2H), 1.64-1.84 (m, 2H), 2.56 (m, 1H), 2.85 (m, 1H), 3.08 (m, 1H), 3.58 (m, 1H), 4.40 (m, 1H), 7.40 (d, 2H), 7.50 (d, 2H), 10.20 (s, 1H), 11.15 (br s, 1H).

Preparation 31: 1-(4-Chlorobenzoyl)-N-(ethoxyacetyl)piperidine-4-carbohydrazide

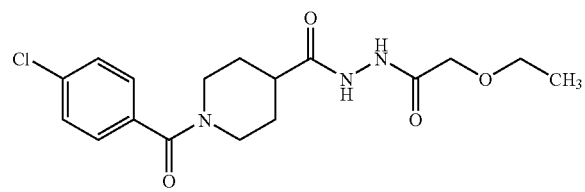

N-Methylmorpholine (2.60 g, 26.6 mmol), and then ethoxyacetyl chloride (WO 01/46150 ex 33A) (1.09 g, 8.87 mmol) were added to a solution of the compound of preparation 29 (2.5 g, 8.87 mmol) in dichloromethane (70 mL), and the reaction was stirred at room temperature for 18 hours. The mixture was washed with water, then ammonium chloride solution and finally sodium carbonate solution. It was dried over MgSO$_4$ and evaporated under reduced pressure to afford the title compound.

$^1$H NMR (400 MHz, CDCl$_3$): δ 1.22 (t, 3H), 1.72-1.99 (m, 4H), 2.56 (m, 1H), 2.86-3.06 (m, 2H), 3.60 (q, 2H), 3.80 (m, 1H), 4.04 (s, 2H), 4.62 (m, 1H), 7.38 (m, 4H), 8.90 (d, 1H), 8.99 (d, 1H). LCMS: m/z ES$^+$ 368, 370 [MH]$^+$

Preparation 32: 1-(3-Chlorobenzoyl)-N'-(ethoxyacetyl)piperidine-4-carbohydrazide

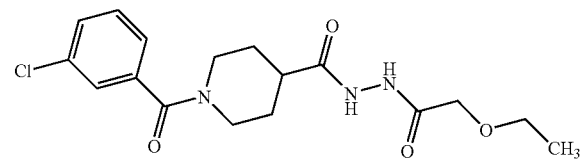

The title compound was obtained in 91% yield from the compound of preparation 4 and ethoxyacetyl chloride (WO 01/46150 ex 33A) following the procedure described for preparation 31.

$^1$H NMR (400 MHz, CDCl$_3$): δ 1.22 (t, 3H), 1.72-2.00 (m, 4H), 2.56 (m, 1H), 2.84-3.10 (m, 2H), 3.60 (q, 2H), 3.79 (m, 1H), 4.04 (s, 2H), 4.62 (m, 1H), 7.26 (m, 1H), 7.38 (m, 3H), 8.61 (d, 1H), 8.75 (d, 1H). LCMS: m/z APCI$^+$ 368, 370 [MH]$^+$

Preparation 33: tert-Butyl 4-{[(4-chlorophenyl)amino]carbonyl}piperidine-1-carboxylate

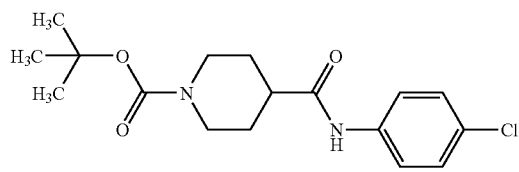

1-BOC-piperidine-4-carboxylic acid (100 g, 437 mmol), 4-chloroaniline (61.2 g, 480 mmol), 1-(3-dimethylaminopropyl)-3-ethylcarbodiimide hydrochloride (100 g, 524 mmol) and triethylamine (182.6 mL, 1.31 mol) were dissolved in cold (10° C.) acetonitrile (1.75 L). The reaction mixture was stirred for 54 hours at room temperature and then concentrated under reduced pressure. The residue was dissolved in ethyl acetate and then partitioned with 2N hydrochloric acid. The resulting precipitate was filtered off, re-dissolved in dichloromethane, the solution was dried over MgSO$_4$ and evaporated under reduced pressure. The residue was triturated with ether to afford the desired compound as a white solid.

The filtrate was separated and the organic layer was washed with 2N hydrochloric acid (2×), dried over MgSO$_4$ and evaporated under reduced pressure. The solid was triturated with ether to afford further compound as a white solid, combined yield 99.4 g.

$^1$H NMR (400 MHz, CDCl$_3$): δ 1.46 (s, 9H), 1.68-1.80 (m, 2H), 1.90 (m, 2H), 2.39 (m, 1H), 2.79 (m, 2H), 4.19 (m, 2H), 7.10 (s, 1H), 7.26 (d, 2H), 7.46 (d, 2H). LCMS: m/z APCI$^+$ 339 [MH]$^+$

Preparation 34: tert-Butyl 4-{[(4-chlorophenyl)amino]carbonothioyl}piperidine-1-carboxylate

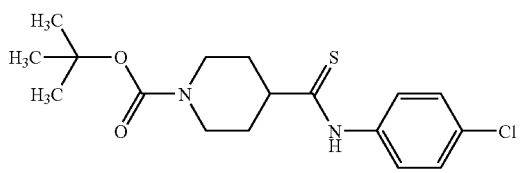

A solution of the compound of preparation 33 (99.4 g, 294 mmoL) and Lawesson's reagent (30 g, 74.3 mmol) in toluene (1 L) was heated under reflux for 1 hour, then stirred at room temperature for a further 18 hours. Tlc analysis showed that starting material remained, so additional Lawesson's reagent (11.1 mmol) was added and the reaction was heated under reflux for a further hour. The cooled mixture was concentrated under reduced pressure and the residue was azeotroped with ethyl acetate. The crude product was triturated with hot ethyl acetate, the resulting solid was filtered off and dried to afford the title compound as a white solid, 53 g.

LCMS: m/z APCI$^-$ 353 [M-H]$^-$

Preparation 35: Ethyl 1-{[(4-chlorophenyl)amino]carbonothioyl}piperidine-4-carboxylate

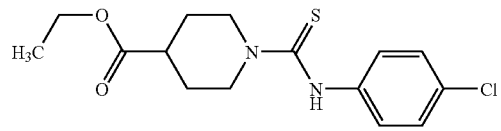

A mixture of 4-chlorophenyl isothiocyanate (3.5 g, 20.7 mmol), and ethyl isonipecotate (3.19 mL, 20.7 mmol) in dichloromethane (30 mL) was stirred at room temperature for 1 hour. The mixture was concentrated under reduced pressure, the residue was triturated with ether and the resulting solid was filtered off and dried to afford the title compound as a white solid, 6.27 g.

$^1$H NMR (400 MHz, CDCl$_3$): δ 1.24 (t, 3H), 1.82 (m, 2H), 1.99 (m, 2H), 2.60 (m, 1H), 3.34 (m, 2H), 4.19 (q, 2H), 4.38 (m, 2H), 7.09 (d, 2H), 7.17 (br s, 1H), 7.30 (d, 2H).

LCMS: m/z APCI$^+$ 327 [MH]$^+$

Preparation 36: N-(4-Chlorophenyl)-3-methylpiperazine-1-carbothioamide

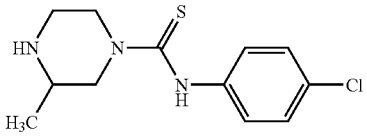

A solution of 4-chlorophenyl isothiocyanate (8.0 g, 47.17 mmol) in dichloromethane (250 mL) was added dropwise over 30 minutes to an ice cooled solution of 2-methylpiperazine (9.45 g, 94.33 mmol) in dichloromethane (250 mL). Once the addition was complete, the reaction was stirred at room temperature for an hour. The reaction was then washed with water (3×), dried over MgSO$_4$ and concentrated under reduced pressure, to give the title compound as a white solid, 11.8 g.

$^1$H NMR (400 MHz, CDCl$_3$): δ 1.08 (d, 3H), 2.70 (m, 1H), 2.88 (m, 2H), 3.02 (m, 2H), 4.43 (m, 2H), 7.10 (m, 2H), 7.29 (m, 2H). LCMS: m/z ES$^+$ 270.1 [MH]$^+$

Preparation 37: N-(4-Chlorophenyl)-4-(2,2-dimethylpropanoyl)-3-methylpiperazine-1-carbothioamide

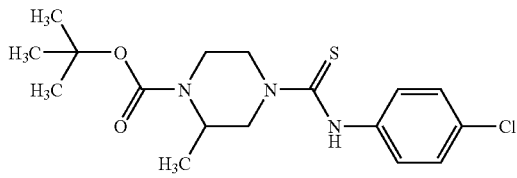

Di-tert-butyl dicarbonate (9.30 g, 42.6 mmol) was added to a solution of the compound of preparation 36 (11.5 g, 42.6 mmol) in dichloromethane (300 mL) and dioxan (100 mL) and the reaction was stirred at room temperature for 3 hours. The mixture was concentrated under reduced pressure and the product was recrystallised from methanol. The resulting solid was filtered off, and the filtrate was evaporated under reduced pressure. The residue was recrystallised again from methanol to afford the title compound, 9.64 g.

$^1$H NMR (400 MHz, DMSO-d$_6$): δ 1.05 (d, 3H), 1.39 (s, 9H), 3.17-3.36 (m, 2H), 3.58 (m, 1H), 3.77 (m, 1H), 4.14 (m, 1H), 4.40 (m, 2H), 7.32 (m, 4H), 9.36 (s, 1H). LCMS: m/z APCI$^+$ 370 [MH]$^+$

Preparation 38: N-(4-Chlorophenyl)-4-(2,2-dimethylpropanoyl)-2-methylpiperazine-1-carbothioamide

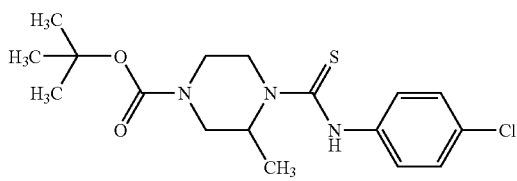

A solution of 4-chlorophenylisothiocyanate (5.1 g, 30 mmol) and 4-N—BOC-2-methylpiperazine (6.0 g, 30 mmol) in dichloromethane (250 mL) was stirred at room temperature for 2 hours. The reaction mixture was evaporated under reduced pressure to afford the title compound as a white foam.
LCMS: m/z APCI$^+$ 370 [MH]$^+$

Preparation 39: Ethyl 1-{[(4-chlorophenyl)amino]carbonothioyl}-4-methylpiperidine-4-carboxylate

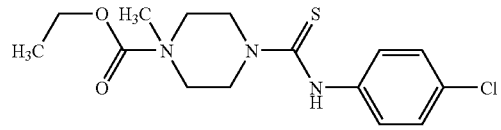

A mixture of 4-chlorophenyl isothiocyanate (2.36 g, 13.98 mmol), and ethyl 4-methylpiperidine-4-carboxylate (U.S. 2002/0086887, example 532C) (2.17 g, 12.71 mmol) in dichloromethane (50 mL) was stirred at room temperature for 30 minutes. The mixture was partitioned between dichloromethane and brine, and the layers were separated. The organic phase was dried over MgSO$_4$ and evaporated under reduced pressure. The crude product was purified by column chromatography on silica gel using dichloromethane:ethyl acetate (100:0 to 90:10) to provide the title compound as a white solid, 3.46 g.

$^1$H NMR (400 MHz, CDCl$_3$): δ 1.22 (m, 6H), 1.58 (m, 2H), 2.18 (m, 4H), 3.30 (m, 2H), 4.19 (q, 2H), 4.24 (m, 1H), 7.09 (d, 2H), 7.28 (d, 2H); LCMS: m/z APCI$^+$ 341 [MH]$^+$

Preparation 40: N-(4-Chlorophenyl)-4-cyano-4-phenylpiperidine-1-carbothioamide

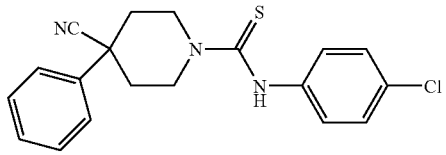

Triethylamine (1.4 mL, 10 mmol) was added to a suspension of 4-chlorophenyl isothiocyanate (1.69 g, 10 mmol) and 4-cyano-4-phenylpiperidine hydrochloride (2.22 g, 10 mmol) in dichloromethane (100 mL), and the reaction was then stirred at room temperature for 20 minutes. The mixture was washed with 2N hydrochloric acid, then brine, it was dried over MgSO$_4$ and evaporated under reduced pressure to afford the title compound as a white solid, 3.62 g.

$^1$H NMR (400 MHz, CDCl$_3$): δ 2.18 (m, 4H), 3.50 (m, 2H), 4.78 (m, 2H), 7.08 (d, 2H), 7.27-7.48 (m, 7H).

Preparations 41 to 44

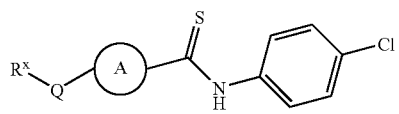

A mixture of 4-chlorophenyl isothiocyanate (1 eq.) and the appropriate amine (1 eq.) in ethanol (0.8-1.28 mLmmol$^{-1}$) was stirred at room temperature for 30 minutes. The reaction mixture was then evaporated under reduced pressure to afford the title compounds as a white solid.

| Prep. No. | R¹-Q-A | Data |
|---|---|---|
| 41 | ![structure: tert-butyl piperazine-1-carboxylate with methyl on N] | ¹H NMR (400 MHz, CDCl₃): δ 1.45 (s, 9H), 3.50 (m, 4H), 3.80 (m, 4H), 7.10 (d, 2H), 7.25 (d, 2H), 7.80 (s, 1H). LCMS: m/z APCI⁺ 356 [MH]⁺ |
| 42 | ![structure: acetyl piperazine] | ¹H NMR (400 MHz, CDCl₃): δ 2.10 (s, 3H), 3.60 (m, 2H), 3.78 (m, 4H), 4.02 (m, 2H), 7.14 (d, 2H), 7.30 (d, 2H). LCMS: m/z APCI⁺ 298 [MH]⁺ |
| 43 | ![structure: N-methylacetamido pyrrolidine] | ¹H NMR (400 MHz, CDCl₃): δ 2.04-2.24 (m, 4H), 2.85 (m, 1H), 2.94 (s, 3H), 3.62 (m, 2H), 3.95 (m, 2H), 5.25 (m, 1H), 6.60 (s, 1H), 7.30 (s, 4H). LCMS: m/z APCI⁺ 312 [MH]⁺ |
| 44 | ![structure: tert-butyl 4-aminopiperidine-1-carboxylate] | ¹H NMR (400 MHz, CDCl₃): δ 1.29-1.54 (m, 11H), 2.01 (m, 2H), 3.20 (m, 2H), 3.74 (br s, 1H), 4.35-4.55 (m, 3H), 7.09 (d, 2H), 7.17 (br s, 1H), 7.32 (d, 2H). |

Preparation 45: tert-Butyl 4-{[(4-chlorophenyl)amino]carbonothioyl}-1,4-diazepane-1-carboxylate A mixture of 4-chlorophenyl isothiocyanate (5.0 g, 29.95 mmol), and BOC-homopiperazine (6.0 g, 29.95 mmol) in ethanol (50 mL) was stirred at room temperature for 2 hours. The mixture was evaporated under reduced pressure, the residue was partitioned between ethyl acetate and water and the layers were separated. The organic phase was dried over MgSO₄ and evaporated under reduced pressure to give the title compound as a white foam.

¹H NMR (400 MHz, CD₃OD): δ 1.45 (s, 9H), 1.98 (m, 2H), 3.43 (m, 2H), 3.64 (m, 2H), 3.94-4.10 (m, 4H), 7.28 (s, 4H). LCMS: m/z APCI⁺ 370 [MH]⁺

Preparation 46: tert-Butyl 4-[(2)-[(4-chlorophenyl)imino](methylthio)methyl]piperidine-1-carboxylate

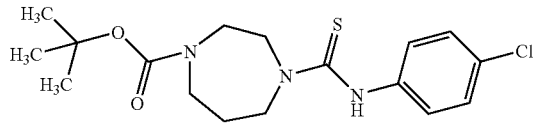

Potassium tert-butoxide (20.1 g, 0.18 mol) was added portionwise to a cooled (10° C.) solution of the compound of preparation 34 (53 g, 0.15 mol) in tetrahydrofuran (1 L), in order to maintain the temperature at 10° C. Methyl iodide (11.2 mL, 0.18 mol) was added dropwise, in order to maintain the temperature at 10° C., and the reaction was then allowed to warm slowly to room temperature. The reaction was stirred for a further 90 minutes, then it was quenched by the addition of water. The reaction was diluted with ethyl acetate and washed with water. The phases were separated, the aqueous layer was extracted with further ethyl acetate, and the combined organic solutions were dried over MgSO₄ and evaporated under reduced pressure. The residual oil was adsorbed onto silica gel and purified by column chromatography on silica gel using pentane:ethyl acetate (75:25) as eluant to afford the title compound as an oil that crystallised upon standing.

¹H NMR (400 MHz, CDCl₃): δ 1.43 (s, 9H), 1.57-1.82 (m, 5H), 2.35 (s, 3H), 2.42-2.62 (m, 1H), 2.78 (m, 1H), 4.16 (m, 2H), 6.65 (d, 2H), 7.26 (d, 2H). LCMS: m/z ES⁺ 391 [MNa]⁺

Preparation 47: Ethyl 1-[(2)-[(4-chlorophenyl)imino](methylthio)methyl]piperidine-4-carboxylate

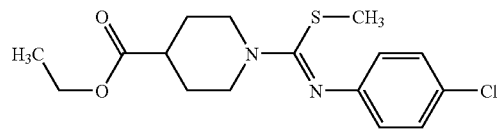

Potassium tert-butoxide (2.58 g, 23.1 mmol) was added portionwise to a solution of the compound of preparation 35 (6.27 g, 19.2 mmol) in tetrahydrofuran (100 mL) and the reaction was stirred for 10 minutes. Methyl iodide (1.44 mL, 23.1 mmol) was added and the reaction was stirred at room temperature for a further 30 minutes. The reaction was diluted with ether, and washed with brine. The organic solution was evaporated under reduced pressure and the resulting orange solid was purified by column chromatography on silica gel using dichloromethane as eluant to afford the title compound as an oil, 3.6 g.

$^1$H NMR (400 MHz, CDCl$_3$): δ 1.25 (t, 3H), 1.78 (m, 2H), 1.98 (m, 2H), 2.04 (s, 3H), 2.56 (m, 1H), 3.01 (m, 2H), 4.12-4.23 (m, 4H), 6.80 (d, 2H), 7.20 (d, 2H); LCMS: m/z ES$^+$ 341 [MH]$^+$

Preparation 48: Ethyl 1-[(Z)-[(4-chlorophenyl)imino](methylthio)methyl]-4-methylpiperidine-4-carboxylate

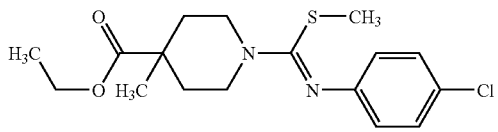

The title compound was obtained as an oil in 75% yield from the compound of preparation 39 and methyl iodide, following a similar procedure to that described for preparation 47, except that the product was not purified by column chromatography on silica gel.

$^1$H NMR (400 MHz, CDCl$_3$): δ 1.25 (m, 6H), 1.50 (m, 2H), 2.04 (s, 3H), 2.18 (m, 2H), 3.19 (m, 2H), 3.98 (m, 2H), 4.19 (q, 2H), 6.80 (m, 2H), 7.20 (d, 2H); LCMS: m/z ES$^+$ 355 [MH]$^+$

Preparations 49 to 55

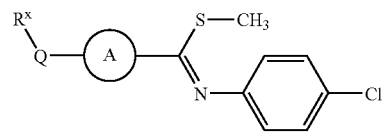

Potassium tert-butoxide (1.1 eq.), followed by methyl p-toluenesulphonate (1.1 eq.) was added to a solution of a compound selected from preparations 37, 38, 40-42 and 45 (1 eq.) in tetrahydrofuran and the reaction was stirred at room temperature for 2 hours. The mixture was concentrated under reduced pressure and the residue was partitioned between ethyl acetate and water, the layers were separated and the organic solution was washed with water (3×), dried over MgSO$_4$ and evaporated under reduced pressure to give the title compounds.

| Prep. No. | $R^x{-}Q{-}A$ | Data |
|---|---|---|
| 49 | (tert-butoxycarbonyl 2-methyl piperazine) | $^1$H NMR (400 MHz, CDCl$_3$): δ 1.20 (d, 3H), 1.44 (s, 9H), 2.00 (s, 3H), 2.99 (m, 1H), 3.19 (m, 2H), 3.88 (m, 1H), 4.16 (m, 1H), 4.20-4.36 (m, 2H), 6.83 (m, 2H), 7.21 (m, 2H). LCMS: m/z APCI$^+$ 384 [MH]$^+$ |
| 50 | (tert-butoxycarbonyl 3-methyl piperazine) | $^1$H NMR (400 MHz, CDCl$_3$): δ 1.21 (d, 3H), 1.42 (s, 9H), 2.00 (s, 3H), 2.80-3.30 (m, 3H), 3.80-4.18 (m, 3H), 4.54 (m, 1H), 6.80 (m, 2H), 7.20 (m, 2H). LCMS: m/z APCI$^+$ 384 [MH]$^+$ |
| 51 | (4-cyano-4-phenyl piperidine) | $^1$H NMR (400 MHz, CDCl$_3$): δ 2.06 (s, 3H), 2.17 (m, 2H), 3.38-3.52 (m, 4H), 4.50 (m, 2H), 6.83 (d, 2H), 7.22 (d, 2H), 7.38 (m, 1H), 7.42 (m, 2H), 7.52 (d, 2H). |
| 52 | (tert-butoxycarbonyl piperazine) | $^1$H NMR (400 MHz, CDCl$_3$): δ 1.46 (s, 9H), 2.02 (s, 3H), 3.48 (m, 4H), 3.58 (m, 4H), 6.80 (d, 2H), 7.20 (d, 2H). |
| 53 | (1-acetyl piperazine) | $^1$H NMR (400 MHz, CDCl$_3$): δ 2.01 (s, 3H), 2.10 (s, 3H), 3.48-3.76 (m, 8H), 6.80 (d, 2H), 7.19 (d, 2H) LCMS: m/z APCI$^+$ 312 [MH]$^+$ |
| 54 | (N-methyl-N-acetyl-3-aminopyrrolidine) | $^1$H NMR (400 MHz, CDCl$_3$): δ 1.98 (s, 3H), 2.09 (s, 3H), 2.84 (m, 1H), 2.90 (s, 3H), 3.38 (m, 1H), 3.46 (m, 1H), 3.77 (m, 2H), 5.22 (m, 1H), 6.82 (d, 2H), 7.19 (d, 2H). LCMS: m/z APCI$^+$ 326 [MH]$^+$ |

-continued

| Prep. No. | R<sup>x</sup>\Q—A | Data |
|---|---|---|
| 55 | 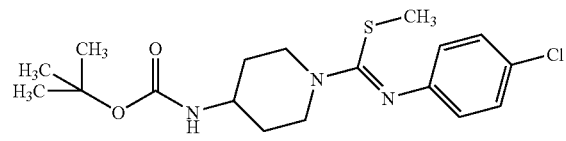 | ¹H NMR (400 MHz, CD₃OD) : δ 1.45 (2xs, 9H), 1.90 (m, 5H), 3.44 (m, 2H), 3.60 (m, 2H), 3.76 (m, 2H), 3.80 (m, 2H), 6.85 (d, 2H), 7.20 (d, 2H). |

A = the reaction was stirred at room temperature for 18 hours, and the product was additionally purified by column chromatography on silica gel using dichloromethane:methanol as eluant.

Preparation 56: Methyl 4-[(tert-butoxycarbonyl)amino]-N-(4-chlorophenyl)piperidine-1-carbimidothioate

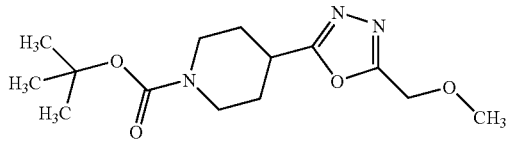

Potassium tert-butoxide (12.8 g, 114 mmol) was added to a suspension of the compound of preparation 44 (42.3 g, 114 mmol) in tetrahydrofuran (400 mL) and the suspension was stirred for 10 minutes at room temperature. Methyl p-toluenesulphonate (21.29 g, 114 mmol) was added and the reaction was stirred for 10 minutes. Additional potassium tert-butoxide (641 mg, 5.7 mmol) and methyl p-toluenesulphonate (1.08 g, 5.7 mmol) were added and the reaction was stirred for a further 10 minutes. The mixture was diluted with ether, washed with water (200 mL) and brine, then dried over MgSO₄ and evaporated under reduced pressure to afford the title compound.

¹H NMR (400 MHz, CDCl₃): δ 1.34-1.52 (m, 11H), 2.00 (m, 2H), 2.05 (s, 3H), 3.04 (m, 2H), 3.68 (br s, 1H), 4.19 (m, 2H), 4.50 (br s, 1H), 6.80 (d, 2H), 7.20 (d, 2H). LCMS: m/z ES⁺ 384 [MH]⁺

Preparation 57: tert-Butyl 4-[5-(methoxymethyl)-1,3,4-oxadiazol-2-yl]piperidine-1-carboxylate

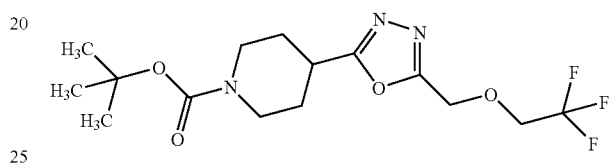

Potassium tert-butoxide (3.40 g, 30.3 mmol) was added to a solution of the compound of preparation 8 (7.62 g, 25.25 mmol) in methanol (120 mL) and the reaction was stirred at room temperature for 18 hours. Tlc analysis showed that starting material remained, so additional potassium tert-butoxide (1 g, 8.9 mmol) was added and the reaction was stirred at 50° C. for 2 hours. The mixture was concentrated under reduced pressure and the residue was partitioned between ethyl acetate and ammonium chloride solution. The layers were separated, the organic phase was dried over MgSO₄ and evaporated under reduced pressure to afford the title compound as a yellow oil, 7.30 g.

¹H NMR (400 MHz, CDCl₃): δ 1.45 (s, 9H), 1.82 (m, 2H), 2.08 (m, 2H), 2.96 (m, 2H), 3.08 (m, 1H), 3.44 (s, 3H), 4.10 (m, 2H), 4.61 (s, 2H). LCMS: m/z APCI⁺ 298 [MH]⁺

Preparation 58: tert-Butyl 4-{5-[(2,2,2-trifluoroethoxy)methyl]-1,3,4-oxadiazol-2-yl}piperidine-1-carboxylate

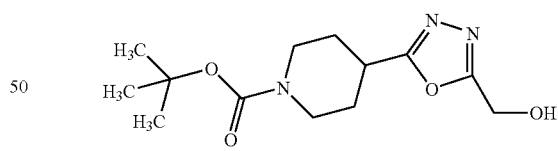

Potassium tert-butoxide (1.8 g, 41.8 mmol) was added to a solution of 2,2,2-trifluoroethanol (4.64 g, 46.4 mmol) in tetrahydrofuran (100 mL) and the solution was stirred at room temperature for 10 minutes. The compound of preparation 8 (7.0 g, 23.2 mmol) was added and the mixture was then heated at 50° C. for 2 hours. The reaction was quenched by the addition of ammonium chloride solution, then the organic layer was decanted off and evaporated under reduced pressure. The residue was re-dissolved in ethyl acetate, the solution was washed with brine, dried over MgSO₄ and then evaporated under reduced pressure to afford the title compound as a yellow oil, 8.15 g.

¹H NMR (400 MHz, CDCl₃): δ 1.43 (s, 9H), 1.80 (m, 2H), 2.06 (m, 2H), 2.97 (m, 2H), 3.10 (m, 1H), 3.96 (q, 2H), 4.12 (m, 2H), 4.82 (s, 2H).

Preparation 59: tert-Butyl 4-[5-(hydroxymethyl)-1,3,4-oxadiazol-2-yl]piperidine-1-carboxylate Potassium acetate (5.2 g, 53.0 mmol) was added to a solution of the compound of preparation 8 (8 g, 26.5 mmol) in acetonitrile (150 mL), and the reaction was heated at 80° C. for 18 hours. The cooled mixture was concentrated under reduced pressure and the residue was partitioned between water and ethyl acetate, and the layers were separated. The organic phase was washed with brine, dried over MgSO₄ and evaporated under reduced pressure. The residual oil was dissolved in methanol (120 mL), and sodium carbonate (5.6 g, 53.0 mmol) and water (1 mL) were added. The mixture was stirred at room temperature for 2 hours and then it was evaporated under reduced pressure. The residue was partitioned between ethyl acetate and water. The organic layer was washed with brine, dried over MgSO₄ and evaporated under reduced pressure to afford the title compound as an off-white solid, 7.16 g.

¹H NMR (400 MHz, CDCl₃): δ 1.45 (s, 9H), 1.81 (m, 2H), 2.04 (m, 2H), 2.17 (m, 1H), 2.97 (m, 2H), 3.08 (m, 1H), 4.11 (m, 2H), 4.82 (s, 2H). LCMS: m/z ES⁺ 306 [MNa]⁺

Preparation 60: tert-Butyl 4-[5-(morpholin-4-ylmethyl)-1,3,4-oxadiazol-2-yl]piperidine-1-carboxylate

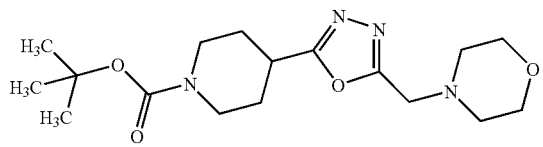

A mixture of the compound of preparation 8 (10 g, 33.1 mmol), morpholine (4.3 mL, 49.7 mmol) and potassium carbonate (9.2 g, 66.2 mmol) in acetonitrile (300 mL) was stirred at 80° C. for 4 hours. The cooled mixture was concentrated under reduced pressure and the residue was partitioned between water and ethyl acetate. The organic phase was dried over MgSO₄ and evaporated under reduced pressure to provide the title compound as an orange oil, 12.06 g.

¹H NMR (400 MHz, CD₃OD): δ 1.45 (s, 9H), 1.65-1.78 (m, 2H), 2.04 (m, 2H), 2.58 (m, 4H), 3.00 (m, 2H), 3.10 (m, 1H), 3.68 (t, 2H), 3.81 (s, 2H), 4.06 (m, 2H). LCMS: m/z ES⁺ 353 [MH]⁺

Preparation 61: tert-Butyl 4-{[2-(ethoxyacetyl)hydrazino]carbonyl}piperidine-1-carboxylate

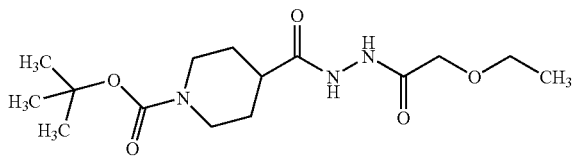

A mixture of 4-hydrazinocarbonyl-piperidine-1-carboxylic acid tert-butyl ester (WO 2000039125, prep 27) (3 g, 12.33 mmol), ethoxyacetic acid (1.28 mL, 13.56 mmol), 1-(3-dimethylaminopropyl)-3-ethylcarbodiimide hydrochloride (2.6 g, 13.56 mmol), 1-hydroxybenzotriazole hydrate (1.83 g, 13.56 mmol) and triethylamine (2.1 mL, 14.8 mmol) in N,N-dimethylformamide (15 mL) was stirred at room temperature for 18 hours. The mixture was concentrated under reduced pressure and the residue was partitioned between ethyl acetate and aqueous sodium carbonate solution. The layers were separated, the organic phase was dried over MgSO₄ and evaporated under reduced pressure to provide the title compound as an oil, that crystallised on standing.

¹H NMR (400 MHz, CDCl₃): δ 1.24 (t, 3H), 1.45 (s, 9H), 1.58-1.78 (m, 2H), 1.81 (m, 2H), 2.38 (m, 1H), 2.74-2.82 (m, 2H), 3.60 (q, 2H), 4.04-4.21 (m, 2H), 8.26 (br s, 1H), 8.82 (br s, 1H). LCMS: m/z APCI⁺ 330 [MH]⁺

Preparation 62: tert-Butyl 4-{[2-(3,3,3-trifluoropropanoyl)hydrazino]carbonyl}piperidine-1-carboxylate

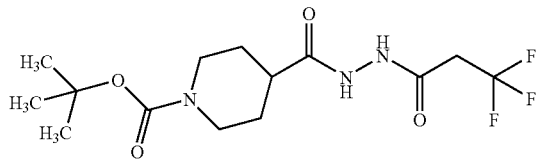

The title compound was obtained from 4-hydrazinocarbonyl-piperidine-1-carboxylic acid tert-butyl ester (WO 2000039125, prep 27) and 3,3,3-trifluoropropionic acid, following a similar procedure to that described for preparation 61.

¹H NMR (400 MHz, CD₃OD): δ 1.44 (s, 9H), 1.60 (m, 2H), 1.80 (m, 2H), 2.43 (m, 1H), 2.81 (m, 2H), 3.22 (q, 2H), 4.10 (m, 2H). LCMS: m/z APCI⁻ 352 [M-H]⁻

Preparation 63: tert-Butyl 4-[5-(ethoxymethyl)-1,3,4-oxadiazol-2-yl]piperidine-1-carboxylate

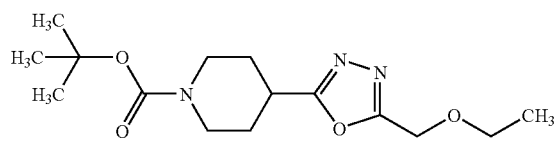

Pyridine (4 mL, 49.3 mmol) was added dropwise to an ice-cooled solution of the compound of preparation 61 (4.06 g, 12.33 mmol) in dichloromethane (60 mL). Triflic anhydride (4.2 mL, 24.6 mmol) was then added dropwise over 20 minutes and the solution was stirred for an hour at 0° C. It was then stirred for a further hour at room temperature. The mixture was basified to pH 4 using aqueous sodium bicarbonate solution, and extracted with dichloromethane. The combined organic extracts were dried over MgSO₄, and concentrated under reduced pressure. The crude product was purified by column chromatography on silica gel using dichloromethane:methanol:0.88 ammonia (97:3:0.3) to provide the title compound as a yellow oil, 1.25 g.

¹H NMR (400 MHz, CDCl₃): δ 1.23 (t, 3H), 1.44 (s, 9H), 1.81 (m, 2H), 2.04 (m, 2H), 2.96 (m, 2H), 3.10 (m, 1H), 3.60 (q, 2H), 4.14 (m, 2H), 4.66 (s, 2H). LCMS: m/z APCI⁺ 312 [MH]⁺

Preparation 64: tert-Butyl 4-[5-(2,2,2-trifluoroethyl)-1,3,4-oxadiazol-2-yl]piperidine-1-carboxylate

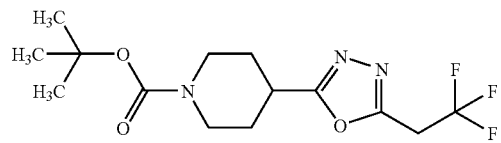

The title compound was obtained as a pale yellow solid, from the compound of preparation 62, following a similar procedure to that described for preparation 63.

¹H NMR (400 MHz, CDCl₃): δ 1.42 (s, 9H), 1.81 (m, 2H), 2.04 (m, 2H), 2.98 (m, 2H), 3.08 (m, 1H), 3.76 (q, 2H), 4.10 (m, 2H). LCMS: m/z APCI⁺ 358 [MNa]⁺

Preparation 65: 1-(4-Chlorobenzoyl)-4-(1,3,4-oxadiazol-2-yl)piperidine

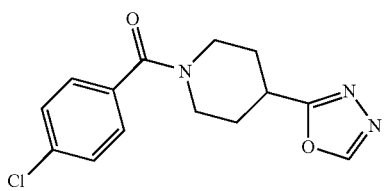

N,N-Dimethylformamide dimethyl acetal (5.71 g, 47.9 mmol) was added to a solution of the compound of preparation 29 (9.0 g, 31.94 mmol) in N,N-dimethylformamide (100 mL), and the reaction was stirred for 3 hours at 50° C. The mixture was concentrated under reduced pressure and the residue was suspended in toluene (150 mL). p-Toluene sulphonic acid (1 g, 5.26 mmol) was added and the reaction was heated at 110° C. for 18 hours. The reaction was diluted with ethyl acetate (100 mL), washed with brine, water and then brine again. The solution was dried over MgSO$_4$ and then evaporated under reduced pressure. The crude product was purified by column chromatography using a silica gel cartridge and dichloromethane:methanol (100:0 to 90:10) as eluant to afford the title compound as a white solid, 4.25 g.

LCMS: m/z APCI$^+$ 292 [MH]$^+$

Preparation 66: 1-(3-Chlorobenzoyl)-4-(1,3,4-oxadiazol-2-yl)piperidine

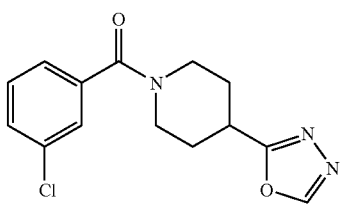

N,N-Dimethylformamide dimethyl acetal (5.71 g, 47.9 mmol) was added to a solution of the compound of preparation 4 (9.0 g, 31.94 mmol) in tetrahydrofuran (6 mL), and the reaction was stirred for 18 hours at 50° C. Tlc analysis showed that starting material remained, so additional N,N-dimethylformamide dimethyl acetal (15 mmol) was added and stirring was continued for a further 2 hours. The mixture was concentrated under reduced pressure and the residue was suspended in toluene (32 mL). p-Toluene sulphonic acid (1 g, 5.26 mmol) was added and the reaction was heated at 110° C. for 18 hours. The reaction was diluted with ethyl acetate (100 mL), washed with saturated sodium bicarbonate solution (2×) and brine, then dried over Na$_2$SO$_4$ and evaporated under reduced pressure. The crude product was purified by column chromatography on silica gel using an elution gradient of dichloromethane:methanol:0.88 ammonia (100:0:0 to 90:10:1) to afford the title compound.

$^1$H NMR (400 MHz, CDCl$_3$): δ 1.95 (m, 2H), 2.04-2.28 (m, 2H), 3.12-3.30 (m, 3H), 3.80 (m, 1H), 4.58 (m, 1H), 7.28 (m, 2H), 7.39 (m, 2H), 8.40 (s, 1H).

LCMS: m/z APCI$^+$ 292 [MH]$^+$

Preparation 67: 1-(4-Chlorobenzoyl)-4-(5-methyl-1,3,4-oxadiazol-2-yl)piperidine

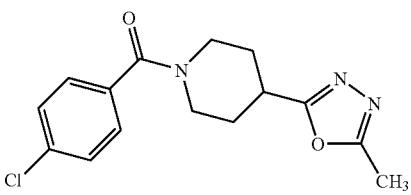

N,N-Dimethylacetamide dimethyl acetal (6.38 g, 47.9 mmol) was added to a solution of the compound of preparation 29 (9.0 g, 31.94 mmol) in N,N-dimethylformamide (20 mL), and the reaction was stirred at room temperature for 1 hour. It was then stirred for a further 2 hours at 40° C. The mixture was diluted with toluene (150 mL), heated to 110° C. and then p-toluene sulphonic acid (400 mg, 2.22 mmol) was added. The reaction was heated at 110° C. for 18 hours, then cooled and concentrated under reduced pressure. The residue was dissolved in ethyl acetate, washed with ammonium chloride solution and brine, then it was dried over MgSO$_4$ and evaporated under reduced pressure to afford the title compound as an oil, 9.75 g.

$^1$H NMR (400 MHz, CDCl$_3$): δ 1.81-1.97 (m, 2H), 2.00-2.22 (m, 2H), 2.56 (s, 3H), 3.18 (m, 3H), 3.90 (m, 1H), 4.58 (m, 1H), 7.38 (m, 4H). LCMS: m/z APCI$^+$ 306 [MH]$^+$.

Preparation 68: 1-(4-Chlorobenzoyl)-4-(5-ethyl-1,3,4-oxadiazol-2-yl)piperidine

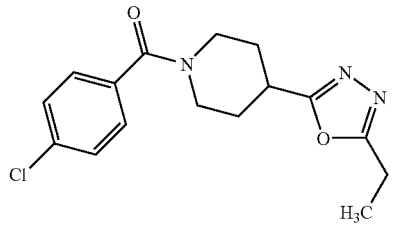

Triethyl orthopropionate (1.63 g, 9.23 mmol) was added to a solution of the compound of preparation 29 (2.0 g, 7.1 mmol) in N,N-dimethylformamide (10 mL), and stirred at 60° C. for 3 hours. Tlc analysis showed that starting material remained, so additional triethyl orthopropionate (0.5 g, 2.83 mmol) was added and the reaction was stirred at 60° C. for a further 18 hours. The mixture was concentrated under reduced pressure, the residue was suspended in toluene (15 mL) and trifluoroacetic acid (5 drops) was added. The reaction was heated under reflux for 18 hours, then cooled and concentrated under reduced pressure. The crude product was purified by column chromatography using a silica gel cartridge and dichloromethane:methanol (100:0 to 95:5) as eluant to afford the title compound as an oil, 1.6 g.

$^1$H NMR (400 MHz, CDCl$_3$): δ 1.38 (t, 3H), 1.90 (m, 2H), 2.00-2.21 (m, 2H), 2.85 (q, 2H), 3.19 (m, 3H), 3.80 (m, 1H), 4.58 (m, 1H), 7.38 (m, 4H). LCMS: m/z ES$^+$ 320, 322 [MH]$^+$

Preparation 69: 1-(3-Chlorobenzoyl)-4-[5-(ethoxymethyl)-1,3,4-oxadiazol-2-yl]piperidine

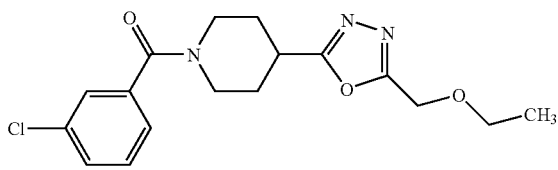

Pyridine (1.8 g, 22.84 mmol) and then triflic anhydride (3.22 g, 11.42 mmol) were added to an ice-cooled solution of the compound of preparation 32 (2.80 g, 7.61 mmol) in dichloromethane (50 mL). The reaction was then stirred at room temperature for 2 hours. The mixture was washed with ammonium chloride solution (3×), then with saturated aqueous sodium carbonate solution, dried over MgSO$_4$ and treated with activated carbon. This mixture was then filtered and the filtrate was evaporated under reduced pressure. The crude product was purified by column chromatography using a silica gel cartridge and an elution gradient of dichloromethane:methanol (100:0 to 95:5) to provide the title compound as a yellow oil, 566 mg.

$^1$H NMR (400 MHz, CDCl$_3$): δ 1.23 (t, 3H), 1.83-2.24 (m, 3H), 3.14-3.26 (m, 4H), 3.62 (q, 2H), 3.80 (m, 1H), 4.59 (m, 1H), 4.67 (s, 2H), 7.25 (m, 1H), 7.40 (m, 3H). LCMS: m/z APCI$^+$ 350 [MH]$^+$

Preparation 70: 1-(4-Chlorobenzoyl)-4-[5-(ethoxymethyl)-1,3,4-oxadiazol-2-yl]piperidine

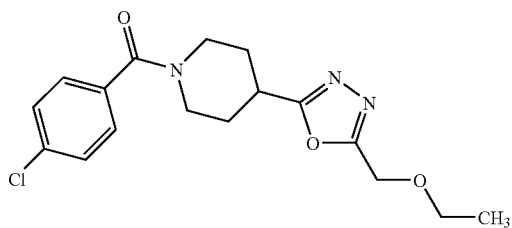

The title compound was obtained as a crystalline solid from the compound of preparation 31 following a similar procedure to that described for preparation 69.

$^1$H NMR (400 MHz, CDCl$_3$): δ 1.23 (t, 3H), 1.83-1.99 (m, 2H), 2.04-2.22 (m, 2H), 3.14-3.26 (m, 3H), 3.62 (q, 2H), 3.79-3.90 (m, 1H), 4.59 (m, 1H), 4.67 (s, 2H), 7.40 (m, 4H). LCMS: m/z APCI$^+$ 350 [MH]$^+$

Preparation 71: 1-(4-Chlorobenzoyl)-4-[5-(trifluoromethyl)-1,3,4-oxadiazol-2-yl]piperidine

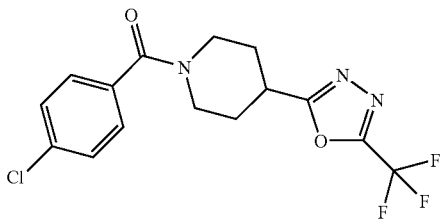

Triflic anhydride (1.98 mL, 11.7 mmol) was added to an ice-cooled solution of the compound of preparation 30 (1.77 g, 4.69 mmol) and pyridine (1.53 mL, 18.74 mmol) in dichloromethane (40 mL). The mixture was then allowed to warm to room temperature and stirred for 18 hours. The reaction was diluted with dichloromethane, washed with 2N hydrochloric acid, then saturated aqueous sodium bicarbonate solution. It was dried over MgSO$_4$ and evaporated under reduced pressure. The crude product was purified by column chromatography on silica gel using an elution gradient of dichloromethane:methanol (99:1 to 96:4) to provide the title compound as a brown oil, 620 mg.

$^1$H NMR (400 MHz, CDCl$_3$): δ 1.60 (m, 1H), 1.97 (m, 3H), 2.20 (m, 2H), 3.20 (m, 2H), 3.34 (m, 1H), 7.39 (m, 4H). LCMS: m/z APCI$^+$ 360 [MH]$^+$

Preparations 72 to 74

The compounds of the following general structure shown below:

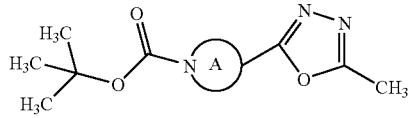

were prepared from N,N-dimethylacetamide dimethyl acetal and the appropriate hydrazide, following a similar procedure to that described for preparation 67.

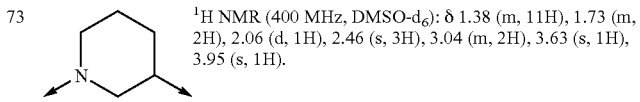

| Prep. No | A | Data |
|---|---|---|
| 72 | 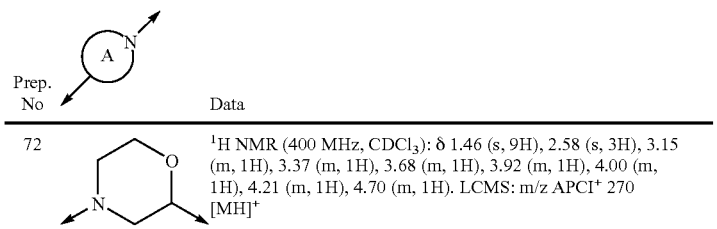 | $^1$H NMR (400 MHz, CDCl$_3$): δ 1.46 (s, 9H), 2.58 (s, 3H), 3.15 (m, 1H), 3.37 (m, 1H), 3.68 (m, 1H), 3.92 (m, 1H), 4.00 (m, 1H), 4.21 (m, 1H), 4.70 (m, 1H). LCMS: m/z APCI$^+$ 270 [MH]$^+$ |
| 73 | | $^1$H NMR (400 MHz, DMSO-d$_6$): δ 1.38 (m, 11H), 1.73 (m, 2H), 2.06 (d, 1H), 2.46 (s, 3H), 3.04 (m, 2H), 3.63 (s, 1H), 3.95 (s, 1H). |

-continued

| Prep. No | 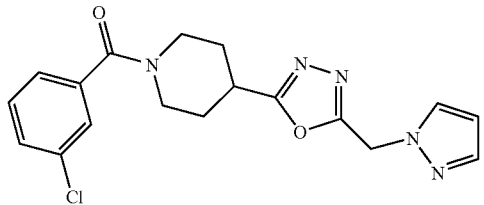 Data |
|---|---|
| 74 | ¹H NMR (400 MHz, CDCl₃): δ 1.44 (s, 9H), 2.19-2.38 (m, 2H), 2.54 (s, 3H), 3.44 (m, 1H), 3.60 (m, 3H), 3.80 (m, 1H). |

A = 3-hydrazinocarbonyl-pyrrolidine-1-carboxylic acid tert-butyl ester was used (obtained from CB Research and Development Inc.).

Preparation 75: 1-(3-Chlorobenzoyl)-4-[5-(1H-pyrazol-1-ylmethyl)-1,3,4-oxadiazol-2-yl]piperidine

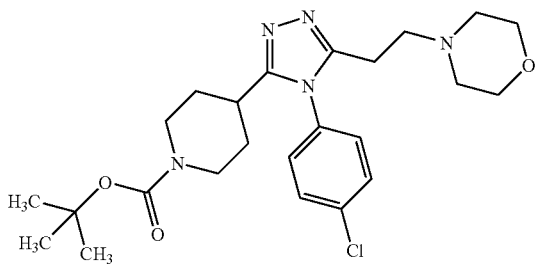

A mixture of the compound of preparation 6 (1 g, 2.94 mmol), pyrazole (400 mg, 5.9 mmol) and potassium carbonate (610 mg, 4.4 mmol) in acetonitrile (10 mL) and N,N-dimethylformamide (10 mL) was stirred at 100° C. for 18 hours. The cooled mixture was filtered, and the filtrate was concentrated under reduced pressure. The residue was diluted with ethyl acetate, washed with water (2x), and brine. It was then dried over MgSO₄. The crude product was purified by column chromatography on silica gel using dichloromethane:methanol:0.88 ammonia (100:0:0 to 95:5:0.5) to afford the title compound, 550 mg.

¹H NMR (400 MHz, CD₃OD): δ 1.76-1.92 (m, 3H), 1.99-2.22 (m, 3H), 3.18 (m, 1H), 3.70 (m, 1H), 4.50 (m, 1H), 5.63 (s, 2H), 6.35 (d, 1H), 6.38 (d, 1H), 7.37 (d, 1H), 7.44 (m, 2H), 7.52 (s, 1H), 7.80 (s, 1H); LCMS: m/z ES⁺ 372 [MH]⁺

Preparation 76: tert-Butyl 4-[4-(4-chlorophenyl)-5-(2-morpholin-4-ylethyl)-4H-1,2,4-triazol-3-yl]piperidine-1-carboxylate

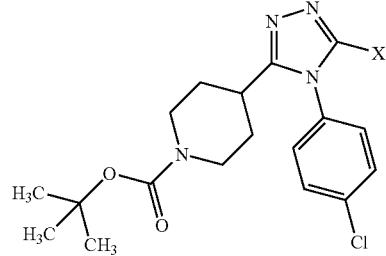

Trifluoroacetic acid (0.35 mL, 4.3 mmol) was added to 4-morpholinpropanoic acid hydrazide (Comptes Rendus des Seances de l'academie des Sciences, Serie C; Sciences Chimiques 1976; 282 (17); 857-60) (1.5 g, 8.7 mmol) and the compound of preparation 46 (2.7 g, 7.25 mmol) in tetrahydrofuran (18 mL), and the reaction was heated under reflux for 8 hours. The cooled mixture was diluted with dichloromethane, washed with 1N sodium hydroxide solution, and evaporated under reduced pressure. The crude product was purified by column chromatography on silica gel using an elution gradient of dichloromethane:methanol:0.88 ammonia (100:0:0 to 10:10:1) to give the title compound, 2.2 g.

¹H NMR (400 MHz, CDCl₃): δ 1.45 (s, 9H), 1.59-1.95 (m, 4H), 2.40 (m, 4H), 2.58 (m, 1H), 2.61-2.80 (m, 6H), 3.64 (m, 4H), 4.10 (m, 2H), 7.19 (d, 2H), 7.57 (d, 2H); LCMS: m/z APCI⁺ 476, 478 [MH]⁺

Preparations 77 to 87

The compounds of the general formula shown below:

were prepared from the compound of preparation 46 and the appropriate hydrazide, following a similar procedure to that described for preparation 76.

| Prep. No. | Data |
|---|---|
| 77 | X=2-oxo-1-pyrrolidinylmethyl<br>¹H NMR(400MHz, CDCl₃): δ 1.42(s, 9H), 1.71(m, 2H), 1.77-2.00(m, 4H), 2.20(t, 2H), 2.56-2.74(m, 3H), 3.45(t, 2H), 4.06(m, 2H), 4.42(s, 2H), 7.19(d, 2H), 7.54(d, 2H). LCMS: m/z APCI⁺ 460[MH]⁺ |
| 78ᴬ | X=imidazol-1-ylmethyl<br>¹H NMR(400MHz, CDCl₃): δ 1.41(s, 9H), 1.70(m, 2H), 1.83(m, 2H), 2.55(m, 1H), 2.65(m, 2H), 4.10(m, 2H), 5.17(s, 2H), 6.78(s, 1H), 6.90(d, 2H), 7.01(s, 1H), 7.19(s, 1H), 7.52(d, 2H). LCMS: m/z APCI⁺ 443[MH]⁺ |
| 79ᴮ | X=2-methyl-1H-imidazol-1-ylmethyl<br>¹H NMR(400MHz, CDCl₃): δ 1.43(s, 9H), 1.70(m, 2H), 1.84(m, 2H), 2.01(s, 3H), 2.52(m, 1H), 2.66(m, 2H), 4.10(m, 2H), 5.02(s, 2H), 6.55(s, 1H), 6.85(m, 3H), 7.53(d, 2H). LCMS: m/z APCI⁺ 457[MH]⁺ |
| 80 | X=1,2,4-triazol-1-ylmethyl<br>¹H NMR(400MHz, CDCl₃): δ 1.42(s, 9H), 1.76(m, 2H), 1.86(m, 2H), 2.55-2.75(m, 3H), 4.12(m, 2H), 5.39(s, 2H), 7.12(d, 2H), 7.57(d, 2H), 7.82(s, 1H), 8.05(s, 1H). LCMS: m/z APCI⁺ 444[MH]⁺ |
| 81 | X=tetrazol-1-ylmethyl<br>¹H NMR(400MHz, CDCl₃): δ 1.43(s, 9H), 1.63-1.95(m, 4H), 2.58-2.75(m, 3H), 4.11(m, 2H), 5.60(s, 2H), 7.15(d, 2H), 7.59(d, 2H), 8.81(s, 1H). LCMS: m/z ES⁺ 445[MH]⁺ |

-continued

| Prep. No. | Data |
|---|---|
| 82[C] | X=3-methylisoxazol-5-ylmethyl<br>1H NMR(400MHz, CDCl3): δ 1.37(s, 9H), 1.60-1.82(m, 4H), 2.14(s, 3H), 2.45-2.65(m, 3H), 3.96-4.05(m, 4H), 5.82(s, 1H), 7.06(d, 2H), 7.44(d, 2H). LCMS: m/z APCl+ 458[MH]+ |
| 83 | X=3-methyl-1,2,4-oxadiazol-5-ylmethyl<br>1H NMR(400MHz, CDCl3): δ 1.44(s, 9H), 1.62-1.95(m, 4H), 2.32(s, 3H), 2.70(m, 3H), 4.10(m, 2H), 4.24(s, 2H), 7.18(d, 2H), 7.54(d, 2H). LCMS: m/z APCl+ 459[MH]+ |
| 84 | X=pyrimidin-2-yloxymethyl<br>1H NMR(400MHz, CDCl3): δ 1.41(s, 9H), 1.59-76(m, 2H), 1.86(m, 2H), 2.58-2.76(m, 3H), 4.10(m, 2H), 5.39(s, 2H), 6.95(m, 1H), 7.26(d, 2H), 7.43(d, 2H), 8.42(s, 2H). LCMS: m/z APCl+ 471, 473[MH]+ |
| 85 | X=2-piperidin-1-ylethyl<br>1H NMR(400MHz, CDCl3): δ 1.39-1.78(m, 19H), 1.78-1.86(m, 2H), 2.28-3.04(m, 3H), 2.56-2.82(m, 6H), 4.08(m, 2H), 7.19(d, 2H), 7.58(d, 2H). LCMS: m/z APCl+ 474[MH]+ |
| 86[C] | X=2-pyridin-2-ylethyl<br>1H NMR(400MHz, CDCl3): δ 1.42(s, 9H), 1.66(m, 2H), 1.78-1.90(m, 2H), 2.56(m, 1H), 2.60-2.74(m, 2H), 2.98(t, 2H), 3.26(t, 2H), 4.06(m, 2H), 7.03(d, 2H), 7.12(m, 1H), 7.18(d, 1H), 7.50(d, 2H), 7.58(m, 1H), 8.42(d, 1H). LCMS: m/z APCl+ 468[MH]+ |
| 87 | X=2-(3,5-dimethylisoxazol-4-yl)ethyl<br>1H NMR(400MHz, CDCl3): δ 1.42(s, 9H), 1.70(m, 2H), 1.79-1.93(m, 5H), 2.04(s, 3H), 2.54(m, 1H), 2.60-2.80(m, 4H), 4.10(m, 2H), 5.32(s, 2H), 6.90(d, 2H), 7.56(d, 2H). LCMS: m/z APCl+ 486[MH]+ |

[A]= 1-imidazol-1-yl acetic acid hydrazide was used; prepared as described in Boll. Chim. Farm. 114(2); 70-72; 1975.
[B]= the reaction was stirred for 18 hours under reflux.
[C]= 1 eq. hydrazide was used.

Preparation 88: tert-Butyl {1-[4-(4-chlorophenyl)-5-methyl-4H-1,2,4-triazol-3-yl]piperidin-4-yl}carbamate

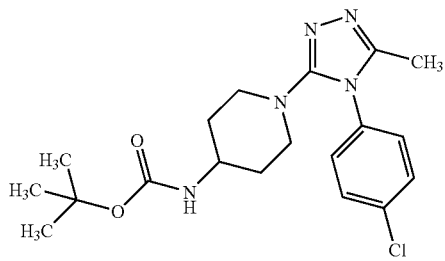

Acetic hydrazide (16.9 g, 228 mmol) followed by trifluoroacetic acid (4.4 mL, 57.1 mmol) were added to a solution of the compound of preparation 56 (43.6 g, 114 mmol) in tetrahydrofuran (250 mL) and the mixture was heated under reflux for 7 hours. The cooled mixture was then washed with dilute ammonia solution, the layers were separated and the aqueous phase was extracted further with ethyl acetate. The combined organic solutions were dried over MgSO4 and evaporated under reduced pressure. The residue was triturated with ether (100 mL) and the resulting crystals were filtered off and dried in vacuo to afford the title compound, 32.4 g.

1H NMR (400 MHz, CDCl3): δ 1.32 (m, 2H), 1.40 (s, 9H), 1.85 (m, 2H), 2.22 (s, 3H), 2.84 (m, 2H), 3.24 (m, 2H), 3.52 (m, 1H), 4.44 (m, 1H), 7.24 (d, 2H), 7.51 (d, 2H); LCMS: m/z APCl+ 392 [MH]+

Preparation 89: tert-butyl 4-[4-(4-chlorophenyl)-5-methyl-4H-1,2,4-triazol-3-yl]-1,4-diazepane-1-carboxylate

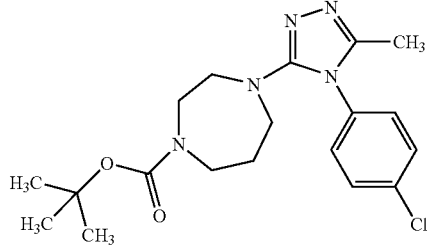

The title compound was obtained in 75% yield from the compound of preparation 55 and acetic hydrazide, following a similar procedure to that described for preparation 88, except 2 equivalents of acetic hydrazide were used.

1H NMR (400 MHz, CDCl3): δ 1.41 (s, 9H), 1.58 (m, 1H), 1.72 (m, 1H), 3.02 (m, 1H), 3.20 (m, 1H), 3.24-3.44 (m, 5H), 3.52 (m, 2H), 4.24 (s, 2H), 7.38 (m, 2H), 7.50 (d, 2H);

LCMS: m/z APCl+ 422 [MH]+

Preparation 90: Ethyl 1-[4-(4-chlorophenyl)-5-methyl-4H-1,2,4-triazol-3-yl]piperidine-4-carboxylate

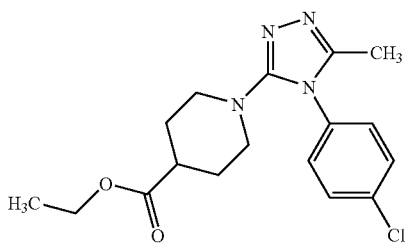

Trifluoroacetic acid (0.84 mL, 10.85 mmol) followed by acetic hydrazide (2.41 g, 32.6 mmol) were added to a solution of the compound of preparation 47 (7.38 g, 21.7 mmol) in tetrahydrofuran (100 mL), and the reaction was heated under reflux for 3 hours. The cooled mixture was partitioned between ethyl acetate and aqueous ammonia and the layers were separated. The organic phase was washed with brine, dried over MgSO4 and evaporated under reduced pressure. The crude product was triturated with ether to provide the title compound as a white solid, 5.04 g.

1H NMR (400 MHz, CDCl3): δ 1.22 (t, 3H), 1.60 (m, 2H), 1.83 (m, 2H), 2.22 (s, 3H), 2.38 (m, 1H), 2.82 (m, 2H), 3.28 (m, 2H), 4.14 (q, 2H), 7.25 (d, 2H), 7.55 (d, 2H); LCMS: m/z APCl+ 349 [MH]+

Preparation 91: Ethyl 1-[4-(4-chlorophenyl)-5-(2H-1,2,3-triazol-2-ylmethyl)-4H-1,2,4-triazol-3-yl]piperidine-4-carboxylate

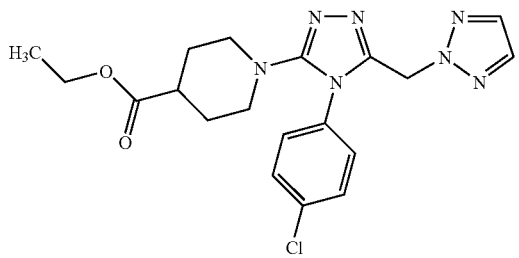

Trifluoroacetic acid (0.41 mL, 5.3 mmol) was added to a solution of the hydrazide of preparation 18 (3.6 g, 10.6 mmol) and the compound of preparation 47 (2.24 g, 15.9 mmol) in tetrahydrofuran (50 mL), and the reaction was heated under reflux for 15 hours. The cooled mixture was partitioned between ethyl acetate and brine and the layers were separated. The organic phase was filtered, dried over MgSO$_4$ and evaporated under reduced pressure to provide the title compound as a gum.

$^1$H NMR (400 MHz, CDCl$_3$): δ 1.21 (t, 3H), 1.58 (m, 2H), 1.82 (m, 2H), 2.38 (m, 1H), 2.86 (m, 2H), 3.38 (m, 2H), 4.12 (q, 2H), 5.59 (s, 2H), 7.15 (d, 2H), 7.40 (d, 2H), 7.50 (s, 2H).

Preparation 92: Ethyl 1-[4-(4-chlorophenyl)-5-methyl-4H-1,2,4-triazol-3-yl]-4-methylpiperidine-4-carboxylate

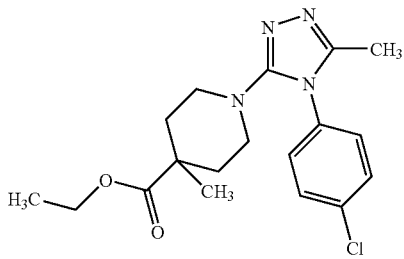

The title compound was obtained as a clear oil in 86% yield, from the compound of preparation 48 and acetic hydrazide, following the procedure described for preparation 91.

$^1$H NMR (400 MHz, CDCl$_3$): δ 1.18 (s, 3H), 1.23 (t, 3H), 1.40 (m, 2H), 2.00 (m, 2H), 2.23 (s, 3H), 2.90 (m, 2H), 3.18 (m, 2H), 4.14 (q, 2H), 7.26 (d, 2H), 7.57 (d, 2H); LCMS: m/z APCI$^+$ 363 [MH]$^+$

Preparation 93: tert-Butyl 4-[4-(4-chlorophenyl)-5-(methoxymethyl)-4H-1,2,4-triazol-3-yl]-2-methylpiperazine-1-carboxylate

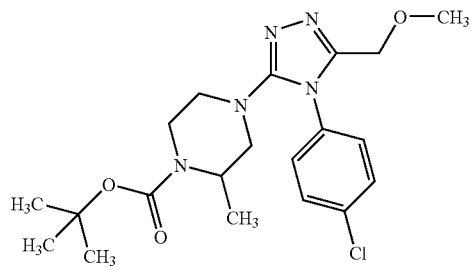

Methoxyacetic acid hydrazide (1.95 g, 18.75 mmol) was added to a solution of the compound of preparation 49 (4.80 g, 12.50 mmol) in tetrahydrofuran (200 mL) and the solution was stirred for 10 minutes. Trifluoroacetic acid (710 mg, 6.25 mmol) was added and the reaction was stirred at room temperature for 18 hours. The mixture was concentrated under reduced pressure and the crude product was purified by column chromatography using a silica gel cartridge and dichloromethane:methanol (100:0 to 90:10) as eluant, and repeated using ethyl acetate as eluant to afford the title compound as a foam, 1.84 g.

$^1$H NMR (400 MHz, CDCl$_3$): δ 0.98 (d, 3H), 1.42 (s, 9H), 2.82-3.05 (m, 4H), 3.24 (m, 1H), 3.34 (s, 3H), 3.80 (m, 1H), 4.18 (m, 1H), 4.34 (s, 2H), 7.40 (d, 2H), 7.64 (d, 2H); LCMS: m/z APCI$^+$ 363 [MH]$^+$

Preparation 94: tert-Butyl 4-[4-(4-chlorophenyl)-5-(methoxymethyl)-4H-1,2,4-triazol-3-yl]-3-methylpiperazine-1-carboxylate

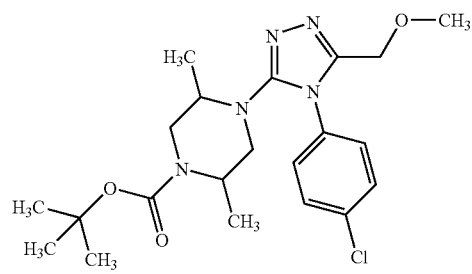

The title compound was obtained in 67% yield, from the compound of preparation 50, following a similar procedure to that described for preparation 93, except that the reaction was heated under reflux.

LCMS: m/z APCI$^+$ 363 [MH]$^+$

Preparation 95: tert-Butyl 4-[4-(4-chlorophenyl)-5-methyl-4H-1,2,4-triazol-3-yl]piperazine-1-carboxylate

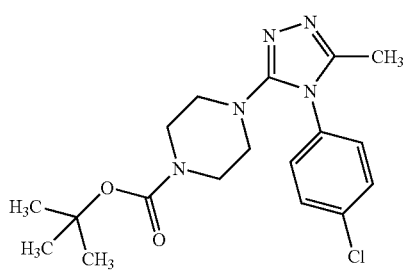

Acetic hydrazide (6.51 g, 88 mmol) was added to a solution of the compound of preparation 52 (32.46 g, 88 mmol) in n-butanol (250 mL) and the reaction was heated under reflux for 18 hours. The reaction was heated for a further 5 days under reflux with additional acetic hydrazide (36.5 g in total) added periodically. The cooled mixture was concentrated under reduced pressure and the residue was purified by column chromatography on silica gel using dichloromethane:methanol:0.88 ammonia (95:5:0.5) to provide the title compound as a white foam.

$^1$H NMR (400 MHz, CDCl$_3$): δ 1.42 (s, 9H), 2.24 (s, 3H), 3.01 (m, 4H), 3.38 (m, 4H), 7.25 (d, 2H), 7.54 (d, 2H). LCMS: m/z APCI$^+$ 378 [MH]$^+$

Preparation 96: 1-[4-(4-Chlorophenyl)-5-methyl-4H-1,2,4-triazol-3-yl]-4-phenylpiperidine-4-carbonitrile

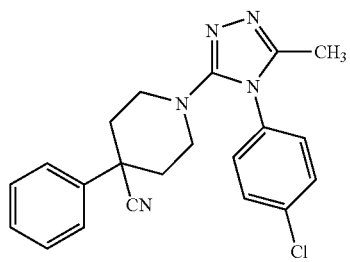

Acetic hydrazide (1.65 g, 22.3 mmol) was added to a solution of the compound of preparation 51 (3.3 g, 8.93 mmol) in n-butanol (5 mL) and the reaction was heated under reflux for 2 days. The cooled mixture was concentrated under reduced pressure and the residue was pre-adsorbed onto silica gel. It was then purified by column chromatography on silica gel using dichloromethane:methanol:0.88 ammonia (95:5:0.5), and the product was triturated with ethyl acetate to provide the title compound as a solid.

$^1$H NMR (400 MHz, CDCl$_3$): δ 1.97-2.16 (m, 4H), 2.24 (s, 3H), 3.35 (m, 2H), 3.42 (m, 2H), 7.22-7.45 (m, 7H), 7.56 (d, 2H); LCMS: m/z ES$^+$ 400 [MNa]$^+$

Preparation 97: tert-Butyl 4-[4-(4-chlorophenyl)-5-(methoxymethyl)-4H-1,2,4-triazol-3-yl]piperidine-1-carboxylate

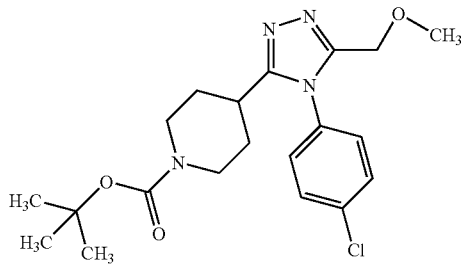

Trifluoroacetic acid (2.14 g, 18.83 mmol) was added to a solution of the compound of preparation 57 (7.0 g, 23.54 mmol) and 4-chloroaniline (3.60 g, 28.24 mmol) in toluene (50 mL), and the reaction mixture was heated under reflux for 18 hours. The cooled solution was concentrated under reduced pressure and the residue was purified by column chromatography using a silica gel cartridge and an elution gradient of dichloromethane:methanol (100:0 to 90:10) to afford the title compound as an oil, 4.25 g.

$^1$H NMR (400 MHz, CD$_3$OD): δ 1.45 (s, 9H), 1.67-1.83 (m, 4H), 2.68-2.83 (m, 3H), 3.32 (s, 3H), 4.08 (m, 2H), 4.39 (s, 2H), 7.46 (d, 2H), 7.63 (d, 2H); LCMS: m/z APCI$^+$ 407 [MH]$^+$

Preparation 98: tert-Butyl 4-[4-(4-chlorophenyl)-5-(hydroxymethyl)-4H-1,2,4-triazol-3-yl]piperidine-1-carboxylate

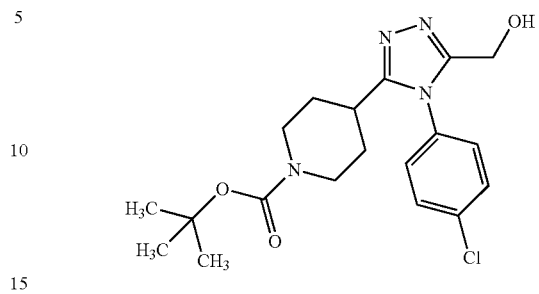

A mixture of the compound of preparation 59 (6.8 g, 24 mmol), 4-chloroaniline (4.3 g, 33.7 mmol) and trifluoroacetic acid (0.9 mL, 12 mmol) in toluene (40 mL) was stirred at 100° C. for 18 hours. The cooled mixture was evaporated under reduced pressure and the residue was dissolved in dichloromethane and washed with 2M sodium hydroxide solution. The organic solution was dried over MgSO$_4$ and concentrated under reduced pressure. The crude product was purified by column chromatography on silica gel using ethyl acetate:methanol:0.88 ammonia (95:5:0.5 to 90:10:1) to afford the title compound as an off-white solid, 7.1 g.

$^1$H NMR (400 MHz, CDCl$_3$): δ 1.42 (s, 9H), 1.75 (m, 2H), 1.82 (m, 2H), 2.59-2.76 (m, 3H), 3.00 (br s, 1H), 4.10 (m, 2H), 4.58 (s, 2H), 7.30 (d, 2H), 7.58 (d, 2H); LCMS: m/z APCI$^+$ 393 [MH]$^+$

Preparations 99 to 101

The compounds of the general formula shown below:

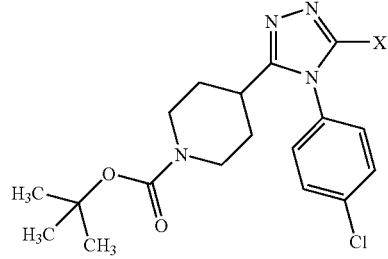

were prepared from the appropriate compound selected from preparations 60, 63 and 64 and 4-chloroaniline, following a similar procedure to that described for preparation 98.

| Prep. No. | Data |
|---|---|
| 99[A] | X=ethoxymethyl<br>$^1$H NMR(400MHz, CDCl$_3$): δ 1.09(t, 3H), 1.43(s, 9H), 1.68(m, 2H), 2.59-2.78(m, 3H), 3.42(q, 2H), 4.14(m, 2H), 4.42(s, 2H), 7.24(d, 2H), 7.57(d, 2H). LCMS: m/z APCI$^+$ 421[MH]$^+$ |
| 100[A] | X=2,2,2-trifluoroethyl<br>$^1$H NMR(400MHz, CDCl$_3$): δ 1.42(s, 9H), 1.72(m, 2H), 1.87(m, 2H), 2.58(m, 1H), 2.66(m, 2H), 3.45(q, 2H), 4.10(m, 2H), 7.19(d, 2H), 7.60(d, 2H). LCMS: m/z APCI$^+$ 445[MH]$^+$ |
| 101[B] | X=morpholin-4-ylmethyl<br>$^1$H NMR(400MHz, CDCl$_3$): δ 1.41(s, 9H), 1.65-1.96(m, 4H), 2.38(m, 4H), 2.58-2.77(m, 3H), 3.57(m, 4H), 4.08(m, 2H), 7.23(d, 2H), 7.56(d, 2H). LCMS: m/z APCI$^+$ 462[MH]$^+$ |

[A] = 0.8 eq. of trifluoroacetic acid were used.
[B] = 1 eq. of trifluoroacetic acid was used.

Preparation 102: tert-Butyl 2-[4-(4-chlorophenyl)-5-methyl-4H-1,2,4-triazol-3-yl]morpholine-4-carboxylate

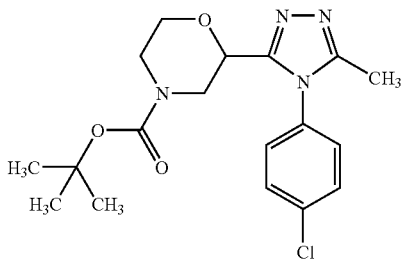

The title compound was obtained as an oil in 75% yield from the compound of preparation 72 and 4-chloroaniline, following a similar procedure to that described for preparation 98, except that 1 eq. of trifluoroacetic acid and 2 eq. of 4-chloroaniline were used.
LCMS: m/z APCI$^+$ 393 [MH]$^+$

Preparation 103: tert-Butyl 3-[4-(4-chloro-2-methylphenyl)-5-methyl-4H-1,2,4-triazol-3-yl]piperidine-1-carboxylate

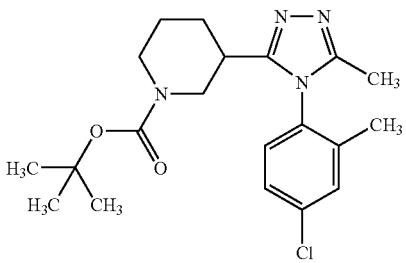

4-Chloro-2-methylaniline (3.78 g, 26.3 mmol) and p-toluene sulphonic acid (50 mg) were added to a solution of the oxadiazole of preparation 73 (2.33 g, 8.9 mmol) in xylene (10 mL) and the reaction was heated under reflux for 24 hours. The cooled reaction was purified directly by column chromatography on silica gel using ethyl acetate:methanol:dichloromethane (100:0:0 to 0:5:95). The product was azeotroped with dichloromethane to afford the title compound as a purple crystalline solid.
$^1$H NMR (400 MHz, CDCl$_3$): δ 1.39 (m, 10H), 1.69 (m, 1H), 1.80-1.97 (m, 2H), 1.98, 2.01 (s, 2×s, 3H), 2.17 (s, 3H), 2.32 (m, 1H), 2.59-3.17 (m, 2H), 4.10 (m, 2H), 7.05, 7.12 (m, 1H), 7.38 (t, 1H), 7.44 (d, 1H); LCMS: m/z APCI$^+$ 391 [MH]$^+$

Preparation 104: tert-Butyl 3-[4-(4-chloro-2-methylphenyl)-5-methyl-4H-1,2,4-triazol-3-yl]pyrrolidine-1-carboxylate

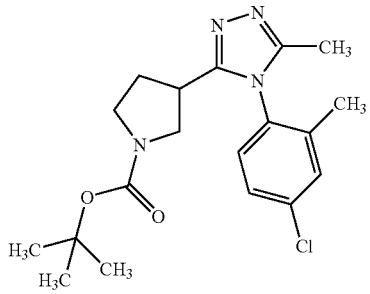

A mixture of the compound of preparation 74 (1.50 g, 5.92 mmol), trifluoroacetic acid (528 μL, 7.1 mmol) and 4-chloroaniline (1.68 g, 11.8 mmol) in toluene (20 mL) was heated at 110° C. for 18 hours. The cooled mixture was concentrated under reduced pressure and the residue was purified by column chromatography on silica gel using an elution gradient of dichloromethane:methanol:triethylamine (98:1.5:0.5 to 90:10:1 to 80:20:1) to provide the title compound, 810 mg.
$^1$H NMR (400 MHz, CDCl$_3$): δ 1.44 (s, 9H), 2.01 (s, 3H), 2.22 (m, 5H), 2.94-3.70 (m, 5H), 7.08 (m, 1H), 7.37-7.46 (m, 2H); LCMS: m/z APCI$^+$ 377 [MH]$^+$

Preparation 105: tert-Butyl 4-[4-(4-chloro-2-methoxyphenyl)-5-methyl-4H-1,2,4-triazol-3-yl]piperidine-1-carboxylate

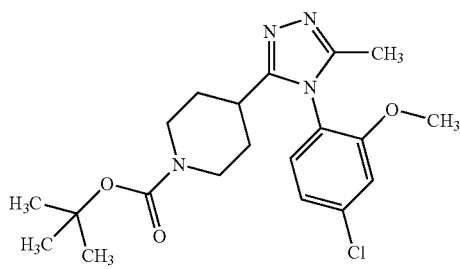

A mixture of the compound of preparation 1 (2 g, 7.5 mmol), 4-chloro-2-methoxyaniline (Bioorganic and Medicinal Chemistry Letters, 1999; 9(19); 2805-2810) (1.77 g, 11.2 mmol) and trifluoroacetic acid (0.29 mL, 3.7 mmol) in toluene (20 mL) was stirred at 85° C. for 5 hours. The cooled mixture was diluted with ethyl acetate and washed with 2M sodium hydroxide solution. The aqueous solution was extracted with dichloromethane (2×) and the combined organic solutions were dried over Na$_2$SO$_4$ and then concentrated under reduced pressure. The crude product was purified by column chromatography on silica gel using dichloromethane:methanol:0.88 ammonia (100:0:0 to 90:10:1) to afford the title compound, 2 g.
$^1$H NMR (400 MHz, CD$_3$OD): δ 1.46 (s, 9H), 1.63-1.84 (m, 4H), 2.18 (s, 3H), 2.59-2.81 (m, 3H), 3.86 (s, 3H), 4.05 (m, 2H), 7.20 (dd, 1H), 7.39 (m, 2H); LCMS: m/z APCI$^+$ 407 [MH]$^+$

Preparation 106: tert-Butyl 4-[4-(2,4-dichlorophenyl)-5-methyl-4H-1,2,4-triazol-3-yl]piperidine-1-carboxylate

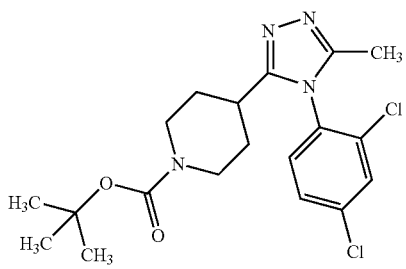

The title compound was prepared from the oxadiazole of preparation 1 and 2,4-dichloroaniline, following a similar procedure to that described for preparation 105, except that 2 equivalents of aniline were used.

$^1$H NMR (400 MHz, CDCl$_3$): δ 1.42 (s, 9H), 1.65-1.94 (m, 4H), 2.20 (s, 3H), 2.42 (m, 1H), 2.61-2.78 (m, 2H), 4.10 (m, 2H), 7.22 (d, 1H), 7.46 (d, 1H), 7.66 (s, 1H).

Preparations 107 to 116

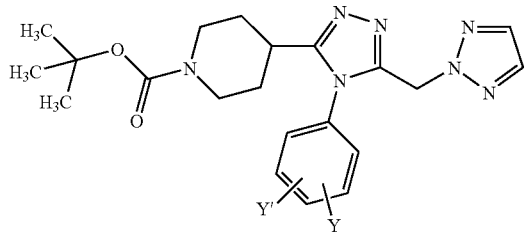

The appropriate aniline (Y'Y-PhNH$_2$) (1-1.1 eq.) followed by trifluoroacetic acid (0.5 eq.) were added to a solution of the compound of preparation 9 (1 eq.) in toluene (1.6 mlmmol$^{-1}$), and the reaction mixture was heated under reflux. The reaction was monitored by tlc and upon completion (45 minutes to 9 hours) the mixture was allowed to cool. The reaction was washed with dilute ammonia solution and brine, then dried over MgSO$_4$ and evaporated under reduced pressure. The crude product was purified by column chromatography on silica gel using dichloromethane:methanol (95:5) as eluant to afford the title compounds.

| Prep No | Data |
|---|---|
| 107 | Y=H; Y'=H;<br>$^1$H NMR(400MHz, CDCl$_3$): δ 1.42(s, 9H), 1.74(m, 2H), 1.87(m, 2H), 2.51-2.73(m, 3H), 4.08, (m, 2H), 5.63(s, 2H), 7.05(d, 2H), 7.40-7.55(5H, m).<br>LCMS: m/z ES$^+$ 432[MNa]$^+$ |
| 108 | Y=4-OCH$_3$; Y'=H;<br>$^1$H NMR(400MHz, CDCl$_3$): δ 1.42(s, 9H), 1.74(m, 2H), 1.86(m, 2H), 2.53-2.71(m, 3H), 3.84(s, 3H), 4.08(m, 2H), 5.61(s, 2H), 6.91(d, 2H), 6.96(d, 2H), 7.50(s, 2H)<br>LCMS: m/z ES$^+$ 462[MNa]$^+$ |
| 109 | Y=4-F; Y'=H;<br>$^1$H NMR(400MHz, CDCl$_3$): δ 1.42(s, 9H), 1.72(m, 2H), 1.89(m, 2H), 2.56(m, 1H), 2.65(m, 2H), 4.09(m, 2H), 5.62(s, 2H), 7.06(d, 1H), 7.13(m, 2H), 7.48(s, 2H).<br>LCMS: m/z ES$^+$ 428[MNa]$^+$ |
| 110$^A$ | Y=4-Br; Y'=H;<br>$^1$H NMR(400MHz, CDCl$_3$): δ 1.46(s, 9H), 1.74(m, 2H), 1.92(m, 2H), 2.59(m, 1H), 2.68(m, 2H), 4.12(m, 2H), 5.66(s, 2H), 6.98(d, 2H), 7.52(s, 2H), 7.61(d, 2H).<br>LCMS: m/z ES$^+$ 510[MNa]$^+$ |
| 111 | Y=4-CF$_3$; Y'=H;<br>1H NMR(400MHz, CDCl$_3$): δ 1.42(s, 9H), 1.74(m, 2H), 1.90(m, 2H), 2.54(m, 1H), 2.65(m, 2H), 4.10(m, 2H), 5.67(s, 2H), 7.21(d, 2H), 7.47(s, 2H), 7.73(d, 2H).<br>LCMS: m/z ES$^+$ 500[MNa]$^+$ |
| 112 | Y=4-CH$_3$; Y'=H;<br>$^1$H NMR(400MHz, CDCl$_3$): δ 1.42(s, 9H), 1.74(m, 2H), 1.87(m, 2H), 2.41(s, 3H), 2.54-2.73(m, 3H), 4.07(m, 2H), 6.94(d, 2H), 7.26(d, 2H), 7.52(s, 2H).<br>LCMS: m/z ES$^+$ 446[MNa]$^+$ |
| 113 | Y=4-CN; Y'=H;<br>$^1$H NMR(400MHz, CDCl$_3$): δ 1.42(s, 9H), 1.72(m, 2H), 1.92(m, 2H), 2.55(m, 1H), 2.66(m, 2H), 4.09(m, 2H), 5.68(s, 2H), 7.28(d, 2H), 7.52(s, 2H), 7.79(d, 2H).<br>LCMS: m/z ES$^+$ 435[MH]$^+$ |
| 114$^A$ | Y=4-Cl; Y'=2-CH$_3$;<br>$^1$H NMR(400MHz, CDCl$_3$): δ 1.45(s, 9H), 1.62-1.78(m, 3H), 1.86(s, 3H), 2.00(m, 1H), 2.41(m, 1H), 2.67(m, 2H), 4.01-4.18(m, 2H), 5.52(d, 1H), 5.67(d, 1H), 6.87(d, 1H), 7.25(d, 1H), 7.34(s, 1H), 7.48(s, 2H) LCMS: m/z ES$^+$ 458[MH]$^+$ |
| 115 | Y=4-Cl; Y'=3-F;<br>$^1$H NMR(400MHz, CDCl$_3$): δ 1.44(s, 9H), 1.73(m, 2H), 1.89(m, 2H), 2.57(m, 1H), 2.68(m, 2H), 4.11(m, 2H), 5.67(s, 2H), 6.84-6.92(m, 2H), 7.46-7.54(m, 3H).<br>LCMS: m/z ES$^+$ 462[MH]$^+$ |
| 116 | Y=4-Cl; Y'=3-Cl;<br>$^1$H NMR(400MHz, CDCl$_3$): δ 1.42(s, 9H), 1.73(m, 2H), 1.88(m, 2H), 2.55(m, 1H), 2.70(m, 2H), 4.08(m, 2H), 5.67(s, 2H), 6.97(d, 1H), 7.07(d, 1H), 7.52(s, 2H), 7.55(d, 1H). LCMS: m/z ES$^+$ 478[MH]$^+$ |

$^A$= 1.5 eq of aniline were used in the reaction.

Preparation 117: tert-Butyl 4-[4-(4-chlorophenyl)-5-({[(methylthio)carbonothioyl]oxy}methyl)-4H-1,2,4-triazol-3-yl]piperidine-1-carboxylate

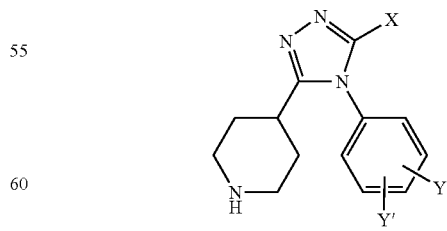

Sodium hydride (60% dispersion in mineral oil, 112 mg, 2.8 mmol) was added to an ice-cooled solution of the compound of preparation 98 (1 g, 2.55 mmol) in tetrahydrofuran (20 mL), and the solution was stirred for an hour at room temperature. Carbon disulfide (230 μL, 3.83 mmol) and then methyl iodide (238 μL, 3.83 mmol) were added, and the reaction was stirred at room temperature for a further 2 hours. Water (1 mL) was added, the mixture was concentrated under reduced pressure and the residue was partitioned between dichloromethane and aqueous sodium bicarbonate solution. The organic phase was dried over MgSO$_4$ and evaporated under reduced pressure. The crude product was purified by column chromatography on silica gel using an elution gradient of dichloromethane:methanol:0.88 ammonia (97:3:0.3 to 95:5:0.5) to afford the title compound as a pale yellow solid, 460 mg.

$^1$H NMR (400 MHz, CDCl$_3$): δ 1.42 (s, 9H), 1.77 (m, 2H), 1.90 (m, 2H), 2.54 (s, 3H), 2.58-2.77 (m, 3H), 4.13 (m, 2H), 5.56 (s, 2H), 7.20 (d, 2H), 7.57 (d, 2H); LCMS: m/z APCI$^+$ 483 [MH]$^+$

Preparations 118 to 137

4M Hydrochloric acid in dioxan (8 to 30 eq.) was added to a solution of the appropriate protected piperidine selected from preparations 76, 77, 80 to 85, and 105 to 116 (1 eq.) in methanol (9 to 22.5 mLmmol$^{-1}$) and the reaction was stirred at room temperature for between 1.5 and 3 hours. The mixture was concentrated under reduced pressure, the was residue partitioned between dichloromethane and 1M sodium hydroxide solution and the layers were separated. The organic solution was dried over MgSO$_4$ and evaporated under reduced pressure to afford the title compounds.

| Prep No | Data |
|---|---|
| 118[A] | Y=4-Cl; Y'=2-Cl; X=CH$_3$<br>$^1$H NMR(400MHz, CD$_3$OD): δ 2.05-2.22(m, 4H), 2.58(s, 3H), 3.10(m, 3H), 3.45(m, 2H), 7.78(d, 1H), 7.84(m, 1H), 8.00(s, 1H). LCMS: m/z APCl$^+$ 311[MH]$^+$ |
| 119[A] | Y=4-Cl; Y'=2-OCH$_3$; X=CH$_3$<br>$^1$H NMR(400MHz, CD$_3$OD): δ 2.00-2.22(m, 4H), 2.62(s, 3H), 3.08(m, 3H), 3.44(m, 2H), 3.95(s, 3H), 7.30(d, 1H), 7.50(s, 1H), 7.61(d, 1H). LCMS: m/z APCl$^+$ 307[MH]$^+$ |
| 120 | Y=4-Cl; Y'=H; X=2-oxo-1-pyrrolidinylmethyl<br>$^1$H NMR(400MHz, CDCl$_3$): δ 1.70-1.90(m, 4H), 1.98(m, 2H), 2.21(m, 2H), 2.58(m, 3H), 3.14(m, 2H), 3.45(t, 2H), 4.42(s, 2H), 7.18(d, 2H), 7.58 (d, 2H). LCMS: m/z APCl$^+$ 360[MH]$^+$ |
| 121 | Y=4-Cl; Y'=H; X=1,2,4-triazol-1-ylmethyl<br>$^1$H NMR(400MHz, CDCl$_3$): δ 1.80-1.98(m, 4H), 2.17-2.30(m, 1H), 2.62(m, 2H), 3.22(m, 2H), 5.38(s, 2H), 7.04(d, 2H), 7.52(d, 2H), 7.82(s, 1H), 8.03(s, 1H). LCMS: m/z APCl$^+$ 344[MH]$^+$ |
| 122 | Y=H; Y'=H; X=1,2,3-triazol-2-ylmethyl<br>$^1$H NMR(400MHz, CD$_3$OD): δ 1.83-1.96(m, 4H), 2.65-2.85(m, 3H), 3.25(d, 2H), 5.66(s, 2H), 7.23(d, 2H), 7.43-7.60(5H, m) LCMS: m/z ES$^+$ 310[MH]$^+$ |
| 123 | Y=4-F; Y'=H; X=1,2,3-triazol-2-ylmethyl<br>$^1$H NMR(400MHz, CDCl$_3$): δ 1.75(m, 2H), 1.85(m, 2H), 2.53(m, 3H), 3.16(d, 2H), 5.62(s, 2H), 7.02(d, 2H), 7.12(t, 2H), 7.49(s, 2H). LCMS: m/z ES$^+$ 328[MH]$^+$ |
| 124 | Y=4-Br; Y'=H; X=1,2,3-triazol-2-ylmethyl<br>$^1$H NMR(400MHz, CDCl$_3$): δ 1.79(m, 2H), 1.87(m, 2H), 2.54-2.65(m, 3H), 5.64(s, 2H), 6.93(d, 2H), 7.52(s, 2H), 7.59(d, 2H). LCMS: m/z ES$^+$ 388[MH]$^+$ |
| 125 | Y=4-Cl; Y'=3-F; X=1,2,3-triazol-2-ylmethyl<br>$^1$H NMR(400MHz, CDCl$_3$): δ 1.80(m, 2H), 1.93(m, 2H), 2.54-2.66(m, 3H), 3.22(d, 2H), 5.66(s, 2H), 6.80-6.88(m, 2H), 7.47-7.53(m, 3H). LCMS: m/z ES$^+$ 362[MH]$^+$ |
| 126 | Y=4-Cl; Y'=3-Cl; X=1,2,3-triazol-2-ylmethyl<br>$^1$H NMR(400MHz, CDCl$_3$): δ 1.80(m, 2H), 1.91(m, 2H), 2.52-2.66(m, 3H), 3.20(d, 2H), 5.66(s, 2H), 6.94(d, 1H), 7.07(d, 1H), 7.52(s, 2H), 7.54(d, 1H). LCMS: m/z ES$^+$ 378[MH]$^+$ |
| 127 | Y=4-CF$_3$; Y'=H; X=1,2,3-triazol-2-ylmethyl<br>$^1$H NMR(400MHz, CDCl$_3$): δ 1.76(m, 2H), 1.87(m, 2H), 2.56(m, 3H), 3.14(d, 2H), 5.66(s, 2H), 7.20(d, 2H), 7.46(s, 2H), 7.64(d, 2H). LCMS: m/z ES$^+$ 378[MH]$^+$ |
| 128 | Y=4-Cl; Y'=2-CH$_3$; X=1,2,3-triazol-2-ylmethyl<br>$^1$H NMR(400MHz, CDCl$_3$): δ 1.68-1.87(m, 5H), 1.91-2.15(m, 2H), 2.45(m ,1H), 1.55-1.72(m, 2H), 3.17(d, 1H), 3.28(d, 1H), 5.47(d, 1H), 5.64(d, 1H), 6.84(d, 1H), 7.20(d, 1H), 7.31(d, 1H), 7.46(s, 2H). LCMS: m/z ES$^+$ 358[MH]$^+$ |
| 129 | Y=4-CH$_3$; Y'=H; X=1,2,3-triazol-2-ylmethyl<br>$^1$H NMR(400MHz, CDCl$_3$): δ 1.74-1.98(m, 4H), 2.43(s, 3H), 2.55-2.68(m, 3H), 3.20(d, 2H), 5.60(s, 2H), 6.92(d, 2H), 7.24(d, 2H), 7.51(s, 2H). LCMS: m/z ES$^+$ 324[MH]$^+$ |
| 130 | Y=4-OCH$_3$; Y'=H; X=1,2,3-triazol-2-ylmethyl<br>$^1$H NMR(400MHz, CD$_3$OD): δ 1.72-1.79(m, 4H), 2.45(m, 2H), 2.65(m, 1H), 3.00(d, 2H), 3.82(s, 3H), 5.62(s, 2H), 7.00(d, 2H), 7.11(d, 2H), 7.57(s, 2H). LCMS: m/z ES$^+$ 340[MH]$^+$ |
| 131 | Y=4-CN; Y'=H; X=1,2,3-triazol-2-ylmethyl<br>$^1$H NMR(400MHz, CDCl$_3$): δ 1.61-1.95(m, 4H), 2.44-2.60(m, 3H), 3.16(m, 2H), 5.66(s, 2H), 7.21(d, 2H), 7.48(s, 2H), 7.76(d, 2H). LCMS: m/z ES$^+$ 335[MH]$^+$ |
| 132[A] | Y=4-Cl; Y'=H; X=tetrazol-1-ylmethyl<br>$^1$H NMR(400MHz, DMSO-d$_6$): δ 1.80-1.98(m, 4H), 2.80(m, 3H), 3.20(m, 2H), 3.56(s, 4H), 5.77(s, 2H), 7.43(d, 2H), 7.60(d, 2H), 8.75(br s, 1H), 8.94(br s, 1H), 9.18(s, 1H). LCMS: m/z ES$^+$ 345, 347[MH]$^+$ |
| 133[A] | Y=4-Cl; Y'=H; X=3-methylisoxazol-5-ylmethyl<br>$^1$H NMR(400MHz, CD$_3$OD): δ 2.05(m, 2H), 2.20(m, 2H), 3.00(m, 2H), 3.18(m, 1H), 3.38(m, 2H), 3.54(s, 3H), 4.25(s, 2H), 7.48(m, 2H), 7.58(d, 2H). LCMS: m/z APCl$^+$ 358[MH]$^+$ |
| 134[A] | Y=4-Cl; Y'=H; X=3-methyl-1,2,4-oxadiazol-5-ylmethyl<br>$^1$H NMR(400MHz, CD$_3$OD): δ 2.12(m, 4H), 2.34(s, 3H), 3.02(m, 2H), 3.15(m, 1H), 3.43(m, 2H), 3.64(s, 2H), 7.57(m, 2H), 7.68(d, 2H). LCMS: m/z APCl$^+$ 359[MH]$^+$ |
| 135 | Y=4-Cl; Y'=H; X=pyrimidin-2-yloxymethyl<br>$^1$H NMR(400MHz, CDCl$_3$): δ 2.05(m, 4H), 2.80-2.95(m, 3H), 3.46(m, 2H), 5.40(m, 2H), 6.98(m, 1H), 7.20-7.34(m, 1H), 7.41-7.58(m, 3H), 8.44(m, 2H). LCMS: m/z APCl$^+$ 371[MH]$^+$ |
| 136 | Y=4-Cl; Y'=H; X=2-piperidin-1-ylethyl<br>$^1$H NMR(400MHz, CDCl$_3$): δ 1.41(m, 2H), 1.56(m, 4H), 1.78-1.97(m, 4H), 2.20-2.40(m, 6H), 2.60-2.78(m, 5H), 3.22(m, 2H), 7.18(d, 2H), 7.57(d, 2H). LCMS: m/z APCl$^+$ 374[MH]$^+$ |
| 137 | Y=4-Cl; Y'=H; X=2-morpholin-4-ylethyl<br>$^1$H NMR(400MHz, CDCl$_3$): δ 1.70-1.90(m, 4H), 2.38(m, 4H), 2.58(m, 3H), 2.70(s, 4H), 3.14(m, 2H), 3.61(m, 4H), 7.18(d, 2H), 7.57(d, 2H). LCMS: m/z APCl$^+$ 376[MH]$^+$ |

[A] = The reaction mixture was evaporated under reduced pressure, prior to work-up to isolate the hydrochloride salt of the title compound.

Preparations 138 to 141

A solution of the appropriate protected piperidine selected from preparations 78 to 79, and 86 to 87 (1 eq.) in 2.2M methanolic hydrochloric acid (13 mlmmol$^{-1}$) was stirred at room temperature for 18 hours. The mixture was concentrated under reduced pressure and the residue was azeotroped with toluene. The crude product was partitioned between dichloromethane and 1M sodium hydroxide solution and the layers were separated. The organic solution was dried over MgSO$_4$ and evaporated under reduced pressure to afford the title compounds.

| Prep No | X | Data |
|---|---|---|
| 138 | 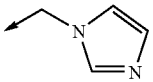 | ¹H NMR (400 MHz, CDCl₃): δ 1.78 (m, 2H), 1.80-1.98 (m, 2H), 2.56 (m, 3H), 3.16 (m, 2H), 5.12 (s, 2H), 6.75 (s, 1H), 6.84 (d, 2H), 7.00 (d, 2H), 7.50 (d, 2H). LCMS: m/z APCI⁺ 343 [MH]⁺ |
| 139 | 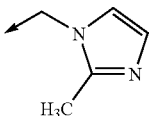 | ¹H NMR (400 MHz, CDCl₃): δ 1.74-1.97 (m, 4H), 2.04 (m, 3H), 2.48-2.64 (m, 3H), 3.19 (m, 2H), 5.00 (s, 2H), 6.46 (s, 1H), 6.82 (s, 2H), 6.85 (d, 2H), 7.48 (d, 2H). LCMS: m/z APCI⁺ 357 [MH]⁺ |
| 140[A] | 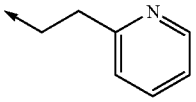 | ¹H NMR (400 MHz, CDCl₃): δ 2.06-2.19 (m, 4H), 3.03 (m, 2H), 3.18-3.22 (m, 1H), 3.30 (m, 2H), 3.44 (m, 2H), 3.60 (m, 2H), 7.77 (s, 4H), 7.98 (m, 1H), 8.05 (d, 1H), 8.58 (m, 1H), 8.78 (d, 1H). LCMS: m/z APCI⁺ 368 [MH]⁺ |
| 141[A] | 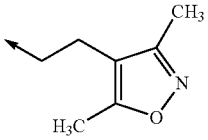 | ¹H NMR (400 MHz, CD₃OD): δ 1.99 (s, 3H), 2.12 (m, 7H), 2.78 (t, 2H), 2.97 (t, 2H), 3.00-3.18 (m, 3H), 3.43 (m, 2H), 7.54 (d, 2H), 7.78 (d, 2H). LCMS: m/z APCI⁺ 386 [MH]⁺ |

A = The reaction mixture was evaporated under reduced pressure, and azeotroped with toluene. The product was triturated with ethyl acetate, filtered and dried to afford the hydrochloride salt of the title compound.

Preparation 142: 4-[4-(4-Chlorophenyl)-5-(methoxymethyl)-4H-1,2,4-triazol-3-yl]-piperidine

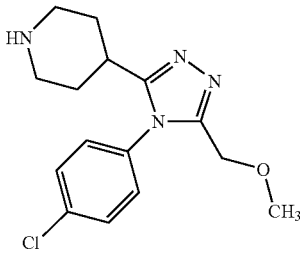

4M Hydrochloric acid in dioxan (60 mL) was added to a solution of the compound of preparation 97 (3.75 g, 9.22 mmol) in dioxan (50 mL) and the reaction was stirred at room temperature for 3 hours. The mixture was evaporated under reduced pressure and the residue was re-dissolved in dichloromethane and washed with aqueous ammonia, then brine. The organic solution was dried over MgSO₄ and evaporated under reduced pressure. The crude product was purified by column chromatography using a silica gel cartridge and dichloromethane:methanol:0.88 ammonia (90:10:1) as eluant to afford the title compound, 1.99 g.

¹H NMR (400 MHz, CDCl₃): δ 1.80-1.98 (m, 4H), 2.57-2.70 (m, 3H), 3.20 (m, 2H), 3.25 (s, 3H), 4.38 (s, 2H), 7.22 (d, 2H), 7.57 (d, 2H). LCMS: m/z APCI⁺ 307 [MH]⁺

Preparation 143: 4-[4-(4-Chlorophenyl)-5-(ethoxymethyl)-4H-1,2,4-triazol-3-yl]piperidine hydrochloride

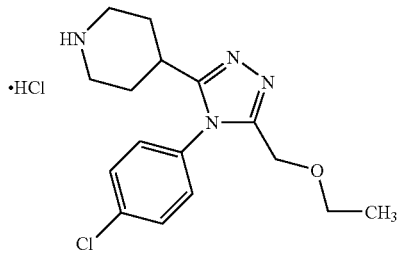

4M Hydrochloric acid in dioxan (20 mL) was added to a solution of the compound of preparation 99 (990 mg, 2.35 mmol) in dioxan (20 mL) and the reaction was stirred at room temperature for 18 hours. The mixture was evaporated under reduced pressure, and the residue was azeotroped with dichloromethane to afford the title compound, 910 mg.

¹H NMR (400 MHz, CD₃OD): δ 1.02 (t, 3H), 1.80 (m, 4H), 2.55 (m, 2H), 2.76 (m, 1H), 3.05 (m, 2H), 3.38 (q, 2H), 4.42 (s, 2H), 7.45 (d, 2H), 7.63 (d, 2H); LCMS: m/z APCI⁺ 321 [MH]⁺

Preparation 144: 1-[4-(4-Chlorophenyl)-5-methyl-4H-1,2,4-triazol-3-yl]piperazine dihydrochloride

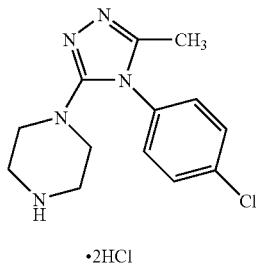

·2HCl

4M Hydrochloric acid in dioxan (13.75 mL) was added to a solution of the compound of preparation 95 (4.12 g, 110 mmol) in dichloromethane (50 mL) and the reaction was stirred at room temperature for 30 minutes. The mixture was evaporated under reduced pressure and dried in vacuo to afford the title compound as a white solid, 3.8 g.

$^1$H NMR (400 MHz, CDCl$_3$): δ 2.23 (s, 3H), 2.80 (m, 4H), 3.05 (m, 4H), 7.25 (d, 2H), 7.50 (d, 2H).

Preparation 145: 1-[4-(4-Chlorophenyl)-5-methyl-4H-1,2,4-triazol-3-yl]piperidin-4-amine dihydrochloride

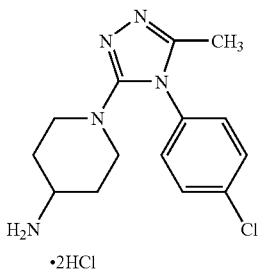

·2HCl

A suspension of the compound of preparation 88 (32.3 g, 82.5 mmol) in methanol (250 mL) and 4N hydrochloric acid in dioxan (40 mL) was warmed to 50° C. for 3 hours. The mixture was concentrated under reduced pressure and the residue was slurried in tetrahydrofuran (50 mL). The resulting solid was filtered off and dried in vacuo to provide the title compound.

$^1$H NMR (400 MHz, CD$_3$OD): δ 1.65 (m, 2H), 1.96 (m, 2H), 2.36 (s, 3H), 3.07 (m, 2H), 3.36 (m, 1H), 3.47 (m, 2H), 7.66 (d, 2H), 7.75 (d, 2H). LCMS: m/z APCI$^+$ 292 [MH]$^+$

Preparation 146: 3-[4-(4-Chloro-2-methylphenyl)-5-methyl-4H-1,2,4-triazol-3-yl]piperidine

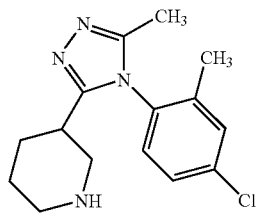

4M Hydrochloric acid (5 mL) was added to a solution of the compound of preparation 103 (846 mg, 2.16 mmol) in dioxan (10 mL) and the reaction was stirred at room temperature for 18 hours. Tlc analysis showed that starting material remained, so additional 4M hydrochloric acid in dioxan (5 mL) was added and the reaction was stirred for a further hour at room temperature. The reaction mixture was then concentrated under reduced pressure and the crude product was purified by column chromatography on silica gel using dichloromethane:methanol:0.88 ammonia (90:10:1). The product was azeotroped with dichloromethane and ether to afford the title compound as an off-white foam.

$^1$H NMR (400 MHz, CDCl$_3$): δ 1.49 (m, 1H), 1.68-1.93 (m, 3H), 1.97 (s, 3H), 2.16 (s, 3H), 2.59 (m, 1H), 2.80 (m, 1H), 3.03 (m, 1H), 3.16 (m, 1H), 7.06 (2×d, 1H), 7.35 (2×m, 1H), 7.42 (2×d, 1H); LCMS: m/z APCI$^+$ 291 [MH]$^+$

Preparation 147: 4-(4-Chloro-2-methylphenyl)-3-methyl-5-pyrrolidin-3-yl-4H-1,2,4-triazole

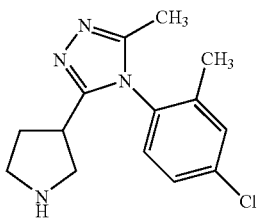

A solution of the compound of preparation 104 in 4M hydrochloric acid in dioxan (20 mL) was stirred at room temperature for 4 hours. The mixture was partitioned between ethyl acetate and 2N sodium hydroxide solution, and the layers were separated. The organic solution was dried over MgSO$_4$ and evaporated under reduced pressure to provide the title compound.

$^1$H NMR (400 MHz, CDCl$_3$): δ 2.00 (m, 5H), 2.20 (m, 5H), 2.80-3.02 (m, 2H), 3.10-3.27 (m, 1H), 7.05 (d, 1H), 7.38 (d, 1H), 7.41 (s, 1H); LCMS: m/z APCI$^+$ 277 [MH]$^+$

Preparation 148: 1-[4-(4-Chlorophenyl)-5-(methoxymethyl)-4H-1,2,4-triazol-3-yl]-1,4-diazepane

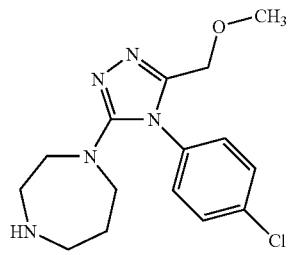

4M Hydrochloric acid in dioxan (25 mL) was added to a solution of the compound of preparation 89 (5.45 g, 12.93 mmol) in dioxan (30 mL) and the reaction was stirred at room temperature for 18 hours. The mixture was concentrated under reduced pressure and the residue was partitioned between water and ether. The layers were then separated, the aqueous phase was basified using sodium hydroxide and the solution was extracted with dichloromethane (3×). The combined organic extracts were dried over MgSO$_4$ to afford the title compound as a foam, 3.84 g.

$^1$H NMR (400 MHz, CD$_3$OD): δ 1.78 (m, 2H), 2.84 (m, 4H), 3.21 (s, 3H), 3.30 (m, 4H), 4.24 (s, 2H), 7.50 (d, 2H), 7.60 (d, 2H); LCMS: m/z APCI$^+$ 322 [MH]$^+$

Preparation 149: 1-[4-(4-Chlorophenyl)-5-(methoxymethyl)-4H-1,2,4-triazol-3-yl]-2-methylpiperazine

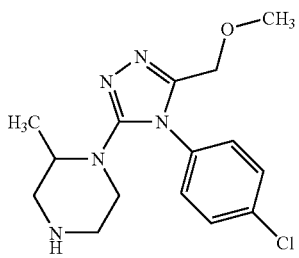

The title compound was obtained as a yellow oil in 95% yield from the compound of preparation 94, following the procedure described for preparation 148.

$^1$H NMR (400 MHz, CDCl$_3$): δ 1.14 (d, 3H), 2.10 (br s, 1H), 2.60 (m, 1H), 2.82 (m, 2H), 2.97 (m, 1H), 3.07 (m, 2H), 3.35 (s, 3H), 4.28 (d, 1H), 4.40 (d, 1H), 7.38 (d, 2H), 7.50 (d, 2H); LCMS: m/z APCI$^+$ 322 [MH]$^+$

Preparation 150: 1-[4-(4-Chlorophenyl)-5-(methoxymethyl)-4H-1,2,4-triazol-3-yl]-3-methylpiperazine

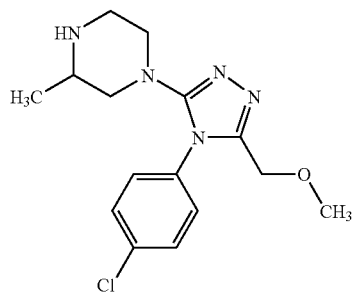

Trifluoroacetic acid (25 mL) was added to an ice-cooled solution of the compound of preparation 93 (2.80 g, 6.63 mmol) in dichloromethane (25 mL) and the solution was stirred at room temperature for an hour. The mixture was concentrated under reduced pressure and the residue was re-dissolved in ethyl acetate, then washed with 1N sodium hydroxide solution. The organic solution was dried over MgSO$_4$ and evaporated under reduced pressure. The crude product was purified by column chromatography using a silica gel cartridge and an elution gradient of dichloromethane:methanol:0.88 ammonia (100:0:0 to 90:10:1) to afford the title compound as an oil, 780 mg.

$^1$H NMR (400 MHz, CDCl$_3$): δ 1.19 (d, 3H), 2.98 (m, 2H), 3.02-3.23 (m, 5H), 3.36 (s, 3H), 4.34 (s, 2H), 7.40 (d, 2H), 7.52 (d, 2H); LCMS: m/z APCI$^+$ 322 [MH]$^+$

Preparation 151: 4-[4-(4-Chloro-2-methylphenyl)-5-methyl-4H-1,2,4-triazol-3-yl]piperidine

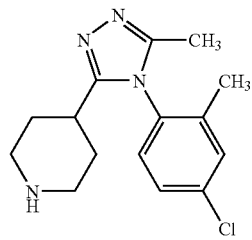

A mixture of the compound of preparation 1 (3 g, 11.2 mmol), 4-chloro-2-methylaniline (2.4 g, 16.8 mmol) and trifluoroacetic acid (0.8 mL, 11.2 mmol) in toluene (30 mL) was stirred at room temperature for 110° C. for 18 hours. The cooled mixture was concentrated under reduced pressure, 2M sodium hydroxide solution (10 mL) added and the mixture was azeotroped with toluene. The crude product was purified by column chromatography on silica gel using dichloromethane:methanol:0.88 ammonia (95:5:0.5 to 80:20:3) to afford the title compound as an off-white foam, 1.45 g.

$^1$H NMR (400 MHz, CD$_3$OD): δ 1.81 (m, 2H), 1.92 (m, 2H), 2.00 (s, 3H), 2.19 (s, 3H), 2.60-2.78 (m, 3H), 3.20 (m, 2H), 7.38 (d, 1H), 7.46 (d, 1H), 7.59 (s, 1H); LCMS: m/z APCI$^+$ 291 [MH]$^+$

Preparation 152: 4-[4-(4-Chloro-2-fluorophenyl)-5-methyl-4H-1,2,4-triazol-3-yl]piperidine ditrifluoroacetate

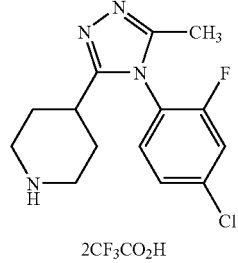

2CF$_3$CO$_2$H

A mixture of the compound of preparation 1 (900 mg, 3.4 mmol), 4-chloro-2-fluoroaniline (109.1 mg, 0.75 mmol) and trifluoroacetic acid (288 µL, 3.74 mmol) in toluene (8 mL) was stirred at 110° C. for 72 hours. The cooled mixture was concentrated under reduced pressure, 0.88 ammonia added and the mixture was concentrated under reduced pressure. The residue was azeotroped with toluene and the crude product was purified by column chromatography on silica gel using an elution gradient of dichloromethane:methanol:0.88 ammonia (90:10:1 to 80:20:3) to afford the title compound as an off-white foam, 985 mg.

$^1$H NMR (400 MHz, CDCl$_3$): δ 2.02-2.30 (m, 7H), 2.80 (m, 1H), 3.10 (m, 2H), 3.59 (m, 2H), 3.86 (m, 1H), 7.26 (m, 1H), 7.40 (m, 2H), 9.34 (br s, 1H), 10.10 (br s, 1H); LCMS: m/z APCI$^+$ 295 [MH]$^+$

Preparation 153: 4-{4-(4-Chlorophenyl)-5-[(2,2,2-trifluoroethoxy)methyl]-4H-1,2,4-triazol-3-yl}piperidine

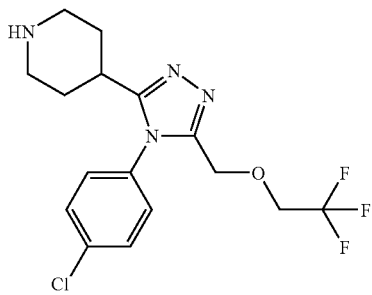

Trifluoroacetic acid (2.49 g, 21.8 mmol) was added to a solution of 4-chloroaniline (3.63 g, 28.4 mmol) and the compound of preparation 58 (8.0 g, 21.9 mmol) in toluene (50 mL), and the reaction heated was under reflux for 48 hours. Tlc analysis showed that starting material remained, so additional trifluoroacetic acid (8 mL) was added and the reaction was heated for a further 4 hours under reflux. The cooled mixture was extracted with water, the aqueous solution was basified using potassium hydroxide and then extracted with dichloromethane (4×100 mL). The combined organic extracts were dried over MgSO$_4$ and evaporated under reduced pressure. The crude product was purified by column chromatography using a silica gel cartridge and an elution gradient of dichloromethane:methanol:0.88 ammonia (100:0:0 to 85:15:1.5) to give the title compound, 4.34 g.

$^1$H NMR (400 MHz, CDCl$_3$): δ 1.86-2.04 (m, 4H), 2.78 (m, 3H), 3.37 (m, 2H), 3.82 (q, 2H), 4.22-4.41 (br s, 1H), 4.58 (s, 2H), 7.22 (d, 2H), 7.58 (d, 2H); LCMS: m/z ES$^+$ 375.1 [MH]$^+$

Preparation 154: 4-{4-(4-Chlorophenyl)-5-[(trifluoromethoxy)methyl]-4H-1,2,4-triazol-3-yl}piperidine

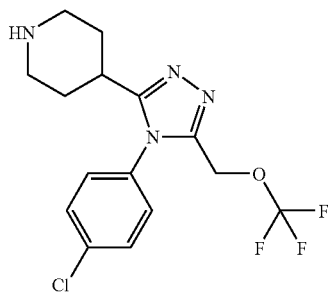

Hydrogen fluoride-pyridine (0.35 mL, 13.2 mmol), followed by a solution of the compound of preparation 117 (160 mg, 0.33 mmol) in dichloromethane (1 mL) were added to a solution of 1,3-dibromo-2,4-dimethylhydantoin (283 mg, 1.0 mmol) in dichloromethane (5 mL) at −78° C. The reaction was allowed to warm to room temperature over 30 minutes then stirred for a further hour. The mixture was washed with 1N sodium hydroxide solution, dried over MgSO$_4$ and evaporated under reduced pressure. The crude product was purified by column chromatography on silica gel using dichloromethane:methanol:0.88 ammonia (90:10:1) as eluant to provide the title compound as a yellow oil, 45 mg.

LCMS: m/z APCI$^+$ 361 [MH]$^+$

Preparation 155: 4-[4-(4-Chlorophenyl)-5-methyl-4H-1,2,4-triazol-3-yl]benzonitrile

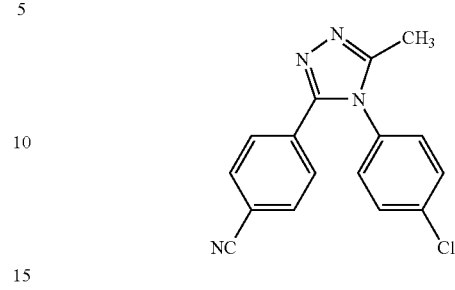

Trifluoroacetic acid (600 μL, 8.1 mmol) was added to a suspension of 4-chloroaniline (2.1 g, 16.2 mmol) and 4-(5-methyl-1,3,4-oxadiazol-2-yl)benzonitrile (Journal für Praktische Chemie, 1994; 336(8); 678-85) (3.0 g, 16.2 mmol) in tetrahydrofuran (50 mL) and the reaction was heated at reflux for 22 hours. The cooled mixture was partitioned between ethyl acetate (300 mL) and 20% aqueous 0.88 ammonia (120 mL), and then the layers were separated. The organic phase was dried over MgSO$_4$ and evaporated under reduced pressure. The residue was triturated with ether and a minimum volume of ethyl acetate to afford the title compound as a white crystalline solid, 2.82 g.

$^1$H NMR (400 MHz, CDCl$_3$): δ 2.38 (s, 3H), 7.19 (d, 2H), 7.55 (m, 4H), 7.60 (d, 2H);

LCMS: m/z ES$^+$ 295 [MH]$^+$

Preparation 156: 4-[4-(4-Chlorophenyl)-5-methyl-4H-1,2,4-triazol-3-yl]benzoic acid

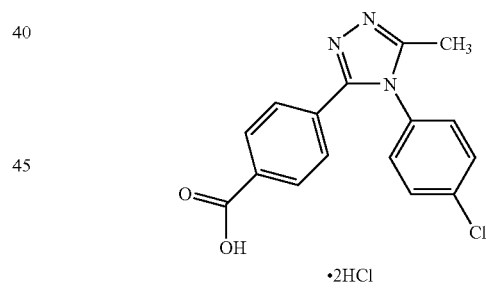

A solution of potassium hydroxide (2.6 g, 46.0 mmol) in water (10 mL) was added to a solution of the compound of preparation 155 (2.7 g, 9.2 mmol) in ethylene glycol dimethyl ether (40 mL) and the reaction was heated under reflux for 18 hours. Ethanol (50 mL) was added and the reaction was heated under reflux for a further 72 hours. The cooled mixture was acidified to pH 6 and concentrated under reduced pressure. The residue was extracted using dichloromethane:methanol:0.88 ammonia (84:14:2), the suspension was then filtered and the filtrate was evaporated under reduced pressure. The product was triturated with ether, filtered off and dried to afford the title compound as a white solid.

$^1$H NMR (400 MHz, CD$_3$OD): δ 2.38 (s, 3H), 7.19 (m, 4H), 7.58 (d, 2H), 7.90 (d, 2H);

LCMS: m/z ES$^-$ 312 [M-H]$^-$

Preparation 157: 4-[4-(4-Chlorophenyl)-5-methyl-4H-1,2,4-triazol-3-yl]benzoyl chloride

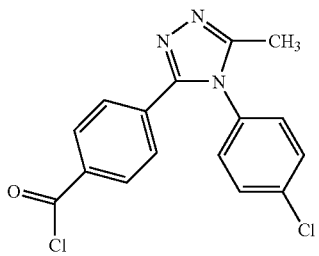

Oxalyl chloride (3 mL, 32 mmol) followed by N,N-dimethylformamide (5 drops) were added to a solution of the acid of preparation 156 (2 g, 6.4 mmol) in dichloromethane (200 mL) and the mixture was stirred at room temperature for 2 hours. The mixture was filtered, the filtrate was evaporated under reduced pressure and the residue was azeotroped with dichloromethane (3×200 mL) to afford the title compound as an orange oil, 2.01 g.

$^1$H NMR (400 MHz, CDCl$_3$): δ 2.78 (s, 3H), 7.58 (d, 2H), 7.63 (d, 2H), 7.74 (m, 2H), 8.06 (d, 2H).

Preparation 158: 1-[4-(4-Chlorophenyl)-5-methyl-4H-1,2,4-triazol-3-yl]piperidine-4-carboxylic acid

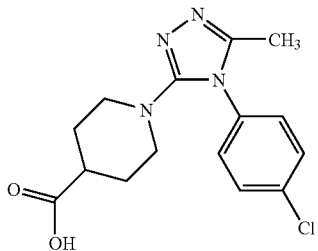

A solution of the ester of preparation 90 (4 g, 10.4 mmol) and 4N sodium hydroxide (13 mL, 52 mmol) in dioxan (20 mL) was stirred at room temperature for 2 hours. The mixture was partitioned between water and ethyl acetate and the phases were separated. The aqueous layer was acidified to pH 4 using 2N hydrochloric acid, the resulting precipitate was filtered off and washed with water. The solid was triturated with ether, filtered and dried in vacuo to afford the title compound as a white solid.

$^1$H NMR (400 MHz, CD$_3$OD): δ 1.52-1.61 (m, 2H), 1.81 (m, 2H), 2.21 (s, 3H), 2.40 (m, 1H), 2.81 (m, 2H), 3.21-3.36 (m, 2H), 7.47 (d, 2H), 7.62 (d, 2H).

Preparation 159: 1-[4-(4-Chlorophenyl)-5-(2H-1,2,3-triazol-2-ylmethyl)-4H-1,2,4-triazol-3-yl]piperidine-4-carboxylic acid

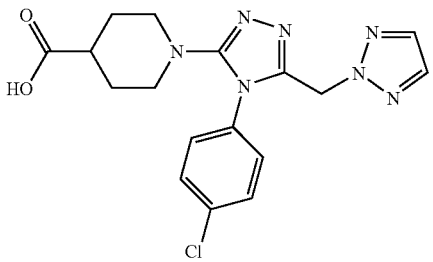

The title compound was obtained as a white solid, from the ester of preparation 91, following a similar procedure to that described for preparation 158, except that 10 eq. of sodium hydroxide were used in the reaction.

$^1$H NMR (400 MHz, CD$_3$OD): δ 1.48-1.60 (m, 2H), 1.81 (m, 2H), 2.40 (m, 1H), 2.82 (m, 2H), 3.32 (m, 2H), 5.64 (s, 2H), 7.30 (d, 2H), 7.50 (d, 2H), 7.58 (s, 2H); LCMS: m/z APCI$^+$ 388 [MH]$^+$

Preparation 160: 1-[4-(4-Chlorophenyl)-5-methyl-4H-1,2,4-triazol-3-yl]-4-methylpiperidine-4-carboxylic acid

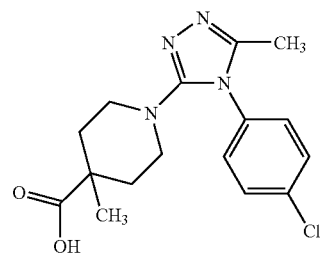

A mixture of the ester of preparation 92 (1.45 g, 4.0 mmol) and 4N sodium hydroxide solution (5 mL, 20 mmol) in dioxan (50 mL) was stirred under reflux for 16 hours. Tlc analysis showed that starting material remained, so additional sodium hydroxide (4N, 5 mL, 20 mmol) was added, and the reaction was heated under reflux for a further 18 hours. The cooled mixture was partitioned between ethyl acetate and water, and the layers were separated. The aqueous phase was acidified to pH 3.5 using 2N hydrochloric acid and extracted with ethyl acetate (2×). These combined organic extracts were dried over MgSO$_4$ and evaporated under reduced pressure. The product was triturated with ethyl acetate. The resulting solid was filtered off and dried to provide the title compound as a white solid, 800 mg.

$^1$H NMR (400 MHz, CD$_3$OD): δ 1.18 (s, 3H), 1.38 (m, 2H), 1.99 (m, 2H), 2.21 (s, 3H), 2.92 (m, 2H), 3.16 (m, 2H), 7.49 (d, 2H), 7.63 (d, 2H). LCMS: m/z APCI$^+$ 335 [MH]$^+$

Preparation 161: N-(4-Chlorophenyl)-2-(2H-1,2,3-triazol-2-ylacetyl)hydrazinecarbothioamide

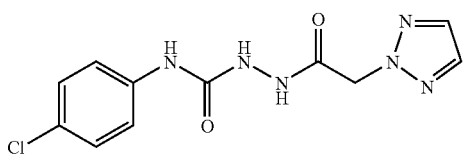

4-Chlorophenylisothiocyanate (8.58 g, 50.6 mmol) was added portionwise to a suspension of the hydrazide of preparation 18 (7.0 g, 50.6 mmol) in ethanol (200 mL) and the mixture was stirred at room temperature for 72 hours. The resulting precipitate was filtered off, washed with ether and dried to afford the title compound as a white solid, 14.5 g.

$^1$H NMR (400 MHz, CD$_3$OD): δ 5.30 (s, 2H), 7.36 (d, 2H), 7.44 (d, 2H), 7.78 (s, 2H).

Preparation 162: 4-(4-Chlorophenyl)-5-(2H-1,2,3-triazol-2-ylmethyl)-2,4-dihydro-3H-1,2,4-triazole-3-thione

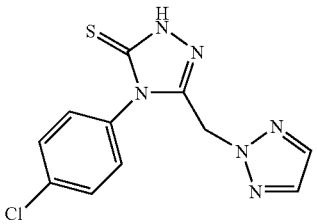

A solution of the compound of preparation 161 (14.5 g, 46.5 mmol) and 2M sodium hydroxide solution (232 mL, 465 mmol) in ethanol (36 mL) was stirred at 80° C. for 18 hours. The cooled mixture was acidified to pH 9 using concentrated hydrochloric acid, then it was extracted with dichloromethane (6×250 mL). The combined organic solutions were evaporated under reduced pressure to afford the title compound as a white solid, 7.5 g.

$^1$H NMR (400 MHz, CDCl$_3$): δ 5.54 (s, 2H), 7.05 (d, 2H), 7.42 (d, 2H), 7.58 (s, 2H).

Preparation 163: 2-{[4-(4-Chlorophenyl)-5-(methylthio)-4H-1,2,4-triazol-3-yl]methyl}-2H-1,2,3-triazole

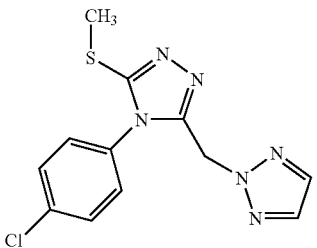

Potassium tert-butoxide (2.9 g, 25.6 mmol) was added to a solution of the compound of preparation 162 (7.5 g, 25.6 mmol) in tetrahydrofuran (250 mL) and the suspension was stirred at room temperature for 30 minutes. Methyl p-toluenesulphonate (4.8 g, 25.7 mmol) was added and the mixture was heated under reflux for 45 minutes, then at room temperature for a further 2 hours. The mixture was diluted with dichloromethane (1000 mL), washed with saturated ammonium chloride solution (300 mL) and brine (300 mL) then it was dried over MgSO$_4$ and evaporated under reduced pressure. The crude material was purified by column chromatography on silica gel using dichloromethane:methanol (85:15) as eluant to provide the title compound, 4.9 g.

$^1$H NMR (400 MHz, CDCl$_3$): δ 2.70 (s, 3H), 5.64 (s, 2H), 7.02 (d, 2H), 7.41 (d, 2H), 7.54 (s, 2H). LCMS: m/z ES$^+$ 329 [MNa]$^+$

Preparation 164: 2-{[4-(4-Chlorophenyl)-5-(methylsulfonyl)-4H-1,2,4-triazol-3-yl]methyl}-2H-1,2,3-triazole

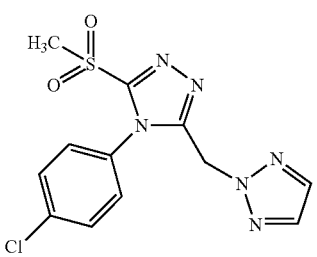

Meta-chloroperbenzoic acid (3.4 g, 19.56 mmol) was added to a solution of the compound of preparation 163 (1.5 g, 4.90 mmol) in dichloromethane (60 mL) and the reaction was stirred at room temperature for 18 hours. The mixture was diluted with dichloromethane, then washed with saturated sodium bicarbonate solution (300 mL) and brine (200 mL). The organic solution was dried over Na$_2$SO$_4$ and concentrated under reduced pressure. The residual solid was washed with ethanol, then dried in vacuo to afford the title compound as a white solid, 1.40 g.

$^1$H NMR (400 MHz, CDCl$_3$): δ 3.46 (s, 3H), 5.69 (s, 2H), 7.18 (d, 2H), 7.41 (d, 2H), 7.57 (s, 2H); LCMS: m/z ES$^+$ 361 [MNa]$^+$

Preparation 165: 4-Chloro-2-ethoxynitrobenzene

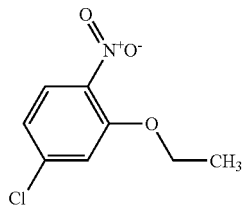

Sodium ethoxide (21% in ethanol, 8.6 mL, 26 mmol) was added dropwise to a solution of 4-chloro-2-fluoronitrobenzene (3 g, 17.1 mmol) in ethanol (20 mL), and once addition was complete the reaction was stirred for a further hour. The mixture was concentrated under reduced pressure, the residue was diluted with ethyl acetate, and the solution was washed with water (×2), then brine. The solution was dried over MgSO$_4$ and evaporated under reduced pressure to afford the title compound as a solid, 3.45 g.

$^1$H NMR (400 MHz, CDCl$_3$): δ 1.49 (t, 3H), 4.19 (q, 2H), 7.00 (d, 1H), 7.05 (s, 1H), 7.81 (d, 1H).

Preparation 166: 4-Chloro-2-ethoxyaniline

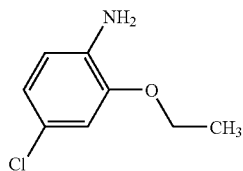

A mixture of the nitro compound of preparation 165 (3.30 g, 16.4 mmol), iron powder (2.7 g, 49 mmol) and calcium chloride (810 mg, 7.4 mmol) in water (5 mL) and ethanol (30 mL) was heated under reflux for 3.5 hours. The cooled mixture was filtered through Celite® and the filtrate was concentrated under reduced pressure. The residue was partitioned between water and ethyl acetate, the layers were separated and the organic phase was washed further with brine. The solution was dried over MgSO$_4$ and evaporated under reduced pressure. The crude product was purified by column chromatography on silica gel using an elution gradient of pentane: ethyl acetate (100:0 to 0:100) to afford the title compound as an oil, 2.4 g.

¹H NMR (400 MHz, CDCl₃): δ 1.42 (t, 3H), 402 (q, 2H), 6.61 (d, 1H), 6.76 (m, 2H).

Preparation 167:
1-(5-Chloro-2-nitrobenzyl)pyrrolidine

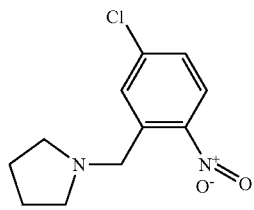

Pyrrolidine (4 mL, 48.5 mmol) was added to a solution of 5-chloro-2-nitrobenzaldehyde (6 g, 32.2 mmol) in dichloromethane (150 mL) and the solution was stirred at room temperature for 30 minutes. The solution was then cooled in ice, and sodium triacetoxyborohydride (10.3 g, 48.5 mmol) was added portionwise. Once addition was complete, the reaction was stirred at room temperature for 4 hours. The reaction was washed with sodium carbonate solution, dried over MgSO₄ and evaporated under reduced pressure. The residual oil was purified by column chromatography on silica gel using ethyl acetate:pentane (86:14) to afford the title compound as a pale yellow solid, 6.3 g.

¹H NMR (400 MHz, CDCl₃): δ 1.82 (m, 4H), 2.58 (m, 2H), 3.98 (s, 2H), 7.37 (d, 1H), 7.80 (s, 1H), 7.87 (d, 1H). LCMS: m/z APCI⁺ 241 [MH]⁺

Preparation 168:
4-Chloro-2-(pyrrolidin-1-ylmethyl)aniline

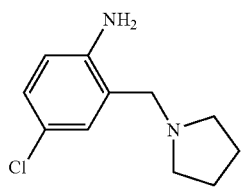

A mixture of the compound of preparation 167 (6.2 g, 25.8 mmol) and Raney® Nickel (400 mg) in ethanol (200 mL) was hydrogenated at 40 psi and room temperature for 2 hours. The mixture was filtered through Arbocel® and the filtrate was evaporated under reduced pressure. The residue was purified by column chromatography on silica gel using an elution gradient of dichloromethane:methanol:0.88 ammonia (95:5:0.5 to 90:10:1) to afford the title compound as a solid, 3.95 g.

¹H NMR (400 MHz, CDCl₃): δ 1.78 (m, 4H), 2.48 (m, 2H), 3.59 (s, 2H), 4.65-4.90 (br s, 2H), 6.56 (d, 1H), 6.98 (s, 1H), 7.00 (d, 1H). LCMS: m/z APCI⁺ 211 [MH]⁺

Preparation 169: 4-{[4-(4-Chlorophenyl)-5-piperidin-4-yl-4H-1,2,4-triazol-3-yl]methyl}morpholine

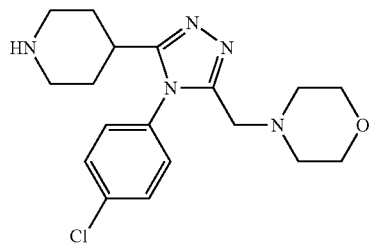

A solution of the compound of preparation 101 (8.6 g, 18.6 mmol) in dioxan (50 mL) and 4M hydrochloric acid in dioxan (30 mL) was stirred at room temperature for 18 hours. The solution was evaporated under reduced pressure and the residue was partitioned between 2N sodium hydroxide solution and ethyl acetate. The resulting solid was filtered off and dried to afford the title compound as a white solid, 1.2 g. The filtrate was separated, the aqueous layer was extracted with dichloromethane and the combined organic solutions were dried over MgSO₄ and evaporated under reduced pressure to afford additional product, 1.11 g.

LCMS: m/z APCI⁺ 362 [MH]⁺

Preparation 170: tert-Butyl 4-{[2-(2H-1,2,3-triazol-2-ylacetyl)hydrazino]carbonyl}piperidine-1-carboxylate

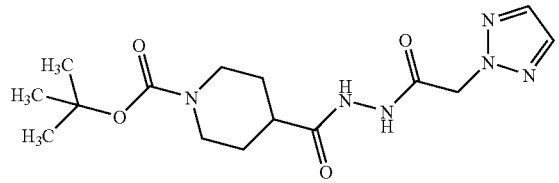

A suspension of N-Boc-isonipecotic acid (30.0 g, 130.8 mmol) and the hydrazide of preparation 18 (18.5 g, 130.8 mmol) in dichloromethane (150 mL) was cooled in an ice bath under N₂. 1-(3-Dimethylaminopropyl)-3-ethylcarbodiimide hydrochloride (25.6 g, 133.5 mmol) was added via an addition funnel, and the funnel was washed with additional dichloromethane (10 mL). The resulting solution was warmed to ambient temperature. Once the reaction was complete, iso-propanol (150 mL) was added and the homogeneous solution was concentrated in vacuo to approx 165 mL, heated to approx. 70° C., and allowed to cool to ambient temperature with stirring. The resulting thick white slurry was filtered in vacuo, washing with iso-propanol (15 mL and 30 mL) and dried in vacuo at 50° C. to give the title compound as a white solid, 25.3 g (55%). The liquors from the filtration were concentrated under reduced pressure to low volume, the resulting syrup was treated with water (50 mL) and vigorously stirred to give a thick slurry within two minutes. After overnight granulation, the slurry was filtered (rapid filtration), the residues washed with water (2×10 mL) and dried in vacuo at 50° C. to give additional product, 8.5 g (18%).

¹H NMR (CDCl₃) δ: 1.42 (s, 9H), 1.50-1.85 (m, 4H), 2.41 (m, 1H), 2.73 (t, 2H), 4.12 (d, 2H), 5.21 (s, 2H), 7.70 (s, 2H), 9.15 (d, 1H), 9.75 (d, 1H).

EXAMPLES 1 TO 162

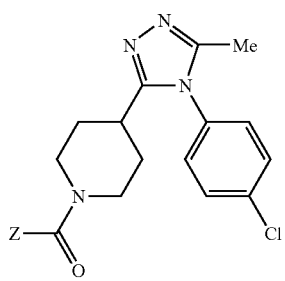

(I)

Examples 1 to 162 illustrated below were synthesised as a library. The following solutions were used:

carboxylic acid, ZCO₂H, was dissolved in dimethylacetamide (anhydrous) plus 3.75% triethylamine at 0.2M concentration.

the amine of preparation 2a was dissolved in DMA (anhydrous) plus 3.75% triethylamine at 0.2M concentration.

HBTU was dissolved in DMA (anhydrous) at 0.2M concentration.

(N.B. Gentle sonication, in a warm water bath (temp <40° C.), was used to dissolve the monomers where necessary.)

Experimental Procedure:

The reaction Scale was between 20 and 30 micromoles per well (experimental details shown for 20 μmole reaction, scale can be adjusted accordingly within this range). Reactions were performed in a polypropylene 96 well plate.
- a) Amine solutions (0.1 ml, 20 μmoles, 1 eq.) were added to the wells
- b) Carboxylic acid solutions (0.15 ml, 30 μmoles, 1.5 eq.) were added to the wells
- c) HBTU Solution (0.15 ml, 30 μmoles, 1.5 eq.) was added to each well
- d) The polypropylene 96 well plate was sealed with a PTFE and Rubber gasket and clamped between a pair of metal plates.
- e) The plate was heated in an oven for 6 h at 60° C. and then left to cool down in the oven overnight.
- f) When cool, the plate was unclamped and placed in a Genevac to remove the solvent.
- g) The samples were re-dissolved in DMSO/water (9:1) (500 μl) and any particulate matter was removed by filtration.
- h) Purification was carried-out by RP-HPLC.

HPLC Purification Conditions:
Column: Phenomenex Luna C18, 10 um, 150×10 mm id
Temperature: ambient
Eluent A: 0.05% Diethylamine in water
Eluent B: Acetonitrile
Samples dissolved in: 90% Dimethylsulphoxide in water.
Sample loaded using Gilson Autosampler with Injection Volume of 550 μl
Gilson LC Pump Initial Conditions:

| Solvents | |
|---|---|
| A % | 80.0 |
| B % | 20.0 |
| Flow (ml/min) | 8.000 |

Gilson LC Pump Gradient Timetable:

| Time | A % | B % | Flow (ml/min) |
|---|---|---|---|
| 0.00 | 80.0 | 20.0 | 8.000 |
| 0.20 | 80.0 | 20.0 | 8.000 |
| 7.00 | 5.0 | 95.0 | 8.000 |
| 9.00 | 5.0 | 95.0 | 8.000 |
| 9.10 | 80.0 | 20.0 | 8.000 |
| 10.50 | 80.0 | 20.0 | 8.000 |

Gilson 119 uv detector monitoring at 254 nm:
Collector set at 225 nm
Dual sensitivity 200
Peak sensitivity 80
Peak width 0.3 min.

HPLC Analysis Conditions and Mass Spectrometer Details:
Column: Phenomenex Luna C18, 5 um, 30×4.6 mm id.
Eluent A: 0.05% Diethylamine in water
Eluent B: Acetonitrile
Samples dissolved in: 90% Dimethylsulphoxide in water
Sample loaded using Gilson Quad Z with Injection Volume of 5 μl Waters 1525 Binary LC Pump Initial Conditions:

| Solvents | |
|---|---|
| A % | 95.0 |
| B % | 5.0 |
| Flow (ml/min) | 2.5 (per channel) |
| Temperature (° C.) | ambient |

LC Pump Gradient Timetable:
The gradient Timetable contains 4 entries, which are:

| Time | A % | B % | Flow |
|---|---|---|---|
| 0.00 | 95.0 | 5.0 | 2.500 |
| 3.00 | 5.0 | 95.0 | 2.500 |
| 3.50 | 95.0 | 5.0 | 2.500 |

Total run time 4.50 mins

Detection:

| Waters 2488 dual wavelength detector | |
|---|---|
| UV1 (nm) | 225 |
| UV2 (nm) | 255 |
| and | |
| ELSD: PolymerLabs, Temperature: 75° C., Gas flow: 1.2 bar | |

Mass Spectrometer:

| Waters ZQ 2000 4 way MUX, | | |
|---|---|---|
| ES+ Cone voltage: 26 v | Capillary: | 3.85 kv |
| ES– Cone voltage: –30 v | Capillary: | –3.00 kv |
| Desolvation gas: 800 l/min | | |
| Source Temp: 300° C. | | |
| Scan range 160-1000 Da | | |

| Ex. No. | Z | Mass ion of product found | HPLC Ret$^n$ time (Mins) |
|---|---|---|---|
| 1 | 2-methoxy-pyridin-3-yl | 412.15 | 1.55 |
| 2 | 3-trifluoromethyl-phenyl | 449.13 | 2 |
| 3 | 2-methoxy-phenyl | 411.15 | 1.35 |
| 4 | 2-methanesulfonyl-phenyl | 459.12 | 1.6 |
| 5 | 3-methanesulfonyl-phenyl | 459.12 | 1.55 |
| 6 | phenyl | 381.14 | 1.72 |
| 7 | 3-methoxy-phenyl | 411.15 | 1.67 |
| 8 | 4-fluoro-phenyl | 399.13 | 1.74 |
| 9 | 2-Chloro-phenyl | 415.1 | 1.8 |
| 10 | 4-Chloro-phenyl | 415.1 | 1.92 |
| 11 | 4-methanesulfonyl-phenyl | 459.12 | 1.49 |
| 12 | 2,4-dichloro-phenyl | 449.06 | 1.99 |
| 13 | 3,4-dichloro-phenyl | 449.06 | 2.04 |
| 14 | 2,5-dichloro-phenyl | 449.06 | 1.99 |
| 15 | 4-ethoxy-phenyl | 425.17 | 1.77 |
| 16 | 4-methylsulfanyl-phenyl | 427.13 | 1.85 |
| 17 | 4-Chloro-2-methoxy-phenyl | 445.11 | 1.89 |
| 18 | 2-ethoxy-phenyl | 425.17 | 1.84 |
| 19 | isoquinolin-1-yl | 432.15 | 1.6 |
| 20 | 2,6-dimethyl-phenyl | 409.17 | 1.82 |
| 21 | quinolin-2-yl | 432.15 | 1.74 |
| 22 | quinolin-4-yl | 432.15 | 1.6 |
| 23 | quinolin-3-yl | 432.15 | 1.57 |
| 24 | 2-Chloro-6-fluoro-phenyl | 433.09 | 1.54 |
| 25 | 2,3-dichloro-phenyl | 449.06 | 1.95 |
| 26 | 2,5-difluoro-phenyl | 417.12 | 1.82 |
| 27 | 2,5-dimethoxy-phenyl | 441.16 | 1.55 |
| 28 | 2,3-difluoro-phenyl | 417.12 | 1.8 |
| 29 | 2,4-difluoro-phenyl | 417.12 | 1.8 |
| 30 | 3,4-difluoro-phenyl | 417.12 | 1.85 |
| 31 | 4-isopropyl-phenyl | 423.19 | 2 |
| 32 | 6-methyl-pyridin-3-yl | 396.15 | 1.45 |
| 33 | 4-fluoro-naphthalen-1-yl | 449.15 | 2 |
| 34 | 3,5-difluoro-phenyl | 417.12 | 1.87 |
| 35 | 3-aminosulfonyl-4-chloro-phenyl | 494.07 | 1.5 |

-continued

| Ex. No. | Z | Mass ion of product found | HPLC Ret<sup>n</sup> time (Mins) |
|---|---|---|---|
| 36 | 1H-Benzoimidazol-5-yl | 421.15 | 1.37 |
| 37 | 2-Chloro-4-fluoro-phenyl | 433.09 | 1.85 |
| 38 | 4-trifluoromethoxy-phenyl | 465.12 | 2.07 |
| 39 | 1H-Benzotriazol-5-yl | 422.14 | 1.34 |
| 40 | 4-methoxy-quinolin-2-yl | 462.16 | 1.82 |
| 41 | 2-fluoro-4-trifluoromethyl-phenyl | 467.12 | 2.04 |
| 42 | 2,3,6-trifluoro-phenyl | 435.11 | 1.87 |
| 43 | 2-methyl-pyridin-3-yl | 396.15 | 1.32 |
| 44 | 2,4,5-trifluoro-phenyl | 435.11 | 1.85 |
| 45 | 4-propyl-phenyl | 423.19 | 2.15 |
| 46 | 2-fluoro-3-trifluoromethyl-phenyl | 467.12 | 1.92 |
| 47 | 3-fluoro-2-methyl-phenyl | 413.15 | 1.82 |
| 48 | 2,4-dichloro-5-fluoro-phenyl | 467.05 | 2.05 |
| 49 | 3-fluoro-4-methoxy-phenyl | 429.14 | 1.8 |
| 50 | 4-isopropoxy-phenyl | 439.18 | 1.89 |
| 51 | 4-propoxy-phenyl | 439.18 | 2.02 |
| 52 | 3-Chloro-4-fluoro-phenyl | 433.09 | 1.95 |
| 53 | 2,6-dimethoxy-pyridin-3-yl | 442.16 | 1.7 |
| 54 | 2-fluoro-5-methyl-phenyl | 413.15 | 1.85 |
| 55 | 3-fluoro-5-trifluoromethyl-phenyl | 467.12 | 2.09 |
| 56 | 4-difluoromethoxy-phenyl | 447.13 | 1.79 |
| 57 | Biphenyl-2-yl | 457.17 | 2.02 |
| 58 | 4-aminosulfonyl-phenyl | 460.11 | 1.45 |
| 59 | 3-Chloro-phenyl | 415.1 | 1.9 |
| 60 | 4-cyano-phenyl | 406.14 | 1.6 |
| 61 | 2,3-dimethoxy-phenyl | 441.16 | 1.68 |
| 62 | 2,6-dimethoxy-phenyl | 441.16 | 1.68 |
| 63 | 3,5-dimethoxy-phenyl | 441.16 | 1.82 |
| 64 | 3-fluoro-4-methyl-phenyl | 413.15 | 1.8 |
| 65 | 3-fluoro-phenyl | 399.13 | 1.75 |
| 66 | 3-methoxy-4-methyl-phenyl | 425.17 | 1.9 |
| 67 | naphthalen-1-yl | 431.16 | 1.95 |
| 68 | pyridin-3-yl | 382.14 | 1.3 |
| 69 | pyridin-2-yl | 382.14 | 1.42 |
| 70 | 6-methyl-pyridin-2-yl | 396.15 | 1.52 |
| 71 | m-tolyl | 395.16 | 1.85 |
| 72 | p-tolyl | 395.16 | 1.74 |
| 73 | 4-fluoro-3-methoxy-phenyl | 429.14 | 1.79 |
| 74 | 3-Chloro-4-methyl-phenyl | 429.12 | 2 |
| 75 | 5-Chloro-2-methyl-phenyl | 429.12 | 1.97 |
| 76 | 3-Chloro-2,6-dimethoxy-phenyl | 475.12 | 1.82 |
| 77 | 3-Chloro-2-fluoro-phenyl | 433.09 | 1.89 |
| 78 | 2-phenoxy-pyridin-3-yl | 474.16 | 1.82 |
| 79 | 2-trifluoromethoxy-phenyl | 465.12 | 1.99 |
| 80 | 3-ethoxy-phenyl | 425.17 | 1.79 |
| 81 | 3-Chloro-4-methoxy-phenyl | 445.11 | 1.85 |
| 82 | 3,5-dimethoxy-4-methyl-phenyl | 455.18 | 1.99 |
| 83 | 4-Chloro-3-methyl-phenyl | 429.12 | 2.05 |
| 84 | 2-Chloro-3,4-dimethoxy-phenyl | 475.12 | 1.72 |
| 85 | 3-cyclopentyloxy-4-methoxy-phenyl | 495.21 | 2 |
| 86 | 4-methoxy-3-propoxy-phenyl | 469.19 | 1.89 |
| 87 | 3-isopropoxy-4-methoxy-phenyl | 469.19 | 1.85 |
| 88 | 3-Butoxy-4-methoxy-phenyl | 483.21 | 1.95 |
| 89 | 4-trifluoromethoxy-pyridin-3-yl | 450.12 | 1.65 |
| 90 | 6-(2,2,2-trifluoro-ethoxy)-pyridin-3-yl | 480.13 | 1.95 |
| 91 | 2-(4-fluoro-phenoxy)-pyridin-3-yl | 492.15 | 1.9 |
| 92 | 2-chloro-3-trifluoromethyl-phenyl | 483.09 | 1.97 |
| 93 | 2-difluoromethoxy-phenyl | 447.13 | 1.82 |
| 94 | 3-difluoromethoxy-phenyl | 447.13 | 1.89 |
| 95 | 6-trifluoromethyl-pyridin-3-yl | 450.12 | 1.84 |
| 96 | 2-methyl-[1,8]naphthyridin-3-yl | 447.16 | 1.32 |
| 97 | 2-methyl-[1,6]naphthyridin-3-yl | 447.16 | 1.42 |
| 98 | 2,3-dihydro-benzofuran-7-yl | 423.15 | 1.57 |
| 99 | 2-Chloro-3-methyl-phenyl | 429.12 | 1.92 |
| 100 | 4-methoxy-3-methyl-phenyl | 425.17 | 1.92 |
| 101 | 2-ethoxy-pyridin-3-yl | 426.16 | 1.6 |
| 102 | 2-ethoxy-naphthalen-1-yl | 475.18 | 2.02 |
| 103 | 3-(dimethylamino)sulfonyl-phenyl | 488.14 | 1.72 |
| 104 | 2-propoxy-pyridin-3-yl | 440.18 | 1.84 |
| 105 | 2-(4-Chloro-phenoxy)-pyridin-3-yl | 508.12 | 1.93 |
| 106 | 2-methyl-1H-benzoimidazol-5-yl | 435.16 | 1.4 |
| 107 | 6-hydroxy-pyridin-2-yl | 398.13 | 1.32 |
| 108 | 2-(5-methyl-[1,2,4]oxadiazol-3-yl)-pyridin-4-yl | 464.15 | 1.45 |

-continued

| Ex. No. | Z | Mass ion of product found | HPLC Ret<sup>n</sup> time (Mins) |
|---|---|---|---|
| 109 | 4-(5-methyl-[1,2,4]oxadiazol-3-yl)-phenyl | 463.16 | 1.67 |
| 110 | 4-(5-ethyl-[1,2,4]oxadiazol-3-yl)-phenyl | 477.17 | 1.92 |
| 111 | 3-(5-methyl-[1,2,4]oxadiazol-3-yl)-phenyl | 463.16 | 1.68 |
| 112 | 3-(5-ethyl-[1,2,4]oxadiazol-3-yl)-phenyl | 477.17 | 1.9 |
| 113 | 2-hydroxy-pyridin-4-yl | 398.13 | 1.25 |
| 114 | 2-Benzyl-phenyl | 471.19 | 2.17 |
| 115 | 3,5-dichloro-phenyl | 449.06 | 2 |
| 116 | 3-Chloro-2-methyl-phenyl | 429.12 | 1.93 |
| 117 | 2,3-dihydro-benzofuran-5-yl | 423.15 | 1.74 |
| 118 | 2-(3-methyl-[1,2,4]oxadiazol-5-yl)-pyridin-4-yl | 464.15 | 1.49 |
| 119 | 3-hydroxy-2-methyl-phenyl | 411.15 | 1.54 |
| 120 | 2-fluoro-5-trifluoromethyl-phenyl | 467.12 | 2.02 |
| 121 | 4-methoxy-2-methyl-phenyl | 425.17 | 1.82 |
| 122 | 3-methoxy-2-methyl-phenyl | 425.17 | 1.82 |
| 123 | 2-hydroxy-5-methyl-phenyl | 411.15 | 1.68 |
| 124 | 3,5-dichloro-4-hydroxy-phenyl | 465.06 | 1.57 |
| 125 | 2-hydroxy-3-isopropyl-phenyl | 439.18 | 2.93 |
| 126 | 1H-indol-6-yl | 420.15 | 1.75 |
| 127 | 3-hydroxy-phenyl | 397.14 | 1.6 |
| 128 | 3-methoxy-naphthalen-2-yl | 461.17 | 1.9 |
| 129 | 3-hydroxy-4-methoxy-phenyl | 427.15 | 1.54 |
| 130 | 4-Chloro-2-hydroxy-phenyl | 431.1 | 1.77 |
| 131 | 3,4-dimethoxy-2-methyl-phenyl | 455.18 | 1.79 |
| 132 | 6-(acetylamino)-pyridin-3-yl | 439.16 | 1.35 |
| 133 | 2,6-dimethoxy-4-methyl-phenyl | 455.18 | 1.8 |
| 134 | 2-Benzyloxy-phenyl | 487.18 | 2.07 |
| 135 | 6-methoxy-quinolin-2-yl | 462.16 | 1.82 |
| 136 | quinoxalin-6-yl | 433.15 | 1.42 |
| 137 | 1,2-dimethyl-1H-benzoimidazol-5-yl | 449.18 | 1.49 |
| 138 | 1H-indol-5-yl | 420.15 | 1.7 |
| 139 | 2-(3,5-dimethyl-1H-pyrazol-4-yl)-5-methoxy-phenyl | 505.2 | 1.6 |
| 140 | 8-methyl-2-oxo-1,2-dihydroquinolin-6-yl | 462.16 | 1.45 |
| 141 | 3-aminosulfonyl-phenyl | 460.11 | 1.5 |
| 142 | 4-(3-methyl-6-oxo-3-piperidinyl)-phenyl | 492.21 | 1.54 |
| 143 | 3-(2-methoxy-ethoxy)-phenyl | 455.18 | 1.62 |
| 144 | 2-hydroxy-4-methyl-phenyl | 411.15 | 1.68 |
| 145 | 3-Chloro-4-hydroxy-phenyl | 431.1 | 1.64 |
| 146 | 3-hydroxy-4-methyl-phenyl | 411.15 | 1.75 |
| 147 | 3-methoxy-5-(methylsulfonyl)amino-phenyl | 504.14 | 1.57 |
| 148 | 2-{[(2,2-dimethyl-propyl)amino]carbonyl}-phenyl | 494.22 | 1.85 |
| 149 | 5-acetyl-2-ethoxypyridin-3-yl | 468.17 | 1.7 |
| 150 | 2-(2-methoxy-ethoxy)-pyridin-3-yl | 456.17 | 1.62 |
| 151 | isoquinolin-4-yl | 432.15 | 1.52 |
| 152 | 2-ethoxy-3-methoxy-phenyl | 455.18 | 1.8 |
| 153 | 4-[(1R)-1-(acetylamino)ethyl]-phenyl | 466.19 | 1.47 |
| 154 | 4-pyrimidin-4-yl-phenyl | 459.16 | 1.6 |
| 155 | 3-methyl-2-propoxy-phenyl | 453.2 | 2 |
| 156 | 4-ethoxy-pyridin-3-yl | 426.16 | 1.5 |
| 157 | 2-chloro-4-methylsulfonylamino-phenyl | 508.09 | 1.64 |
| 158 | 2-ethoxy-5-methanesulfonyl-phenyl | 503.14 | 1.68 |
| 159 | 4-hydroxy-2-(2,2,2-trifluoro-ethoxy)-phenyl | 495.13 | 1.65 |
| 160 | 4-hydroxy-2-methoxy-phenyl | 427.15 | 1.52 |
| 161 | 4-cyano-pyridin-2-yl | 407.13 | 1.55 |
| 162 | 2-pyridin-4-yl-3H-benzoimidazol-5-yl | 498.17 | 1.5 |

EXAMPLE 163

(3-Chloro-phenyl)-{4-[4-(4-chloro-phenyl)-5-[1,2,3]triazol-2-ylmethyl-4H-[1,2,4]triazol-3-yl]-piperidin-1-yl}-methanone

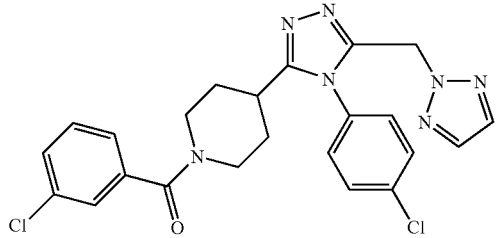

A mixture of the compound from preparation 10 (202 mg, 0.54 mmol), 4-chloroaniline (140 mg, 1.1 mmol) and trifluoroacetic acid (42 μl, 0.54 mmol) in toluene (2 ml) was heated at 170° C. for 20 minutes under microwave radiation. The cooled mixture was diluted with ethyl acetate, washed with 1N sodium hydroxide solution and brine, then dried over $Na_2SO_4$ and concentrated under reduced pressure. The product was purified by column chromatography on silica gel using dichloromethane:methanol:0.88 ammonia (100:0:0 to 90:10:1) to afford the title compound, (234 mg).

$^1$H NMR (400 MHz, $CD_3OD$): δ 1.80-1.97 (m, 4H), 2.86 (m, 2H), 3.08 (m, 1H), 3.70 (m, 1H), 4.58 (m, 1H), 5.72 (s, 2H), 7.26 (m, 2H), 7.32 (m, 1H), 7.41-7.54 (m, 5H), 7.59 (s, 2H).

LRMS: m/z ($APCI^+$) 482 $[MH]^+$

EXAMPLE 164

(4-Chloro-phenyl)-{4-[4-(4-chloro-phenyl)-5-[1,2,3]triazol-2-ylmethyl-4H-[1,2,4]triazol-3-yl]-piperidin-1-yl}-methanone

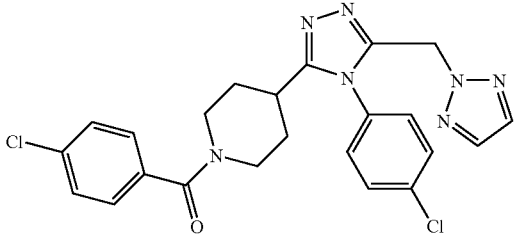

4-Chlorobenzoyl chloride (49 μl, 0.38 mmol) was added to a mixture of the compound from preparation 12a (120 mg, 0.35 mmol) and N-methyl morpholine (77 μl, 0.70 mmol) in dichloromethane (2 ml), then the mixture was stirred at room temperature for 2 hours. The reaction was diluted with dichloromethane, washed with 1N sodium hydroxide solution and the aqueous wash re-extracted with dichloromethane. The combined organic solutions were evaporated under reduced pressure to give an oil. This was purified by column chromatography on silica gel using dichloromethane:methanol:0.88 ammonia (90:10:1) to afford the title compound as a white solid, (160 mg).

$^1$H NMR (400 MHz, DMSO-$d_6$): δ 1.60-1.82 (m, 4H), 2.70-3.04 (m, 3H), 3.54 (m, 1H), 4.33 (m, 1H), 5.66 (s, 2H), 7.34 (d, 2H), 7.39 (d, 2H), 7.48 (d, 2H), 7.57 (d, 2H), 7.64 (s, 2H);

LRMS: m/z ($APCI^+$) 482 $[MH]^+$

EXAMPLE 165a

{4-[4-(4-Chloro-phenyl)-5-[1,2,3]triazol-2-ylmethyl-4H-[1,2,4]triazol-3-yl]-piperidin-1-yl}-(3,5-difluoro-phenyl)-methanone

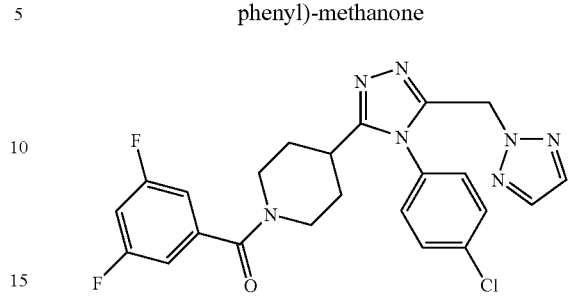

The title compound was obtained in 92% yield from the compound from preparation 12a and 2,4-difluorobenzoyl chloride, following the procedure described in example 164.

$^1$H NMR (400 MHz, $CD_3OD$): δ 1.80-1.98 (m, 4H), 2.84 (m, 2H), 3.09 (m, 1H), 3.65 (m, 1H), 4.58 (m, 1H), 5.72 (s, 2H), 7.05 (m, 3H), 7.24 (m, 2H), 7.57 (d, 2H), 7.59 (s; 2H).

LRMS: m/z ($APCI^+$) 484 $[MH]^+$

EXAMPLE 165b

{4-[4-(4-Chloro-phenyl)-5-[1,2,3]triazol-2-ylmethyl-4H-[1,2,4]triazol-3-yl]-piperidin-1-yl}-(3,5-difluoro-phenyl)-methanone Triethylamine (3.2 ml, 23.0 mmol) was added to a slurry of the bis salt from preparation 12b (4.89 g, 7.12 mmol) in dichloromethane (25 ml) giving a pale yellow solution. The solution was cooled in an ice-bath and then 3,5-difluorobenzoyl chloride (0.95 ml, 8.09 mmol) was added. The reaction was stirred for 30 minutes, and then water (20 ml) was added. After a further 20 minutes of stirring, the phases were separated and the organic phase was washed successively with aqueous citric acid, water, aqueous sodium hydrogen carbonate and half-saturated brine. The clear dichloromethane solution was then dried over magnesium sulphate and concentrated to give a white foam. Recrystallisation from ethyl acetate gave the title compound as a white solid, (2.69 g), identical to material prepared as described in Example 165a.

EXAMPLES 166 TO 167

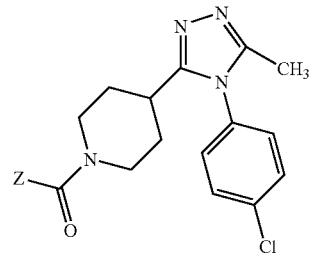

The appropriate acid chloride (1.2 eq.) was added to a solution of the amine of preparation 2 (1 eq.) and N-methylmorpholine (1.5 eq.) in dichloromethane (5.5 $mLmmol^{-1}$) and the reaction was stirred at room temperature for 4 hours. Tris-(2-aminoethyl)amine polystyrene (3.85 mmol/g) was added and the reaction was stirred for a further hour. Saturated ammonium chloride solution was added, the mixture was then stirred for 20 minutes and the layers were separated using a hydrophobic membrane. The organic phase was washed with saturated sodium bicarbonate solution, the layers were separated and the organic solution was evaporated under reduced pressure to provide the title compounds.

| Ex No | Z | Yield (%) | Data |
|---|---|---|---|
| 166 | Neopentyl | 39 | $^1$H NMR(400MHz, CDCl$_3$): δ 1.00(s, 9H), 1.71(m, 2H), 1.82(m, 1H), 1.98(m, 1H), 2.20(s, 2H), 2.24(s, 3H), 2.57(m, 1H), 2.65(m, 1H), 3.00(m, 1H), 3.98(m, 1H), 4.57(m, 1H), 7.20(d, 2H), 7.57(d, 2H). LCMS: m/z APCl$^+$ 375[MH]$^+$ |
| 167 | Cyclopropyl | 39 | $^1$H NMR(400MHz, CDCl$_3$): δ 0.73(m, 2H), 0.94(m, 2H), 1.70(m, 3H), 1.88(m, 1H), 2.02(m, 1H), 2.22(s, 3H), 2.58-2.75(m, 2H), 3.08(m, 1H), 4.23(m, 1H), 4.44(m, 1H), 7.20(d, 2H), 7.58(d, 2H). LCMS: m/z APCl$^+$ 347[MH]$^+$ |

EXAMPLES 168 TO 173

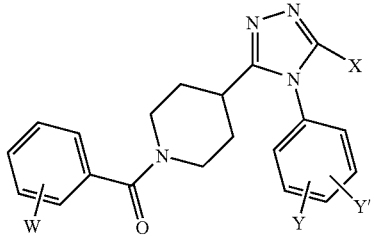

A mixture of the appropriate amine, or amine salt, selected from preparations 12a, 100, 118, 119, 143, and 152 (1 eq.), the appropriate acid chloride (W-PhCOCl) (1.2 to 1.4 eq.) and N-ethyldiisopropylamine (4 eq.) in dichloromethane (16 mLmmol$^{-1}$) was stirred at room temperature for 2 hours. Tris-(2-aminoethyl)amine polystyrene was then added and the mixture was stirred for another hour. The mixture was then washed with 1N sodium hydroxide solution, the aqueous solution was extracted with dichloromethane (2×) and the combined organic solutions were concentrated under reduced pressure. The crude products were purified by column chromatography on silica gel using ethyl acetate:methanol:0.88 ammonia (90:10:1) as eluant, to afford the title compounds.

| Ex No | Data |
|---|---|
| 168 | W=3-F, 4-CH$_3$; Y=4-Cl; Y'=2-Cl; X=CH$_3$ $^1$H NMR(400MHz, CDCl$_3$): δ 1.77-1.99(m, 4H), 2.19(s, 3H), 2.26(s, 3H), 2.59(m, 1H), 2.84-3.02(m, 2H), 3.83(m, 1H), 4.55(m, 1H), 7.02(m, 2H), 7.18-7.28(m, 2H), 7.48(m, 1H), 7.66(s, 1H). LCMS: m/z APCl$^+$ 447[MNa]$^+$ |
| 169$^A$ | W=3-F, 4-CH$_3$; Y=4-Cl; Y'=2-F; X=CH$_3$ $^1$H NMR(400MHz, CDCl$_3$): δ 1.75-2.00(m, 4H), 2.24(m, 6H), 2.63(m, 1H), 2.92(m, 2H), 3.81(m, 1H), 4.56(m, 1H), 7.02(m, 2H), 7.19(m, 1H), 7.40(m, 3H). LCMS: m/z APCl$^+$ 431[MH]$^+$ |
| 170 | W=3,5-di-Cl; Y=4-Cl; Y'=2-OCH$_3$; X=CH$_3$ $^1$H NMR(400MHz, CD$_3$OD): δ 1.70-2.00(m, 4H), 2.17(s, 3H), 2.72-2.92(m, 2H), 3.1(m, 1H), 3.62(m, 1H), 3.84(m, 1H), 4.56(m, 1H), 7.20(m, 1H), 7.39(m, 4H), 7.58(s, 1H). LCMS: m/z APCl$^+$ 480[MH]$^+$ |
| 171$^A$ | W=2-F, 3-Cl; Y=4-Cl; Y'=H; X=CH$_2$OCH$_2$CH$_3$; $^1$H NMR(400MHz, CDCl$_3$): δ 1.08(t, 3H), 1.64-1.81(m, 2H), 1.84-2.01(m, 2H), 2.79(m, 1H), 2.85-3.17(m, 2H), 3.41(q, 2H), 3.62(m, 1H), 4.41(s, 2H), 4.62(m, 1H), 7.17(m, 1H), 7.23(m, 3H), 7.43(m, 1H), 7.58(d, 2H). LCMS: m/z APCl$^+$ 477[M]$^+$ |
| 172$^A$ | W=4-Cl; Y=4-Cl; Y'=H; X=CH$_2$CF$_3$; $^1$H NMR(400MHz, CDCl$_3$): δ 1.81(m, 2H), 1.98(m, 2H), 2.70(m, 1H), 2.80-3.02(m, 2H), 3.44(q, 2H), 3.81(m, 1H), 4.59(m, 1H), 7.19(d, 2H), 7.38(m, 4H), 7.60(d, 2H). LCMS: m/z APCl$^+$ 483[M]$^+$ |
| 173$^B$ | W=2-OCF$_3$; Y=4-Cl; Y'=H; X=[1,2,3]-triazol-2-ylmethyl $^1$H NMR(400MHz, CDCl$_3$): δ 1.76(m, 1H), 1.79-2.02(m, 3H), 2.68(m, 1H), 2.82-3.02(m, 2H), 3.58(m, 1H), 4.59(m, 1H), 5.62(s, 2H), 6.99(m, 2H), 7.22-7.42(m, 6H), 7.50(s, 2H). LCMS: m/z APCl$^+$ 532[MH]$^+$ |

$^A$= 4 eq. of triethylamine were used, and the crude product was not treated with polymer supported amine.
$^B$= 10 eq. of polymer supported N-ethyldiisopropylamine was used in place of N-ethyldiisopropylamine.

EXAMPLES 174 TO 187

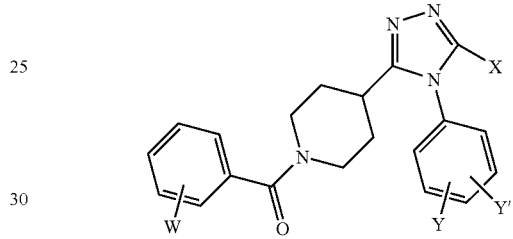

The appropriate acid chloride (W-PhCOCl) (1.0 to 1.5 eq.) was added to a solution of the appropriate amine hydrochloride, or amine, selected from preparations 120 to 121, 132, 134 to 135, 137, 139 to 142, 151, 153 to 154, and 169 (1 eq.), and triethylamine (1.2 to 5 eq.) in dichloromethane (10 to 25 mLmmol$^{-1}$). The reaction was stirred at room temperature for 18 hours. The mixture was then diluted with dichloromethane, it was washed with saturated sodium carbonate solution, followed by ammonium chloride solution, and then it was concentrated under reduced pressure. The crude products were purified by column chromatography on silica gel using dichloromethane:methanol (100:0 to 90:10) as eluant to afford the title compounds.

| Ex No | Data |
|---|---|
| 174$^A$ | W=3-Cl; Y=4-Cl; Y'=2-CH$_3$; X=CH$_3$ $^1$H NMR(400MHz, CDCl$_3$): δ 1.65-2.02(m, 7H), 2.18(s, 3H), 2.55(m, 1H), 2.78-3.01(m, 2H), 3.79 (m, 1H), 4.58(m, 1H), 7.03(m, 1H), 7.20-7.39 (m, 5H), 7.41(s, 1H). LCMS: m/z APCl$^+$ 451[MNa]$^+$ |
| 175$^B$ | W=3,5-di-Cl; Y=4-Cl; Y'=H; X=CH$_2$OCH$_3$ $^1$H NMR(400MHz, CD$_3$OD): δ 1.81-1.98(m, 4H), 2.86(m, 2H), 3.12(m, 1H), 3.20(s, 3H), 3.64(m, 1H), 4.38(s, 2H), 4.58(m, 1H), 7.40(s, 2H), 7.46(d, 2H), 7.58(s, 1H), 7.62(d, 2H). LCMS: m/z APCl$^+$ 479, 481[MH]$^+$ |
| 176$^A$ | W=4-Cl; Y=4-Cl; Y'=H; X=CH$_2$OCF$_3$ $^1$H NMR(400MHz, CDCl$_3$): δ 1.81(m, 2H), 1.98(m, 2H), 2.78(m, 1H), 2.96(m, 2H), 3.75-3.90(m, 1H), 4.40-4.60(m, 1H), 4.97(s, 2H), 7.21(m, 2H), 7.37(m, 4H), 7.59(d, 2H). LCMS: m/z APCl$^+$ 499[M]$^+$ |
| 177$^B$ | W=3,5-di-F; Y=4-Cl; Y'=H; X=CH$_2$OCH$_2$CF$_3$ $^1$H NMR(400MHz, CDCl$_3$): δ 1.80-2.02(m, 4H), 2.79(m, 1H), 2.83-3.05(m, 2H), 3.80(m, 3H), 4.58(m, 3H), 6.85(m, 3H), 7.22(d, 2H), 7.57(d, 2H). LCMS: m/z APCl$^+$ 515[MH]$^+$ |

-continued

| Ex No | Data |
|---|---|
| 178 | W=3-Cl; Y=4-Cl; Y'=H; X=(2-oxopyrrolidin-1-yl)methyl; ¹H NMR(400MHz, CDCl₃): δ 1.78-2.00(m, 6H), 2.22(t, 2H), 2.75(m, 1H), 2.97(m, 2H), 3.48(t, 2H), 3.80(m, 1H), 4.42(s, 2H), 4.58(m, 1H), 7.00(d, 2H), 7.23(d, 1H), 7.38(m, 3H), 7.58(d, 2H). LCMS: m/z APCl⁺ 499, 501[MH]⁺ |
| 179[A] | W=3,5-di-Cl; Y=4-Cl; Y'=H; X=morpholin-4-ylmethyl; ¹H NMR(400MHz, CDCl₃): δ 1.78-2.02(m, 4H), 2.40(m, 4H), 2.78(m, 1H), 2.78-3.04(m, 2H), 3.41(s, 2H), 3.58(m, 4H), 3.78(m, 1H), 4.58(m, 1H), 7.23(m, 5H), 7.56(d, 2H). LCMS: m/z APCl⁺ 534[M]⁺ |
| 180 | W=3-F; Y=4-Cl; Y'=H; X=1H-tetrazol-1-ylmethyl; ¹H NMR(400MHz, CDCl₃): δ 1.60-1.83(m, 4H), 2.60-2.78(m, 2H), 3.00(m, 1H), 3.90(m, 1H), 4.50(m, 1H), 5.58(s, 2H), 6.98(m, 2H), 7.50(m, 2H), 7.29(m, 1H), 7.60(d, 2H), 8.79(s, 1H). LCMS: m/z ES⁺ 481, 483[MH]⁺ |
| 181 | W=3-Cl; Y=4-Cl; Y'=H; X=2-methyl-imidazo-3-ylmethyl; ¹H NMR(400MHz, CDCl₃): δ 1.77-1.83(m, 2H), 1.89-2.00(m, 2H), 2.14(s, 3H), 2.64(m, 2H), 2.94(m, 1H), 3.82(m, 1H), 4.58(m, 1H), 5.08(s, 2H), 6.60(s, 1H), 6.96(m, 3H), 7.24(m, 1H), 7.32-7.40(m, 3H), 7.58(d, 2H). LCMS: m/z APCl⁺ 495, 497[MH]⁺ |
| 182 | W=3-Cl; Y=4-Cl; Y'=H; X=3-methyl-[1,2,4]oxadiazol-5-ylmethyl ¹H NMR(400MHz, CDCl₃): δ 1.80(m, 2H), 1.98(m, 2H), 2.30(s, 3H), 2.76(m, 1H), 2.95(m, 2H), 3.80(m, 1H), 4.22(s, 2H), 4.58(m, 1H), 7.19(d, 2H), 7.24(d, 1H), 7.37(m, 3H), 7.52(d, 2H). LCMS: m/z APCl⁺ 497, 499[MH]⁺ |
| 183 | W=3,5-di-F; Y=4-Cl; Y'=H; X=[1,2,4]-triazol-1-ylmethyl ¹H NMR(400MHz, CDCl₃): δ 1.82(m, 2H), 2.00(m, 2H), 2.75(m, 1H), 2.80-3.08(m, 2H), 3.80(m, 1H), 4.58(m, 1H), 5.40(s, 2H), 6.89(m, 3H), 7.15(m, 2H), 7.58(d, 2H), 7.82(s, 1H), 8.04(s, 1H). LCMS: m/z APCl⁺ 484, 486[MH]⁺ |
| 184[B] | W=2-F, 3-Cl; Y=4-Cl; Y'=H; X=pyrimidin-2-yloxymethyl ¹H NMR(400MHz, CDCl₃): δ 1.75(m, 2H), 1.97(m, 2H), 2.81(m, 1H), 2.88-3.15(m, 2H), 3.62(m, 1H), 4.62(m, 1H), 5.43(s, 2H), 6.98(m, 1H), 7.16(m, 1H), 7.25(m, 1H), 7.36(d, 2H), 7.44(m, 2H), 8.44(d, 2H). LCMS: m/z APCl⁺ 527[M]⁺ |
| 185 | W=2-F, 3-Cl; Y=4-Cl; Y'=H; X=2-pyridin-2-yl-ethyl ¹H NMR(400MHz, CDCl₃): δ 1.58-1.98(m, 4H), 2.75(m, 1H), 2.90-3.00(m, 2H), 3.04-3.18(m, 2H), 3.42(m, 2H), 3.61(m, 1H), 4.60(m, 1H), 7.10-7.27(m, 6H), 7.42(m, 1H), 7.56(d, 2H), 7.82(m, 1H), 8.48(s, 1H). LCMS: m/z APCl⁺ 524[MH]⁺ |
| 186 | W=3-Cl; Y=4-Cl; Y'=H; X=2-morpholin-4-ylethyl ¹H NMR(400MHz, CDCl₃): δ 1.80(m, 2H), 1.97(m, 2H), 2.40(m, 4H), 2.64-3.02(m, 7H), 3.59-3.90(m, 5H), 4.58(m, 1H), 7.19(d, 2H), 7.24(m, 2H), 7.36(m, 2H), 7.58(d, 2H). LCMS: m/z APCl⁺ 514[M]⁺ |
| 187 | W=5-Cl, 2-F; Y=4-Cl; Y'=H; X=2-(3,5-dimethyl-isoxazol-4-yl)-ethyl; ¹H NMR(400MHz, CDCl₃): δ 1.75-1.98(m, 7H), 2.04(s, 3H), 2.63-2.80(m, 5H), 2.86-3.08(m, 2H), 3.62(m, 1H), 4.59(m, 1H), 6.75(m, 2H), 7.01(m, 1H), 7.37(m, 2H), 7.57(d, 2H). LCMS: m/z APCl⁺ 542, 544[MH]⁺ |

[A] = ethyl acetate:methanol:0.88 ammonia was used as the column eluant.
[B] = 2 eq N-methylmorpholine was used instead of triethylamine.
[C] = 3 equivalents of N-methylmorpholine were used in place of triethylamine.

EXAMPLE 188

4-[4-(4-Chlorophenyl)-5-(1H-imidazol-1-ylmethyl)-4H-1,2,4-triazol-3-yl]-1-(3,3-dimethylbutanoyl)piperidine

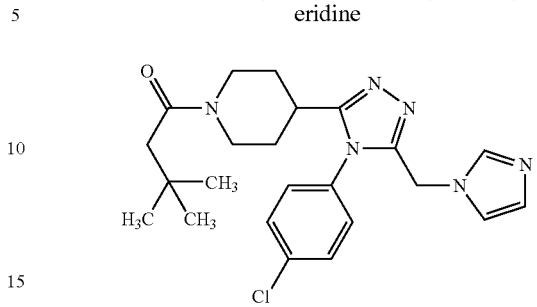

The title compound was obtained as a white solid, from the compound of preparation 138 and isovaleryl chloride, following the procedure described for examples 174 to 187.

¹H NMR (400 MHz, CDCl₃): δ 1.01 (s, 9H), 1.70-1.85 (m, 2H), 1.98 (m, 3H), 2.22 (m, 2H), 2.55-2.66 (m, 2H), 3.00 (m, 1H), 4.00 (m, 1H), 4.59 (m, 1H), 5.18 (s, 2H), 6.60 (s, 1H), 6.90 (m, 2H), 7.00 (s, 1H), 7.20 (s, 1H), 7.52 (m, 2H); LCMS: m/z APCl⁺ 441 [MH]⁺

EXAMPLES 189 TO 198

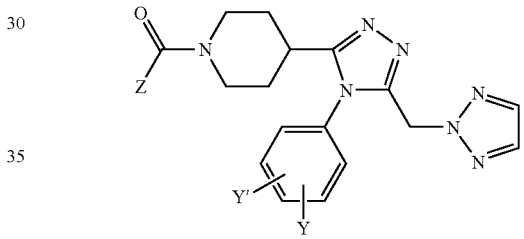

The appropriate acid chloride, ZCOCl, (1.0 eq.) was added to a solution of the appropriate amine selected from those of preparations 122 to 131 (1 eq.), and triethylamine (1.1 eq.) in dichloromethane (4 mLmmol⁻¹). The reaction was stirred at room temperature for 1 hour. It was then diluted with water, stirred for 5 minutes, and then filtered through a phase separation cartridge. The organic solution was concentrated under reduced pressure and the crude product was purified by column chromatography on silica gel using ethyl acetate:dichloromethane:methanol (100:0:0 to 0:95:5) as eluant. The products were azeotroped with ether to afford the title compounds as white foams.

| Ex No | Data |
|---|---|
| 189 | Z=3-Chloro-2-fluorophenyl; Y=H; Y'=H; ¹H NMR(400MHz, CDCl₃): δ 1.68-2.07(m, 4H), 2.75(m, 1H), 2.92(m, 1H), 3.01(m, 1H), 3.61(m, 1H), 4.60(m, 1H), 5.64(s, 2H), 7.06(d, 2H), 7.13(t, 1H), 7.38-7.57(m, 7H). LCMS: m/z ES⁺ 488[MNa]⁺ |
| 190 | Z=3-Chlorophenyl Y=4-OCH₃; Y'=H; ¹H NMR(400MHz, CDCl₃): δ 1.75-2.20(m, 4H), 2.79(m, 1H), 2.93(m, 2H), 3.80(m, 1H), 3.84(s, 3H), 4.56(m, 1H), 5.66(s, 2H), 6.94(m, 2H), 7.01(m, 2H), 7.26(m, 1H), 7.28-7.40(m, 3H), 7.51(s, 2H). LCMS: m/z ES⁺ 500[MNa]⁺ |
| 191 | Z=3-Chloro-2-fluorophenyl; Y=4-F; Y'=H; ¹H NMR(400MHz, CDCl₃): δ 1.72-2.07(m, 4H), 2.77(m, 1H), 2.90(m, 1H), 3.02(m, 1H), 3.62(m, 1H), |

| Ex No | Data |
|---|---|
| | 4.61(m, 1H), 5.64(s, 2H), 7.05-7.19(m, 6H), 7.41(t, 1H), 7.49(s, 2H). LCMS: m/z ES+ 503[MNa]+ |
| 192 | Z=3-Chloro-2-fluorophenyl; Y=4-Br; Y'=H; $^1$H NMR(400MHz, CDCl$_3$): δ 1.71-2.06(m, 4H), 2.72(m, 1H), 2.94(m, 1H), 3.05(m, 1H), 3.63(m, 1H), 4.62(m, 1H), 5.65(s, 2H), 6.95(d, 2H), 7.14(t, 1H), 7.27(m, 1H), 7.43(t, 1H), 7.49(s, 2H), 7.60(d, 2H). LCMS: m/z ES+ 546[MH]+ |
| 193 | Z=3-Chloro-2-fluoro-phenyl; Y=4-CF$_3$; Y'=H; $^1$H NMR(400MHz, CDCl$_3$): δ 1.75-2.15(m, 4H), 2.76-2.94(m, 2H), 3.05(m, 1H), 3.62(m, 1H), 4.67(m, 1H), 5.76(s, 2H), 7.14(dd, 1H), 7.20-7.30(m, 2H), 7.36-7.50(m, 4H), 7.75(d, 2H). LCMS: m/z ES+ 556[MNa]+ |
| 194 | Z=3-Chlorophenyl; Y=4-CH$_3$; Y'=H; $^1$H NMR(400MHz, CDCl$_3$): δ 1.88(m, 2H), 2.06(m, 2H), 2.42(s, 3H), 2.79-3.00(m, 3H), 3.80(m, 1H), 4.59(m, 1H), 5.70(s, 2H), 7.07(d, 2H), 7.23-7.40(m, 6H), 7.53(s, 2H). LCMS: m/z ES+ 484[MNa]+ |
| 195 | Z=3-Chloro-2-fluoro-phenyl; Y=4-CN; Y'=H; $^1$H NMR(400MHz, CDCl$_3$): δ 1.67-2.00(m, 4H), 2.67(m, 1H), 2.80-3.08(m, 2H), 3.60(m, 1H), 4.58(m, 1H), 5.64(s, 2H), 7.11(t, 1H), 7.16-7.25(m, 3H), 7.41(t, 1H), 7.46(s, 2H), 7.75(d, 2H). LCMS: m/z ES+ 513[MNa]+ |
| 196 | Z=3-Chloro-2-fluorophenyl; Y=4-Cl; Y'=2-CH$_3$; $^1$H NMR(400MHz, CDCl$_3$): δ 1.68-1.98(m, 6H), 2.07(m, 1H), 2.60(m, 1H), 1.80-3.13(m, 2H), 3.60(d, 1H), 4.60(d, 1H), 5.55(d, 1H), 5.67(d, 1H), 6.86-7.50(m, 8H). LCMS: m/z ES+ 536[MNa]+ |
| 197 | Z=3-chlorophenyl; Y=4-Cl; Y'=3-F; $^1$H NMR(400MHz, CDCl$_3$): δ 1.84(m, 2H), 2.00(m, 2H), 2.72(m, 1H), 2.94(m, 2H), 3.83(m, 1H), 4.55(m, 1H), 5.67(s, 2H), 6.90(d, 2H), 7.26-7.41(m, 4H), 7.50-7.56(m, 3H). LCMS: m/z ES+ 500[MH]+ |
| 198 | Z=3-Chloro-2-fluoro-phenyl; Y=4-Cl; Y'=3-Cl; $^1$H NMR(400MHz, CDCl$_3$): δ 1.80(m, 1H), 1.86-2.05(m, 3H), 2.74(m, 1H), 2.92(m, 1H), 3.04(m, 1H), 3.61(m, 1H), 4.61(m, 1H), 5.70(s, 2H), 7.05-7.16(m, 3H), 7.27(br s, 1H), 7.40(t, 1H), 7.50(s, 2H), 7.55(d, 1H) LCMS: m/z ES+ 534[MNa]+ |

EXAMPLES 199 TO 201

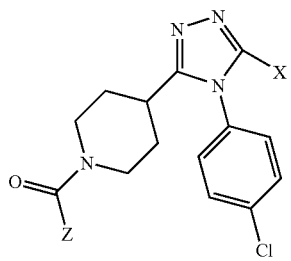

A mixture of the appropriate acid, ZCO$_2$H, (1.2 eq.), 1-hydroxybenzotriazole hydrate (1.2 eq.), triethylamine (2 to 4 eq.) and 1-(3-dimethylaminopropyl)-3-ethylcarbodiimide hydrochloride (1.2 eq.) and the appropriate amine, or amine hydrochloride, selected from preparations 2 and 143 (1 eq.) in dichloromethane (26 mlmmol$^{-1}$) was stirred at room temperature for 24 hours. The reaction was then washed with 2N sodium hydroxide solution and the organic solution was evaporated under reduced pressure. The crude product was purified by column chromatography on silica gel using an elution gradient of ethyl acetate:methanol:0.88 ammonia (100:0:0 to 95:5:0.5) to afford the title compounds.

| Ex No | Data |
|---|---|
| 199 | Z=Cyclopropylmethyl; X=CH$_2$OCH$_2$CH$_3$ $^1$H NMR(400MHz, CDCl$_3$): δ 0.18(m, 2H), 0.58(m, 2H), 1.06(t, 3H), 1.70-1.90(m, 3H), 2.00(m, 2H), 2.22(m, 2H), 2.59-2.77(m, 2H), 3.02(m, 1H), 3.40(q, 2H), 3.92(m, 1H), 4.40(s, 2H), 4.55(m, 1H), 7.22(d, 2H), 7.54(d, 2H). LCMS: m/z APCl+ 403[MH]+ |
| 200$^A$ | Z=5-Trifluoromethylpyridin-2-yl; X=CH$_2$OCH$_2$CH$_3$ $^1$H NMR(400MHz, CDCl$_3$): δ 1.08(t, 3H), 1.79-2.04(m, 4H), 2.60(m, 1H), 2.95-3.17(m, 2H), 3.20(q, 2H), 3.78(m, 1H), 4.41(s, 2H), 4.59(m, 1H), 7.22(d, 2H), 7.57(d, 2H), 7.77(d, 1H), 7.95(d, 1H), 8.55(s, 1H). LCMS: m/z APCl+ 494[MH]+ |
| 201$^B$ | Z=1H-Indazol-3-yl; Y=4-Cl; Y'=H; X=CH$_3$ $^1$H NMR(400MHz, CDCl$_3$): δ 1.65-1.88(m, 4H), 2.15(s, 3H), 2.80-2.97(m, 2H), 3.08(m, 1H), 4.42-4.62(m, 2H), 7.20(dd, 1H), 7.40(dd, 1H), 7.57(m, 3H), 7.65(d, 2H), 7.90(d, 1H), 13.42(s, 1H). LCMS: m/z APCl+ 421[MH]+ |

$^A=$ 5-(trifluoromethyl)-2-pyridinecarboxylic acid was used and may be prepared as described in J. Org. Chem. (European) 2003; (8); 1559-1568.
$^B=$ reaction was performed in the absence of 1-hydroxybenzotriazole hydrate and triethylamine.

EXAMPLES 202 TO 204

A solution of the appropriate acid, ZCO$_2$H, (1.5 eq.), O-benzotriazol-1-yl-N,N,N',N'-tetramethyluronium hexafluorophosphate (2 eq.), N-methylmorpholine (5 eq.) and the appropriate amine hydrochloride selected from preparations 2 and 133 (1 eq.) in dichloromethane (8 mLmmol$^{-1}$) was stirred at room temperature for 24 hours. The reaction was then washed with sodium hydroxide solution and the organic solution was evaporated under reduced pressure. The crude product was purified by column chromatography on silica gel using an elution gradient of dichloromethane:methanol:0.88 ammonia (100:0:0 to 90:10:1) to afford the title compounds.

| Ex No | Data |
|---|---|
| 202 | Z=4-Chloro-3-fluorophenyl; X=CH$_3$; $^1$H NMR(400MHz, CD$_3$OD): δ 1.79-1.99(m, 4H), 2.23(s, 3H), 2.85(m, 2H), 3.11(m, 1H), 3.70(m, 1H), 4.58(m, 1H), 7.22(d, 1H), 7.37(d, 1H), 7.45(d, 2H), 7.58(m, 1H), 7.64(d, 2H). LCMS: m/z APCl+ 433[M]+ |
| 203 | Z=2,3,4-Trifluorophenyl; X=CH$_3$; $^1$H NMR(400MHz, CD$_3$OD): δ 1.82(m, 3H), 1.98(m, 1H), 2.22(s, 2H), 2.89(m, 2H), 3.15(m, 1H), 3.60(m, 1H), 4.60(m, 1H), 7.12(m, 2H), 7.44(m, 2H), 7.66(m, 2H). LCMS: m/z APCl+ 435[M]+ |

EXAMPLES 205 TO 207

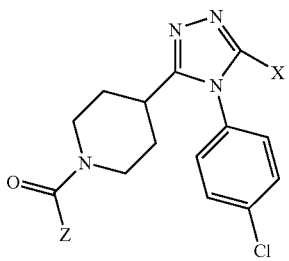

-continued

| Ex No | Data |
|---|---|
| 204 | Z=1H-Indazol-3-yl; X=3-methyl-isoxazol-5-ylmethyl; $^1$H NMR(400MHz, CDCl$_3$): δ 1.80-2.15(m, 5H), 2.18(s, 3H), 2.75(m, 1H), 2.80-2.92(m, 2H), 3.17(m, 1H), 4.04(s, 2H), 4.62-4.81(m, 2H), 4.86(s, 1H), 7.15(m, 3H), 7.30(dd, 1H), 7.50(m, 3H), 8.00(d, 1H), 11.90(br s, 1H). LCMS: m/z ES$^+$ 500, 502[M]$^+$ |

A solution of the appropriate acid, ZCO$_2$H (1.2 eq.), O-benzotriazol-1-yl-N,N,N',N'-tetramethyluronium hexafluorophosphate (1.2 eq.), N-methylmorpholine (1.4 eq.) and the appropriate amine selected from preparations 12 and 136 (1 eq.) in dichloromethane (7 to 10 mLmmol$^{-1}$) was stirred at room temperature for 24 hours. The reaction was then partitioned between sodium hydroxide solution and dichloromethane, and the layers were separated. The organic solution was washed with ammonium chloride solution, dried over MgSO$_4$ and then it was evaporated under reduced pressure. The crude product was purified by column chromatography on silica gel using an elution gradient of dichloromethane:methanol:0.88 ammonia (100:0:0 to 90:10:1) to afford the title compounds.

| Ex No | Data |
|---|---|
| 205[A] | Z=3-Difluoromethyl-phenyl; X=[1,2,3]-triazol-2-ylmethyl $^1$H NMR(400MHz, CDCl$_3$): δ 1.78-2.02(m, 4H), 2.70(m, 1H), 2.95(m, 2H), 3.80(m, 1H), 4.58(m, 1H), 5.63(s, 2H), 6.50-6.80(t, 1H), 7.01(d, 2H), 7.42-7.58(m, 8H). LCMS: m/z APCl$^+$ 498, 500[MH]$^+$ |
| 206[B,C] | Z=4-Difluoromethyl-phenyl; X=[1,2,3]-triazol-2-ylmethyl $^1$H NMR(400MHz, CDCl$_3$): δ 1.78(m, 2H), 1.97(m, 2H), 2.66(m, 1H), 2.90(m, 2H), 3.78(m, 1H), 4.58(m, 1H), 5.61(s, 2H), 6.46-6.78(t, 1H), 6.98(d, 2H), 7.22(s, 2H), 7.39-7.57(m, 8H). LCMS: m/z APCl$^+$ 498, 500[MH]$^+$ |
| 207 | Z=1H-Indazol-3-yl; X=2-piperidin-1-yl-ethyl; $^1$H NMR(400MHz, CDCl$_3$): δ 1.38(m, 2H), 1.50(m, 4H), 1.74-2.18(m, 4H), 2.30(m, 4H), 2.72(m, 6H), 2.88(m, 1H), 3.19(m, 1H), 4.61-4.88(m, 2H), 7.18(m, 3H), 7.30(m, 1H), 7.54(m, 3H), 8.02(d, 1H). LCMS: m/z APCl$^+$ 518[M]$^+$ |

[A] = 3-difluoromethyl benzoic acid was used. It can be prepared according to Tetrahedron 31; 1977; 391-401.
[B] = 4-difluoromethyl benzoic acid was used. It can be prepared according to Tetrahedron 31; 1977; 391-401.
[C] = product additionally recrystallised from isopropyl alcohol, and 2.8 eq of N-methylmorpholine was used.

EXAMPLES 208 TO 210

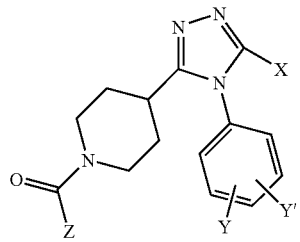

A mixture of the appropriate oxadiazole selected from preparations 66 and 67 (1 eq.), the appropriate aniline from preparations 166 and 168 or commercially available 4-chloro-2-(trifluoromethoxy)phenylamine (1.5 to 2.0 eq.) and trifluoroacetic acid (0.5 to 1.0 eq.) in toluene (2.5 to 9.5 mLmmol$^{-1}$) was heated at 110° C. for 18 hours. The cooled mixture was partitioned between dichloromethane and sodium carbonate solution, and the layers were then separated. The organic phase was dried over MgSO$_4$ and evaporated under reduced pressure. The crude product was purified by column chromatography on silica gel using dichloromethane:methanol:0.88 ammonia (100:0:0 to 90:10:1) as eluant to afford the title compounds.

| Ex No | Data |
|---|---|
| 208 | Z=3-Chlorophenyl; Y=4-Cl; Y'=2-OCH$_2$CH$_3$; X=H; $^1$H NMR(400MHz, CD$_3$OD): δ 1.23(t, 3H), 1.78-1.98(m, 4H), 2.92(m, 2H), 3.16(m, 1H), 3.70(m, 1H), 4.14(q, 2H), 4.58(m, 1H), 7.18(d, 1H), 7.34(m, 2H), 7.42(m, 3H), 8.43(s, 1H). LCMS: m/z APCl$^+$ 445[M]$^+$ |
| 209 | Z=3-Chlorophenyl; Y=4-Cl; Y'=2-OCF$_3$; X=H; $^1$H NMR(400MHz, CD$_3$OD): δ 1.80-1.98(m, 4H), 2.84-2.99(m, 2H), 3.10-3.20(m, 1H), 3.72(m, 1H), 4.60(m, 1H), 7.37(d, 1H), 7.44(m, 3H), 7.70(m, 2H), 7.78(s, 1H), 8.62(s, 1H). LCMS: m/z APCl$^+$ 485[M]$^+$ |
| 210 | Z=4-Chlorophenyl; Y=4-Cl; Y'=2-pyrrolidin-1-ylmethyl; X=CH$_3$; $^1$H NMR(400MHz, CDCl$_3$): δ 1.64-1.84(m, 7H), 2.18(s, 3H), 2.37(m, 4H), 2.58(m, 1H), 2.78-2.99(m, 2H), 3.16-3.20(m, 2H), 3.64-3.95(m, 1H), 4.45-4.70(m, 1H), 7.09(m, 1H), 7.30-7.44(m, 5H), 7.62(s, 1H). LCMS: m/z APCl$^+$ 498[M]$^+$ |

EXAMPLES 211 TO 216

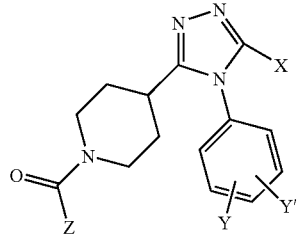

A mixture of the appropriate oxadiazole selected from preparations 66 to 69, 71 and 75 (1 eq.), aniline (1.5 to 2.0 eq.) and trifluoroacetic acid (0.5 to 1.0 eq.) in toluene (1.0 to 2.5 mLmmol$^{-1}$) was heated at 170 to 185° C. for 20 minutes under microwave radiation. The crude solution was purified by column chromatography on a silica gel cartridge using dichloromethane:methanol:0.88 ammonia (100:0:0 to 90:10:1) as eluant to afford the title compounds.

| Ex No | Data |
|---|---|
| 211 | Z=3-Chlorophenyl; Y=4-Cl; Y'=2-OCH$_2$CF$_3$; X=H; $^1$H NMR(400MHz, CDCl$_3$): δ 1.78-2.02(m, 4H), 2.80(m, 1H), 2.95-3.06(m, 2H), 3.81(m, 1H), 4.40(q, 2H), 4.58(m, 1H), 7.17(s, 1H), 7.25(m, 3H), 7.38(m, 3H), 8.18(s, 1H). LCMS: m/z APCl$^+$ 499[M]$^+$ |
| 212$^A$ | Z=4-Chlorophenyl; Y=4-Cl; Y'=H; X=CF$_3$; $^1$H NMR(400MHz, CDCl$_3$): δ 1.82(m, 2H), 2.00(m, 2H), 2.76(m, 1H), 2.83-3.02(m, 2H), 3.83(m, 1H), 4.60(m, 1H), 7.22(d, 2H), 7.37(d, 2H), 7.40(d, 2H), 7.60(d, 2H). LCMS: m/z APCl$^+$ 469[M]$^+$ |
| 213 | Z=3-Chlorophenyl; Y=4-Cl; Y'=H; X=CH$_2$OCH$_2$CH$_3$; $^1$H NMR(400MHz, CDCl$_3$): δ 1.08(t, 3H), 1.78-1.90(m, 2H), 1.92-2.02(m, 2H), 2.78(m, 1H), 2.80-3.02(m, 2H), 3.41(q, 2H), 3.80(m, 1H), 4.41(s, 2H), 4.60(m, 1H), 7.24(m, 3H), 7.36(m, 2H), 7.57(d, 2H). LCMS: m/z APCl$^+$ 459[M]$^+$ |
| 214 | Z=4-Chlorophenyl; Y=4-CH$_3$; Y'=2-CH$_3$; X=CH$_3$; $^1$H NMR(400MHz, CDCl$_3$): δ 1.68-2.00(m, 7H), 2.14(s, 3H), 2.40(s, 3H), 2.58(m, 1H), 2.78-2.98(m, 2H), 3.78(m, 1H), 4.54(m, 1H), 6.97(m, 1H), 7.15(m, 1H), 7.20(s, 1H), 7.30(d, 2H), 7.36(d, 2H). LCMS: m/z APCl$^+$ 409[MH]$^+$ |
| 215 | Z=4-Chlorophenyl; Y=4-Cl; Y'=2-CH$_3$; X=CH$_2$CH$_3$; $^1$H NMR(400MHz, CDCl$_3$): δ 1.20(t, 3H), 1.68-2.02(m, 6H), 2.14(m, 1H), 2.38-2.58(m, 3H), 2.79-2.98(m, 2H), 3.80(m, 1H), 4.58(m, 1H), 7.04(m, 1H), 7.26-7.39(m, 5H), 7.41(s, 1H). LCMS: m/z ES$^+$ 443, 446[MH]$^+$ |
| 216 | Z=3-chlorophenyl; Y=4-Cl; Y'=H; X=pyrazol-1-ylmethyl; $^1$H NMR(400MHz, CD$_3$OD): δ 1.80-1.97(m, 4H), 2.82(m, 2H), 3.06(m, 1H), 3.69(m, 1H), 4.58(m, 1H), 5.41(s, 2H), 6.18(s, 1H), 7.20(m, 2H), 7.30(m, 2H), 7.38-7.57(m, 5H). LCMS: m/z APCl$^+$ 481[M]$^+$ |
| 217$^A$ | R$^4$=H; R$^5$=bicyclo[1.1.1]pent-1-yl; X=CH$_3$; $^1$H NMR(400MHz, CDCl$_3$): δ 1.58-1.78(m, 4H), 1.86(m, 3H), 2.02(m, 5H), 2.22(s, 3H), 2.79(m, 2H), 3.32(m, 2H), 5.90(s, 1H), 7.24(d, 2H), 7.54(d, 2H). LCMS: m/z APCl$^+$ 386[MH]$^+$ |
| 218 | R$^4$=H; R$^5$=t-butyl; X=[1,2,3]-triazol-2-ylmethyl $^1$H NMR(400MHz, CDCl$_3$): δ 1.29(s, 9H), 1.55-1.74(m, 4H), 1.99-2.09(m, 1H), 2.80(m, 2H), 3.38(m, 2H), 5.23(m, 1H), 5.59(s, 2H), 7.10(d, 2H), 7.40(d, 2H), 7.52(s, 2H). LCMS: m/z APCl$^+$ 443[MH]$^+$ |
| 219 | NR$^4$R$^5$=azetidin-1-yl; X=[1,2,3]-triazol-2-ylmethyl $^1$H NMR(400MHz, CDCl$_3$): δ 1.56-1.68(m, 4H), 2.18-2.30(m, 3H), 2.80(m, 2H), 3.37(m, 2H), 3.98(t, 2H), 4.16(t, 2H), 5.59(s, 2H), 7.10(d, 2H), 7.40(d, 2H), 7.55(s, 2H). LCMS: m/z ES$^+$ 427[MH]$^+$ |
| 220 | NR$^4$R$^5$=pyrrolidin-1-yl; X=[1,2,3]-triazol-2-ylmethyl $^1$H NMR(400MHz, CDCl$_3$): δ 1.59-1.76(m, 4H), 1.82(m, 2H), 1.95(m, 2H), 2.41(m, 1H), 2.82(m, 2H), 3.36-3.46(m, 6H), 5.59(s, 2H), 7.15(d, 2H), 7.40(d, 2H), 7.55(s, 2H). LCMS: m/z ES$^+$ 441[MH]$^+$ |
| 221 | NR$^4$R$^5$=morpholin-4-yl; X=[1,2,3]-triazol-2-ylmethyl $^1$H NMR(400MHz, CDCl$_3$): δ 1.58-1.78(m, 4H), 2.56(m, 1H), 2.82(m, 2H), 3.38(m, 2H), 3.44(m, 2H), 3.60(m, 2H), 3.62(m, 4H), 5.60(s, 2H), 7.12(d, 2H), 7.40(d, 2H), 7.52(s, 2H). LCMS: m/z ES$^+$ 457[MH]$^+$ |
| 222 | R$^4$=H; R$^5$=2-phenylethyl; X=[1,2,3]-triazol-2-ylmethyl $^1$H NMR(400MHz, CDCl$_3$): δ 1.52-1.68(m, 4H), 2.04(m, 1H), 2.79(m, 4H), 3.36(m, 2H), 3.47(m, 2H), 5.40(m, 1H), 5.59(s, 2H), 7.10(d, 2H), 7.17(d, 2H), 7.20-7.36(m, 3H), 7.40(d, 2H), 7.54(s, 2H). LCMS: m/z ES$^+$ 491[MH]$^+$ |

$^A$= Crude reaction mixture was partitioned between ethyl acetate and 2N hydrochloric acid, then the organic solution washed with saturated sodium bicarbonate solution and evaporated under reduced pressure.

$^A$= 1-bicyclo[1.1.1]pentylamine hydrochloride (see ref. J.O.C. 2001; 66(19); 6282-6285).

EXAMPLES 217 TO 222

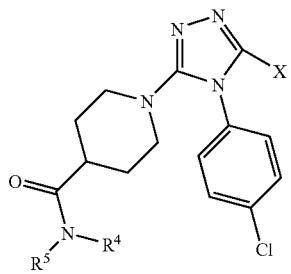

A solution of the appropriate acid selected from preparation 158 and 159 (1 eq.), 1-hydroxybenzotriazole hydrate (1.5 eq.), triethylamine (4 eq.) and 1-(3-dimethylaminopropyl)-3-ethylcarbodiimide hydrochloride (1.5 eq.) in dichloromethane (3.5 mLmmol$^{-1}$) was added to a solution of the appropriate amine (HNR$^4$R$^5$) (1.5 eq.) in dichloromethane (2.5 mLmmol$^{-1}$) and the reaction was stirred at room temperature for 24 hours. The reaction was then washed with ammonium chloride solution, and the organic solution was evaporated under reduced pressure. The crude product was purified by column chromatography on silica gel using an elution gradient of dichloromethane:methanol:0.88 ammonia (100:0:0 to 95:5:0.5) to afford the title compounds.

EXAMPLE 223

1-[4-(4-Chlorophenyl)-5-methyl-4H-1,2,4-triazol-3-yl]-N-isopropyl-4-methylpiperidine-4-carboxamide

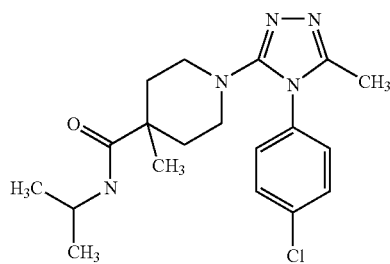

Oxalyl chloride (0.04 mL, 0.55 mmol) was added to a solution of the acid of preparation 160 (50 mg, 0.15 mmol) in dichloromethane (50 mL), and the solution was stirred at room temperature for 20 minutes. Additional oxalyl chloride (0.02 mL, 0.27 mmol) was added and the solution was stirred for a further 10 minutes. The solution was then evaporated under reduced pressure and the residue was azeotroped with dichloromethane (3×). The oily residue was dissolved in dichloromethane (10 mL). Isopropylamine (0.19 mL, 2.25 mmol) was added to the solution and the mixture was then stirred at room temperature for 18 hours. The reaction was then washed with ammonium chloride solution, dried over MgSO$_4$ and then evaporated under reduced pressure. The residue was purified by column chromatography on silica gel using dichloromethane:methanol:0.88 ammonia (95:5:1) as eluant. The product was triturated with ether to afford the title compound as a solid, 30 mg.

$^1$H NMR (400 MHz, CDCl$_3$): δ 1.15 (m, 9H), 1.42 (m, 2H), 1.95 (m, 2H), 2.22 (s, 3H), 3.02 (m, 2H), 3.18 (m, 2H), 4.03 (m, 1H), 5.38 (m, 1H), 7.26 (d, 2H), 7.57 (d, 2H); LCMS: m/z APCI$^+$ 376 [MH]$^+$

EXAMPLE 224

N-{1-[4-(4-Chlorophenyl)-5-methyl-4H-1,2,4-triazol-3-yl]piperidin-4-yl}benzamide

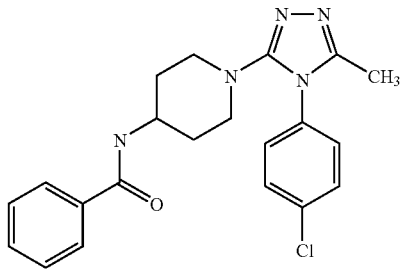

Triethylamine (105 µL, 0.75 mmol) and then benzoyl chloride (79.6 µL, 0.69 mmol) were added to a solution of the amine of preparation 145 (200 mg, 0.69 mmol) in dichloromethane (5 mL), and the reaction was stirred at room temperature for 5 minutes. Water (5 mL) was added and the mixture was stirred vigorously for 5 minutes. The mixture was then filtered using a phase separation cartridge and the organic layer was concentrated under reduced pressure. The residue was then azeotroped with ether to provide the title compound as an off-white solid, 278 mg.

$^1$H NMR (400 MHz, CD$_3$OD): δ 1.55 (m, 2H), 1.86 (m, 2H), 2.22 (s, 3H), 2.93 (m, 2H), 3.52 (m, 2H), 3.97 (m, 1H), 7.42 (t, 2H), 7.45-7.53 (m, 3H), 7.63 (d, 2H), 7.75 (d, 2H); LCMS: m/z APCI$^+$ 418 [MNa]$^+$

EXAMPLE 225

1-Benzoyl-4-[4-(4-chlorophenyl)-5-methyl-4H-1,2,4-triazol-3-yl]piperazine

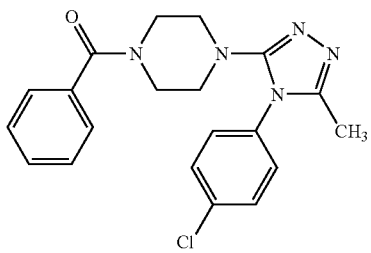

1-Hydroxybenzotriazole hydrate (150 mg, 1.1 mmol), 1-(3-dimethylaminopropyl)-3-ethylcarbodiimide hydrochloride (225 mg, 1.17 mmol), triethylamine (0.4 mL, 2.7 mmol) and the amine of preparation 144 (250 mg, 0.9 mmol) were added sequentially to a solution of benzoic acid (110 mg, 0.9 mmol) in dichloromethane (10 mL). The reaction was then stirred at room temperature for 18 hours. The mixture was partitioned between 2M sodium hydroxide solution and dichloromethane, and then the phases were separated. The aqueous layer was further extracted with dichloromethane, and the combined organic solutions were evaporated under reduced pressure. The crude product was purified by column chromatography on silica gel using an elution gradient of dichloromethane:methanol:0.88 ammonia (100:0:0 to 95:5:0.5) to afford the title compound as a white foam, 182 mg.

$^1$H NMR (400 MHz, CDCl$_3$): δ 2.22 (s, 3H), 3.08 (m, 4H), 3.38-3.78 (m, 4H), 7.25 (d, 2H), 7.39 (m, 4H), 7.54 (d, 3H). LCMS: m/z APCI$^+$ 382 [MH]$^+$; Microanalysis found: C, 61.66; H, 5.32; N, 17.42. C$_{20}$H$_{20}$ClN$_5$O; 0.14CH$_2$Cl$_2$ requires C, 61.43; H, 5.19; N, 17.79%.

EXAMPLE 226

4-Benzoyl-1-[4-(4-chlorophenyl)-5-(methoxymethyl)-4H-1,2,4-triazol-3-yl]-2-methylpiperazine

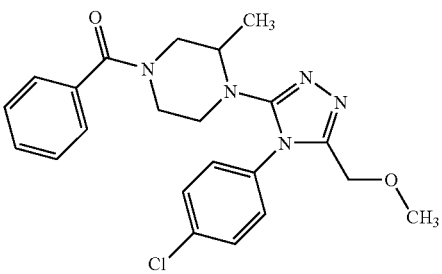

Triethylamine (100 µL, 0.71 mmol), and then benzoyl chloride (82 µL, 0.71 mmol) were added to a solution of the compound of preparation 149 (150 mg, 0.47 mmol) in dichloromethane (10 mL), and the reaction was then stirred at room temperature for 18 hours. The mixture was washed with sodium bicarbonate solution, the layers separated and the organic solution evaporated under reduced pressure. The crude product was purified by column chromatography on silica gel using ethyl acetate:methanol:0.88 ammonia (95:5:0.5) as eluant to afford the title compound as a white solid, 120 mg.

$^1$H NMR (400 MHz, CDCl$_3$): δ 1.01-1.16 (m, 3H), 3.18-3.23 (m, 3H), 3.30 (s, 3H), 3.39-3.48 (m, 3H), 3.83 (m, 1H), 4.04 (m, 1H), 4.28 (d, 1H) 4.38 (d, 1H), 7.39 (m, 7H), 7.52 (d, 2H); LCMS: m/z APCI$^+$ 426 [MH]$^+$

EXAMPLE 227

1-(4-Chlorobenzoyl)-4-[4-(4-chlorophenyl)-5-(methoxymethyl)-4H-1,2,4-triazol-3-yl]-2-methylpiperazine

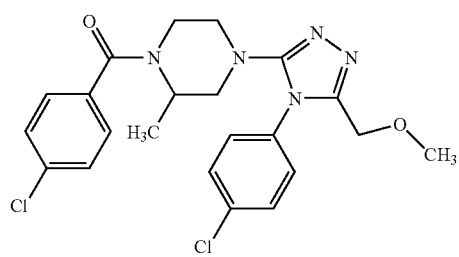

The title compound was prepared from the compound of preparation 150 and 4-chlorobenzoyl chloride in 37% yield, following the procedure described for example 226.

¹H NMR (400 MHz, CDCl₃): δ 1.08 (d, 3H), 2.94-3.39 (m, 8H), 4.34 (s, 2H), 7.25 (d, 2H), 7.39 (m, 4H), 7.54 (d, 2H); LCMS: m/z APCI⁺ 460 [M]⁺

EXAMPLE 228

1-[4-(4-Chlorophenyl)-5-(methoxymethyl)-4H-1,2,4-triazol-3-yl]-4-(3-fluorobenzoyl)-1,4-diazepane

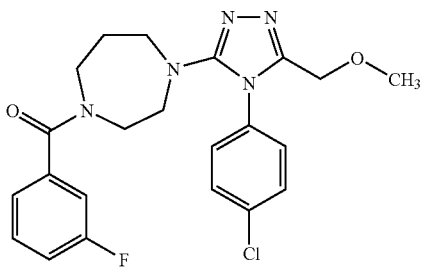

The title compound was prepared from the compound of preparation 148 and 3-fluorobenzoyl chloride in 84% yield, following the procedure described for example 224.

¹H NMR (400 MHz, CDCl₃): δ 1.68-1.80 (m, 2H) 3.17 (m, 1H), 3.25 (s, 3H), 3.39 (m, 4H), 3.58 (m, 1H), 3.65 (m, 1H), 3.78 (m, 1H), 4.22 (d, 2H), 7.02 (d, 1H), 7.10 (m, 2H), 7.22-7.42 (m, 3H), 7.49 (m, 2H); LCMS: m/z APCI⁺ 444 [M]⁺

EXAMPLE 229

4-(2-Chlorobenzoyl)-2-[4-(4-chlorophenyl)-5-methyl-4H-1,2,4-triazol-3-yl]morpholine

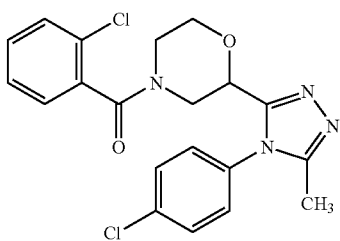

Trifluoroacetic acid (5 mL) was added to a cooled (5° C.) solution of the compound of preparation 102 (1.3 g, 3.43 mmol) in dichloromethane (5 mL), and the solution was then stirred at room temperature for 2 hours. The mixture was concentrated under reduced pressure, and then triethylamine (450 mg, 4.47 mmol) and dichloromethane (30 mL) were added.

A portion of this solution (10 mL) was treated with 2-benzoyl chloride (1.26 mmol) and then stirred for 2 hours at room temperature. Tris-(2-aminoethyl)amine polystyrene (500 mg) was added and the mixture stirred for a further 24 hours. The mixture was then diluted with aqueous ammonium chloride solution, the layers were separated using a hydrophobic membrane and the organic solution was purified directly using a silica gel cartridge and dichloromethane:methanol (100:0 to 95:5) as eluant to provide the title compound.

¹H NMR (400 MHz, CDCl₃)(rotamers): δ 2.23, 2.34 (2×s, 3H), 3.00-3.62 (m, 3H), 3.64-4.00 (m, 2H), 4.11-4.40 (m, 1H), 4.58, 4.90 (2×m, 1H), 7.17-7.40 (m, 6H), 7.56 (m, 2H); LCMS: m/z ES⁺ 439 [MNa]⁺

EXAMPLE 230

1-(2-Chlorobenzoyl)-3-[4-(4-chloro-2-methylphenyl)-5-methyl-4H-1,2,4-triazol-3-yl]piperidine

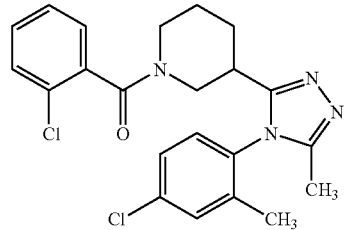

Triethylamine (79 μL, 0.57 mmol) and then 2-benzoyl chloride (66 μL, 0.52 mmol) were added to a solution of the compound of preparation 146 (150 mg, 0.52 mmol) in dichloromethane (5 mL). The mixture was then stirred at room temperature for 18 hours. After this time the reaction was diluted with water (5 mL) and the mixture was stirred rapidly for 30 minutes. The layers were then separated, the organic solution evaporated under reduced pressure and the product was azeotroped from ether to afford the title compound as a white foam, 193 mg.

¹H NMR (400 MHz, CDCl₃): δ 1.38-1.82 (m, 3H), 1.82-2.22 (m, 8H), 2.54-2.87 (m, 1H), 3.03-3.50 (m, 2H), 4.80 (m, 1H), 6.94-7.50 (m, 7H); LCMS: m/z ES⁺ 451 [MNa]⁺

EXAMPLE 231

3-[1-(2-Chlorobenzoyl)pyrrolidin-3-yl]-4-(4-chloro-2-methylphenyl)-5-methyl-4H-1,2,4-triazole

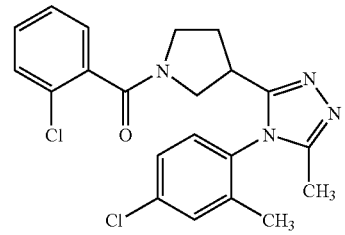

A mixture of the compound of preparation 147 (97 mg, 0.35 mmol), 2-chlorobenzoyl chloride (40.4 μL, 0.32 mmol) and N-methylmorpholine (58 μL, 0.53 mmol) in dichloromethane (5 mL) was stirred at room temperature for 18 hours. The reaction was then diluted with dichloromethane (20 mL), washed with 2N hydrochloric acid (20 mL) and saturated sodium bicarbonate solution (20 mL). The organic solution was then dried over MgSO₄ and concentrated under reduced pressure. The residual oil was triturated with ether, the resulting solid filtered off and then dried to afford the title compound, 55 mg.

¹H NMR (400 MHz, CDCl₃)(rotamers): δ 1.84-2.62 (m, 8H), 3.00-3.20 (m, 1H), 3.22-3.42 (m, 1H), 3.44-3.79 (m, 2H), 3.81-3.98 (m, 1H), 7.20-7.50 (m, 7H); LCMS: m/z APCI⁺ 415 [MH]⁺

EXAMPLE 232

N-{1-[4-(4-Chlorophenyl)-5-(2H-1,2,3-triazol-2-ylmethyl)-4H-1,2,4-triazol-3-yl]pyrrolidin-3-yl}-N-methylacetamide

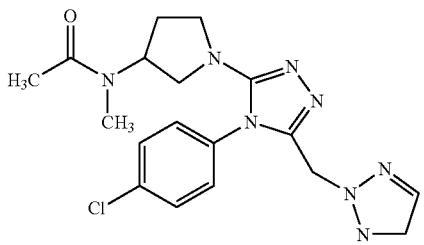

The title compound was obtained as a solid in 50% yield from the compounds of preparations 54 and 18, following the procedure described for preparation 93. ¹H NMR (400 MHz, CDCl₃)(rotamers): δ 1.78-1.90 (m, 2H), 2.04 (s, 3H), 2.74 (s, 1H), 2.80 (s, 3H), 2.98 (m, 1H), 3.04-3.18 (m, 2H), 3.22-3.38 (m, 2H), 4.40, 5.21 (2×m, 1H), 5.55 (m, 2H), 7.03 (d, 2H), 7.38 (d, 2H), 7.52 (s, 2H); LCMS: m/z ES⁺ 423 [MNa]⁺

EXAMPLE 233

1-[4-(4-Chlorophenyl)-5-methyl-4H-1,2,4-triazol-3-yl]-4-phenylpiperidine-4-carboxamide

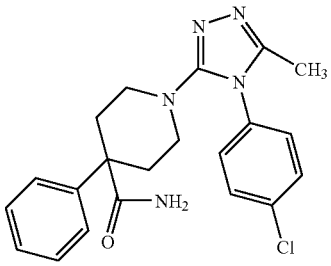

Sulphuric acid (930 mg, 95%, 9.5 mmol) was added to a solution of the compound of preparation 96 (700 mg, 1.9 mmol) in acetic acid (1.5 mL), and the reaction was then heated at 100° C. for 3 days. The cooled mixture was carefully quenched by the addition of 0.88 ammonia and then extracted with dichloromethane (4×). The combined organic layers were washed with brine, then dried over MgSO₄ and evaporated under reduced pressure. The product was crystallised from ethyl acetate to afford the title compound, 282 mg.

¹H NMR (400 MHz, CDCl₃): δ 2.06 (m, 2H), 2.20 (s, 3H), 2.32 (m, 2H), 3.05-3.20 (m, 4H), 5.20 (m, 2H), 7.24 (m, 3H), 7.38 (m, 4H), 7.52 (d, 2H); LCMS: m/z ES⁺ 396 [MH]⁺

EXAMPLE 234 tert-Butyl 4-{[4-(4-chlorophenyl)-5-(2H-1,2,3-triazol-2-ylmethyl)-4H-1,2,4-triazol-3-yl]oxy}piperidine-1-carboxylate

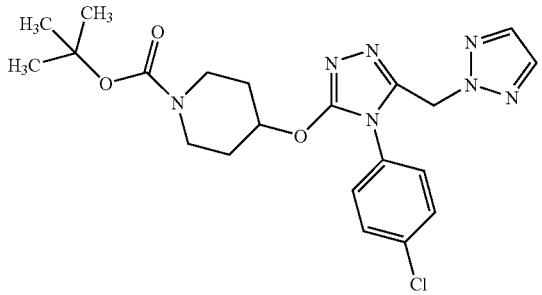

Tetrahydrofuran (2 mL) was added to sodium hydride (24 mg, 60% in mineral oil), which had been pre-washed with pentane (2 mL), and the suspension was stirred at room temperature. tert-Butyl 4-hydroxy-1-piperidinecarboxylate (119 mg, 0.6 mmol) was then added and the mixture was stirred at room temperature for a further 30 minutes. The compound of preparation 164 (100 mg, 0.3 mmol) was added and the reaction was stirred at room temperature for a further 18 hours. The reaction was then partitioned between dichloromethane (20 mL) and brine (20 mL), the layers separated and the organic phase evaporated under reduced pressure. The residue was dissolved in dichloromethane (6 mL), PS-DIEA (Argonaut Technologies) (638 mg) and triethylamine (0.5 mL, 3.6 mmol) was added. The mixture was then stirred for 18 hours. The mixture was filtered, the filtrate was washed with saturated aqueous potassium carbonate solution and evaporated under reduced pressure. The crude product was purified by column chromatography on silica gel using dichloromethane:methanol (99:1) as eluant. The product was further purified by HPLC using a Phenomenex Luna C18 column and 0.1% aqueous formic acid:acetonitrile/0.1% formic acid (80:20 to 5:95) to afford the title compound, 34 mg.

¹H NMR (400 MHz, CD₃OD): δ 1.40 (m, 9H), 1.62 (m, 2H), 1.98 (m, 2H), 3.30-3.59 (m, 4H), 4.90-5.02 (m, 1H), 5.61 (s, 2H), 7.18 (d, 2H), 7.40 (d, 2H), 7.50 (m, 2H).

EXAMPLE 235

N-(tert-Butyl)-4-[4-(4-chlorophenyl)-5-methyl-4H-1,2,4-triazol-3-yl]benzamide

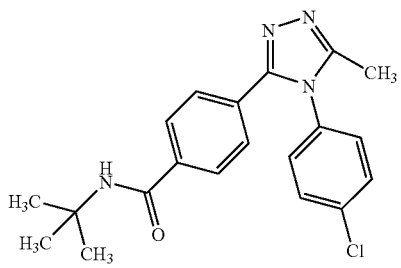

tert-Butylamine hydrochloride (223 mg, 2.0 mmol), followed by a solution of the acid chloride of preparation 157 (150 mg, 0.4 mmol) in dichloromethane (3 mL), was added to a solution of triethylamine (300 μL, 2.0 mmol) in dichloromethane (2 mL) and the reaction was stirred at room temperature for an hour. The mixture was then partitioned between dichloromethane and aqueous citric acid solution, and the phases were separated. The aqueous layer was further extracted with dichloromethane (2×25 mL) and the combined organic solutions were dried over MgSO$_4$ and evaporated under reduced pressure. The crude product was purified by column chromatography on silica gel using dichloromethane: methanol:0.88 ammonia (93:7:1) as eluant to afford the title compound, 122 mg.

$^1$H NMR (400 MHz, CDCl$_3$): δ 1.42 (s, 9H), 2.40 (s, 3H), 5.98 (br s, 1. H), 7.19 (d, 2H), 7.41 (d, 2H), 7.50 (d, 2H), 7.61 (d, 2H); LCMS: m/z ES$^+$ 391 [MNa]$^+$

EXAMPLES 236 TO 395

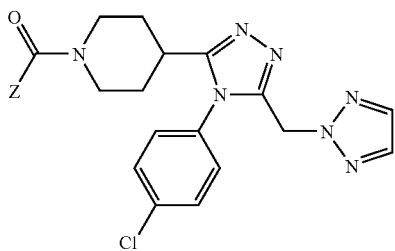

The appropriate acid, ZCO$_2$H, (0.25 mL, 0.2M solution in N,N-dimethylformamide, 50 μmol) was, if necessary, neutralised with triethylamine (7 μl, 50 μmol per salt equivalent) and then treated with O-(7-azabenzotriazol-yl)-N,N,N',N'-tetramethyluronium hexafluorophosphate solution (0.1 mL, 0.525 M, 52.5 μmol). The solution was then treated with triethylamine (28 μl, 0.20 mmol) and the amine of preparation 12 (0.25 mL, 0.2M solution in N,N-dimethylformamide, 50 μmol) in a 96 deep-well polypropylene microtitre plate. The plate was sealed and agitated for 16 hours at 40° C. The reaction mixtures were then evaporated under reduced pressure and the residues were purified by HPLC using a Waters XTerra MS C18 column, and acetonitrile: 10 mM ammonium hydrogen carbonate (adjusted to pH 10 with ammonium hydroxide) (5:95 to 98:2), to provide the desired compounds.

| Time | % A | % B | % D |
| --- | --- | --- | --- |
| 0 min | 94 | 5 | 1 |
| 3.5 min | 4.5 | 95 | 0.5 |
| 4.0 min | 4.5 | 95 | 0.4 |

| Ex No | Z | MS [MH]$^+$ | Retention time (min) |
| --- | --- | --- | --- |
| 236 | 5-methyl-1-phenyl-1H-pyrazol-4-yl | 529 | 2.26 |
| 237 | 5-methyl-1H-indol-2-yl | 502 | 2.56 |
| 238 | 3-(1H-indol-3-yl)propyl | 530 | 2.17 |
| 239 | 1-benzyl-1H-pyrazol-4-yl | 529 | 2 |
| 240 | 3-(2-fluorophenyl)-1H-pyrazol-5-yl | 533 | 2.08 |
| 241 | 3-(4-methylphenyl)-1H-pyrazol-5-yl | 529 | 2.17 |
| 242 | 2-(phenylmethyl)thiazol-4-yl | 546 | 2.26 |
| 243 | 5-methyl-1H-indazol-3-yl | 503 | 2.04 |
| 244 | (2,5,7-trimethyl-1H-indol-3-yl)methyl | 544 | 2.3 |
| 245 | 4,5,6,7-tetrahydro-2-methyl-2H-indazol-3-yl | 507 | 1.95 |
| 246 | 1H-indazol-1-ylmethyl | 503 | 1.95 |
| 247 | 3-(2,5-dimethylphenyl)propyl | 519 | 2.47 |
| 248 | (1S)-1-(dimethylamino)-2-phenylethyl | 520 | 2.04 |
| 249 | (2,5-dimethyl-1,3-thiazol-4-yl)methyl | 498 | 1.87 |
| 250 | (4-methoxyphenyl)-5-methyl-1H-pyrazol-4-yl] | 559 | 2.04 |
| 251 | 1-(1-cyclopenten-1-yl)butyl | 495 | 2.47 |
| 252 | cyclohex-3-en-1-yl | 453 | 2.04 |
| 253 | (1,3-dimethyl-1H-thieno[2,3-c]pyrazol-5-yl) | 523 | 1.91 |
| 254 | (2S)-1-(tert-butoxycarbonyl)piperidin-2-yl | 556 | 2.3 |
| 255 | benzo[b]thien-3-yl | 505 | 2.21 |
| 256 | 4-(5-oxazolyl)phenyl | 516 | 1.87 |
| 257 | 3-(2-methyl-4-thiazolyl)phenyl | 546 | 2.13 |
| 258 | 2-phenoxypyridin-5-yl | 542 | 2.21 |
| 259 | 2-methyl-4-phenylpyrimidin-5-yl | 541 | 1.95 |
| 260 | 5-methoxy-indol-2-yl | 518 | 2.13 |
| 261 | 4-chlorobenzyl | 497 | 2.43 |
| 262 | 1-phenylcyclopentyl | 517 | 2.69 |
| 263 | 3-(4-fluorophenyl)-3-oxopropyl | 523 | 2.03 |
| 264 | 1,2,3,4-tetrahydronaphthalen-2-yl | 503 | 2.23 |
| 265 | cyclopentyl(phenyl)methyl | 531 | 2.52 |
| 266 | biphenyl-4-ylmethyl | 539 | 2.37 |
| 267 | 1-(4-chlorophenoxy)-1-methylethyl | 541 | 2.5 |
| 268 | 1-(3-chlorophenoxy)ethyl | 527 | 2.23 |
| 269 | 2-methyl-1-phenylbutyl | 519 | 2.49 |
| 270 | (1-naphthyloxy)methyl | 529 | 2.13 |
| 271 | (2,3-dimethylphenoxy)methyl | 507 | 2.2 |
| 272 | 3-(4-methylphenyl)propyl | 505 | 2.18 |
| 273 | 1H-indol-1-ylethyl | 516 | 2.12 |
| 274 | (phenylthio)methyl | 495 | 2.08 |
| 275 | 1-(4-chlorophenyl)ethyl | 511 | 2.27 |
| 276 | 2,3-dihydro-1H-inden-2-ylmethyl | 503 | 2.23 |
| 277 | 2-[(4-chlorophenyl)thio]propyl | 558 | 2.47 |
| 278 | 2-chloro-4-fluorobenzyl | 515 | 2.13 |
| 279 | (1R)-1-phenyl-propyl | 491 | 2.22 |
| 280 | 3-methoxycyclohexyl | 485 | 1.81 |
| 281 | 1-benzyl-2,2-dimethylpropyl | 533 | 2.52 |
| 282 | 1-methyl-2-phenylethyl | 491 | 2.15 |
| 283 | (benzyloxy)methyl | 493 | 1.96 |
| 284 | 3-(4-chlorophenyl)-3-oxopropyl | 539 | 2.17 |
| 285 | [(4-chlorophenyl)thio]methyl | 529 | 2.27 |
| 286 | (benzylthio)methyl | 509 | 2.12 |
| 287 | 3-chlorobenzyl | 497 | 2.1 |
| 288 | 1,1-diphenylethyl | 553 | 2.5 |
| 289 | 2,2-diphenylethyl | 553 | 2.39 |
| 290 | (2,3-dichlorophenoxy)methyl | | |
| 291 | 4-fluorobenzyl | 548 | 2.29 |
| 292 | 2-methoxybenzyl | 481 | 1.98 |
| 293 | 2-(2-methoxyphenyl)ethyl | 493 | 1.91 |
| 294 | 2,8-dimethylquinolin-4-yl | 507 | 2.16 |
| 295 | (2-naphthyloxy)methyl | 528 | 2.21 |
| 296 | 2-naphthylmethyl | 529 | 2.29 |
| 297 | 2-phenoxyethyl | 513 | 2.26 |
| 298 | 1-(2-fluorophenyl)cyclopentyl | 493 | 2.11 |
| 299 | 5-methoxy-1-oxoindan-2-ylmethyl | 535 | 2.36 |
| 300 | (3-methylbenzoyl)aminomethyl | 520 | 1.89 |
| 301 | Anti-4-methylcyclohexyl | 469 | 2.26 |
| 302 | 3-phenyl-3-oxo-1methyl-propyl | 519 | 2.09 |
| 303 | 2-(2-methylphenyl)ethyl | 491 | 2.21 |
| 304 | 1-methyl-indol-3-ylmethyl | 516 | 2.14 |
| 305 | diphenylmethyl | 539 | 2.38 |
| 306 | 1-(4-chlorophenyl)-1-methylethyl | 525 | 2.41 |
| 307 | 1-methyl-1-phenylethyl | 491 | 2.26 |
| 308 | 1-acetyloxy-1-phenylmethyl | 521 | 2.01 |
| 309 | cyclohex-1-en-1-ylmethyl | 467 | 2.12 |
| 310 | (2R)-2-phenylpropyl | 491 | 2.19 |
| 311 | [(4-fluorophenyl)thio]methyl | 513 | 2.14 |
| 312 | (2R)-1-(tert-butoxycarbonyl)piperidin-2-yl | 556 | 2.26 |
| 313 | 3-(2,3-dihydro-1,4-benzodioxin-6-yl)propyl | 549 | 2.14 |
| 314 | 6-chloro-3-oxo-2,3-dihydro-4H-1,4-benzoxazin-4-yl | 568 | 2.11 |
| 315 | 2-(4-fluorophenoxy)ethyl | 511 | 2.16 |
| 316 | 2-hydroxyquinoxalin-3-yl | 517 | 1.57 |
| 317 | 5-methyl-3-phenylisoxazol-4-yl | 530 | 2.07 |
| 318 | isoquinolin-1-yl | 500 | 1.87 |
| 319 | 2-phenoxyphenyl | 541 | 2.29 |
| 320 | quinolin-2-yl | 500 | 1.97 |
| 321 | quinolin-4-yl | 500 | 1.8 |
| 322 | quinolin-3-yl | 500 | 1.87 |

-continued

| Ex No | Z | MS [MH]+ | Retention time (min) |
|---|---|---|---|
| 323 | 2-naphthyl | 499 | 2.21 |
| 324 | 5-butylpyridin-2-yl | 506 | 2.22 |
| 325 | 3-benzoylphenyl | 553 | 2.21 |
| 326 | 1H-benzimidazol-6-yl | 489 | 1.55 |
| 327 | 9-oxo-9H-fluoren-1-yl | 551 | 2.16 |
| 328 | 4-methoxyquinolin-2-yl | 530 | 2.07 |
| 329 | 1-benzofuran-2-yl | 489 | 2.16 |
| 330 | 2-(4-methylbenzoyl)phenyl | 567 | 2.31 |
| 331 | 7-methoxy-1-benzofuran-2-yl | 519 | 2.17 |
| 332 | 2,6-dimethoxypyridin-3-yl | 510 | 2.3 |
| 333 | 2,5-dimethyl-3-furyl | 467 | 2.26 |
| 334 | biphenyl-2-yl | 525 | 2.52 |
| 335 | 5-methyl-2-thienyl | 469 | 2.3 |
| 336 | 2-phenoxypyridin-3-yl | 542 | 2.17 |
| 337 | 1,3-benzothiazol-6-yl | 506 | 2.08 |
| 338 | 3-phenylcinnolin-4-yl | 577 | 1.76 |
| 339 | 3-tert-butyl-1-methyl-1H-pyrazol-5-yl | 509 | 2.26 |
| 340 | 2,1,3-benzoxadiazol-5-yl | 491 | 2.26 |
| 341 | 5-bromo-2,3-dihydro-1-benzofuran-7-yl | 570 | 2.43 |
| 342 | 1-(4-chlorophenyl)cyclopropyl | 523 | 2.27 |
| 343 | 5-isobutylisoxazol-3-yl | 496 | 2.23 |
| 344 | 3-(1H-pyrazol-1-yl)phenyl | 515 | 1.91 |
| 345 | 3,5-dimethylindol-2-yl | 516 | 2.32 |
| 346 | 4-(tert-butoxycarbonyl)morpholin-3-ylmethyl | 572 | 1.98 |
| 347 | 3-isobutyl-1H-pyrazol-5-yl | 495 | 1.96 |
| 348 | 5-propylisoxazol-3-yl | 482 | 2.1 |
| 349 | 2,4-dimethyl-1,3-thiazol-5-yl | 498 | 1.61 |
| 350 | 2-methylquinolin-4-yl | 514 | 1.81 |
| 351 | 6-chloro-imidazo[1,2-a]pyridin-2-yl | 523 | 1.71 |
| 352 | 3-phenyl-1H-pyrazol-5-yl | 515 | 1.96 |
| 353 | 3-isopropyl-1H-pyrazol-5-yl | 481 | 1.66 |
| 354 | 4,5,6,7-tetrahydro-2-indazol-3-yl | 493 | 1.81 |
| 355 | 2,3-dimethyl-1H-indol-5-yl | 516 | 2.05 |
| 356 | 3,5-dimethyl-1H-pyrrol-2-yl | 466 | 1.96 |
| 357 | 3-(3,5-dimethyl-1H-pyrazol-1-yl)phenyl | 543 | 2 |
| 358 | 3-[(3,5-dimethyl-1H-pyrazol-1-yl)methyl]phenyl | 557 | 1.98 |
| 359 | 3'-fluorobiphenyl-4-yl | 543 | 2.37 |
| 360 | 4-phenyl-1,3-thiazol-2-yl | 546 | 2.17 |
| 361 | 4-(1H-pyrazol-1-yl)phenyl | 515 | 1.9 |
| 362 | 5,7-dimethyl-pyrazolo[1,5-a]pyrimidin-2-yl | 518 | 1.76 |
| 363 | 3-phenylisoxazol-5-yl | 516 | 2.2 |
| 364 | 2,3-dihydro-1-benzofuran-2-yl | 491 | 2 |
| 365 | 1H-benzimidazol-1-ylmethyl | 503 | 1.73 |
| 366 | 5-(4-methoxyphenyl)-2-furyl | 545 | 2.25 |
| 367 | 1,3-benzothiazol-2-ylethyl | 534 | 2.03 |
| 368 | 2-methyl-5-propylpyrazol-3-yl | 495 | 1.96 |
| 369 | 1-benzyl-2-oxo-1,2-dihydropyridin-3-yl | 556 | 1.85 |
| 370 | 1-benzyl-6-oxo-1,6-dihydropyridin-3-yl | 556 | 1.75 |
| 371 | 2-phenyl-1,3-thiazol-4-yl | 532 | 2.22 |
| 372 | 4-methyl-2-phenyl-1,3-thiazol-5-yl | 546 | 2.18 |
| 373 | 8-methoxy-2H-chromen-3-yl | 533 | 2.02 |
| 374 | 2H-chromen-3-yl | 503 | 2.12 |
| 375 | 6-methoxy-2H-chromen-3-yl | 533 | 2.1 |
| 376 | 4-(tert-butoxycarbonyl)morpholin-3-yl | 558 | 1.95 |
| 377 | 4-methoxy-3-thienyl | 485 | 1.85 |
| 378 | 4-(1H-imidazol-1-yl)phenyl | 515 | 1.68 |
| 379 | 2-methyl-1H-benzimidazol-5-yl | 503 | 1.51 |
| 380 | 2,3-dihydro-1H-inden-2-yl | 489 | 2.15 |
| 381 | Trans-2-phenylcyclopropan-1-yl | 489 | 2.15 |
| 382 | 1-methyl-1H-indol-2-yl | 502 | 2.18 |
| 383 | 1-methyl-1H-indol-3-yl | 502 | 2.02 |
| 384 | 5-fluoro-1H-indol-2-yl | 506 | 2.13 |
| 385 | 6-methyl-4-oxo-4H-chromene-2-yl | 531 | 2.02 |
| 386[A] | 3-isopropyl-1-methylpyrazol-5-yl | 495 | 1.95 |
| 387[B] | 5-bromo-2-methoxypyridin-3-yl | 559 | 2.03 |
| 388[C] | 5-methyl-2-phenyl-1H-imidazol-4-yl | 529 | 1.95 |
| 389[D] | 3-(1-oxo-1,3-dihydro-2H-isoindol-2-yl)propyl | 532 | 1.82 |
| 390[E] | 1-ethylpiperidin-2-yl | 484 | 1.91 |
| 391[F] | 3-[(pyrimidin-2-ylthio)methyl]phenyl | 573 | 2.08 |
| 392[G] | 4-[(pyridin-2-ylthio)methyl]phenyl | 572 | 2.17 |
| 393[H] | 6-cyclohexyl-2-oxo-1,2,3,6-tetrahydropyrimidin-4-yl | 551 | 2.04 |
| 394[I] | 5-oxo-1-propylpyrrolidin-3-yl | 498 | 1.74 |
| 395[J] | 5-propylisoxazol-4-yl | 482 | 2 |

[A] = 3-isopropyl-1-methyl-1H-pyrazole-5-carboxylic acid was used; see DE 3029281.
[B] = 5-bromo-2-methoxynicotinic acid was used, see EP 306251, preparation I.
[C] = 5-methyl-2-phenyl-1H-imidazole-4-carboxylic acid was used, see J. Chem Soc. 1948; 1969.
[D] = 3-(1-oxo-1,3-dihydro-2H-isoindol-2-yl)propanoic acid was used, see J. Med. Chem. 83; 26(2); 243.
[E] = 1-ethylpiperidine-2-carboxylic acid was used, see Journal of Inorganic and Nuclear medicine; 1978; 40(6); 1103-6.
[F] = 3-[(pyrimidin-2-ylthio)methyl]benzoic acid was used, see J. Indian Chem. Soc.(97); 74(7); 575.
[G] = 4-[(pyridin-2-ylthio)methyl]benzoic acid was used, see U.S. Pat. No. 4,325,959, example 2.
[H] = 6-cyclohexyl-2-oxo-1,2,3,6-tetrahydropyrimidine-4-carboxylic acid was used, see J. O. C. 2000; 65(20); 6777.
[I] = 5-oxo-1-propylpyrrolidine-3-carboxylic acid was used, see WO 200202614.
[J] = 5-propylisoxazole-4-carboxylic acid was used, see J. Met. Chem. 1991; 28(2) 453.

EXAMPLES 396 TO 403

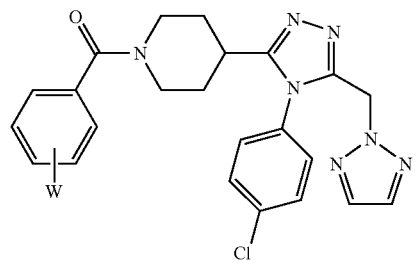

A mixture of the appropriate amine from preparation 12a (1 eq.), the appropriate acid chloride (1.2 to 1.4 eq.) and polymer supported N-ethyldiisopropylamine (10 eq.) in dichloromethane (16 mLmmol$^{-1}$) was stirred at room temperature for 2 hours. Tris-(2-aminoethyl)amine polystyrene was added and the mixture was stirred for an hour. It was then washed with 1N sodium hydroxide solution. The aqueous solution was extracted with dichloromethane (2×) and the combined organic solutions were concentrated under reduced pressure. The crude products were purified by column chromatography on silica gel using ethyl acetate:methanol:0.88 ammonia (90:10:1) as eluant, to afford the title compounds.

| Ex No | Data |
|---|---|
| 396 | W=2-CF$_3$; $^1$H NMR(400MHz, CDCl$_3$): δ 1.61-1.76(m, 1H), 1.79-1.98(m, 3H), 2.62-2.80(m, 1H), 2.84-2.97(m, 2H), 3.42(m, 1H), 4.60(m, 1H), 5.62(d, 2H), 6.99(m, 2H), 7.20-7.55(m, 6H), 7.59(m, 1H), 7.66(m, 1H). LCMS: m/z APCl$^+$ 516[MH]$^+$ |
| 397 | W=3-CF$_3$; $^1$H NMR(400MHz, CDCl$_3$): δ 1.80(m, 2H), 1.98(m, 2H), 2.70(m, 1H), 2.88-3.02(m, 2H), 3.72(m, 1H), 4.57(m, 1H), 5.62(s, 2H), 7.00(m, 2H), 7.22(d, 2H), 7.25-7.59(m, 4H), 7.65(m, 2H). LCMS: m/z APCl$^+$ 516[MH]$^+$ |
| 398 | W=4-CF$_3$; $^1$H NMR(400MHz, CD$_3$OD): δ 1.78-1.96(m, 4H), 2.82(m, 2H), 3.00-3.14(m, 1H), 3.62(m, 1H), 4.58(m, 1H), 5.67(s, 2H), 7.22(m, 2H), 7.50(d, 2H), 7.58(m, 4H), 7.77(d, 2H). LCMS: m/z APCl$^+$ 516[MH]$^+$ |

-continued

| Ex No | Data |
|---|---|
| 399[A] | W=2-F, 5-Cl;<br>$^1$H NMR(400MHz, CDCl$_3$): δ 1.78-2.00(m, 4H), 2.70(m, 1H), 2.91(m, 1H), 3.01(m, 1H), 3.62(m, 1H), 4.58(m, 1H), 5.63(s, 2H), 7.01(m, 3H), 7.30(m, 2H), 7.42(d, 2H), 7.50(s, 2H). LCMS: m/z APCl$^+$ 500[MH]$^+$ |
| 400[B] | W=3-F<br>$^1$H NMR(400MHz, CDCl$_3$): δ 1.66-1.81(m, 2H), 1.98(m, 2H), 2.66(m, 1H), 2.80-2.96(m, 2H), 3.74-3.82(m, 1H), 4.45-4.60(m, 1H), 5.62(s, 2H), 6.99-7.12(m, 4H), 7.15(s, 1H), 7.37(m, 1H), 7.42(d, 2H), 7.49(s, 2H). LCMS: m/z APCl$^+$ 466[MH]$^+$ |
| 401[B] | W=2,3-di-F<br>$^1$H NMR(400MHz, CDCl$_3$): δ 1.74-2.00(m, 4H), 2.72(m, 1H), 2.79(m, 1H), 3.01(m, 1H), 3.62(m, 1H), 4.60(m, 1H), 5.62(s, 2H), 7.01(m, 2H), 7.07-7.21(m, 3H), 7.42(d, 2H), 7.52(s, 2H). LCMS: m/z APCl$^+$ 484[MH]$^+$ |
| 402[B] | W=2-F, 3-Cl<br>$^1$H NMR(400MHz, CDCl$_3$): δ 1.62-2.00(m, 4H), 2.70(m, 1H), 2.82-3.06(m, 2H), 3.60(m, 1H), 4.60(m, 1H), 5.62(s, 2H), 7.00(m, 2H), 7.15(m, 1H), 7.24(m, 1H), 7.41(m, 3H), 7.45(s, 2H). LCMS: m/z APCl$^+$ 500[MH]$^+$ |
| 403[B] | W=4-F, 3-Cl;<br>$^1$H NMR(400MHz, CDCl$_3$): δ 1.74-1.85(m, 2H), 1.98(m, 2H), 2.70(m, 1H), 2.82-2.98(m, 2H), 3.70-3.88(m, 1H), 4.40-4.58(m, 1H), 5.63(s, 2H), 7.02(m, 2H), 7.17(m, 1H), 7.23(m, 1H), 7.42(m, 3H), 7.49(s, 2H). LCMS: m/z APCl$^+$ 500[MH]$^+$ |

[A] = 2.5 eq. of triethylamine were used instead of polymer supported N-ethyl diisopropylamine.
[B] = 2 eq. of N-methyl morpholine used instead of polymer supported N-ethyl diisopropylamine.

EXAMPLES 404 TO 405

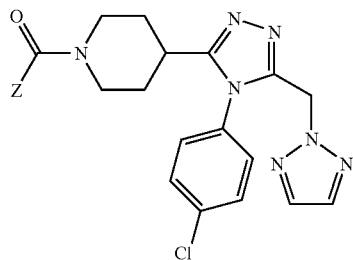

A solution of the appropriate acid, ZCO$_2$H (1.2 eq.), O-benzotriazol-1-yl-N,N,N',N'-tetramethyluronium hexafluorophosphate (1.2 eq.), N-methylmorpholine (1.4 eq.) and the amine from preparation 12a (1 eq.) in dichloromethane (7-10 mlmmol$^{-1}$) was stirred at room temperature for 24 hours. The reaction was partitioned between sodium hydroxide solution and dichloromethane, and the layers were then separated. The organic solution was washed with ammonium chloride solution, dried over MgSO$_4$ and evaporated under reduced pressure. The crude product was purified by column chromatography on silica gel using an elution gradient of dichloromethane:methanol:0.88 ammonia (100:0:0 to 90:10:1) to afford the title compounds.

| Ex No | Data |
|---|---|
| 404 | Z=3-fluoro-5-chlorophenyl;<br>$^1$H NMR(400MHz, CDCl$_3$): δ 1.80(m, 2H), 1.98(m, 2H), 2.70(m, 1H), 2.95(m, 2H), 3.78(m, 1H), 4.48(m, 1H), 5.63(s, 2H), 6.99(m, 3H), 7.15(m, 2H), 7.42(d, 2H), 7.50(s, 2H). LCMS: m/z APCl$^+$ 500[M]$^+$ |
| 405 | Z=indazol-3-yl;<br>$^1$H NMR(400MHz, DMSO-d$_6$): δ 1.63-1.82(m, 4H), 2.78-2.90(m, 2H), 3.18(m, 1H), 4.45(m, 1H), 4.62(m, 1H), 5.77(s, 1H), 7.18(m, 1H), 7.32-7.40(m, 3H), 7.58(m, 3H), 7.63(s, 2H), 7.90(d, 1H). LCMS: m/z ES$^-$ 486[M-H]$^-$ |

All of the compounds exemplified above showed a Ki value of less than 500 nM when tested in screen 1.0 (V$_{1A}$ filter binding assay) as described above.

Examples of specific compounds are illustrated below:

| Example No. | Ki (nM) |
|---|---|
| 165 | 2.98 |
| 206 | 2.43 |
| 399 | 1.99 |
| 405 | 1.11 |

The invention claimed is:
1. A compound of formula (I),

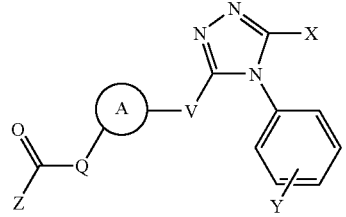

or a pharmaceutically acceptable salt thereof, wherein:
X is —[CH$_2$]$_a$—R or —[CH$_2$]$_a$—O—[CH$_2$]$_b$—R;
a is 1;
b is a number selected from 0 to 4;
R is H, CF$_3$ or Het;
Het is imidazolyl or triazolyl;
Y is one to three substituents independently selected from H, halo, CN, C$_{1-6}$ alkyl, C$_{1-6}$ alkoxy, wherein said C$_{1-6}$ alkyl is unbranched and is optionally substituted on its terminal carbon atom with one to three fluoro or one pyrrolidinyl and wherein said C$_{1-6}$ alkoxy is unbranched and is optionally substituted on its terminal carbon atom with one to three fluoro;
V is a direct bond;
Ring A is a piperidine ring, wherein said piperidine ring is optionally substituted with one to three groups selected from C$_{1-6}$ alkyl, phenyl or hydroxy;
Q is a direct bond;
Z is selected from the group consisting of phenyl, pyridyl, quinolinyl, isoquinolinyl, naphthyl, benzoimidazolyl, benzotriazolyl, oxadiazolyl, indazolyl and indolyl, each optionally substituted with one to three groups selected from W;
W independently at each occurrence is halo, hydroxy, CN, C$_{1-6}$ alkyl, C$_{1-6}$ alkoxy, C$_{1-6}$ alkylSO$_2$, C$_{1-6}$ alkylSO, C$_{1-6}$ alkylS, C$_{3-6}$ cycloalkoxy, C$_{3-6}$ cycloalkyl, phenyl, phenoxy, pyridinyl, pyrimidinyl, benzyl, benzyloxy or H₂NSO₂, wherein said $C_{1-6}$ alkyl or said $C_{1-6}$ alkoxy are each unbranched and are each optionally substituted on the terminal carbon atom with one to three fluoro.

2. The compound according to claim 1, wherein X is —[CH₂]$_a$—R or a pharmaceutically acceptable salt thereof.

3. The compound according to claim 2, wherein R is Het, or a pharmaceutically acceptable salt thereof.

4. The compound according to claim 1, wherein Y is halo, or a pharmaceutically acceptable salt thereof.

5. The compound according to claim 4, wherein Y is chloro, or a pharmaceutically acceptable salt thereof.

6. The compound according to claim 5, wherein Y is 4-chloro, or a pharmaceutically acceptable salt thereof.

7. The compound according to claim 1, wherein Z is phenyl optionally substituted with one to three groups independently selected from W, or a pharmaceutically acceptable salt thereof.

8. The compound according to claim 1, wherein Z is substituted with halo, or a pharmaceutically acceptable salt thereof.

9. The compound according to claim 1 selected from (3-Chloro-phenyl)-{4-[4-(4-chloro-phenyl)-5-[1,2,3]triazol-2-ylmethyl-4H-[1,2,4]triazol-3-yl]-piperidin-1-yl}-methanone;

(4-Chloro-phenyl)-{4-[4-(4-chloro-phenyl)-5-[1,2,3]triazol-2-ylmethyl-4H-[1,2,4]triazol-3-yl]-piperidin-1-yl}-methanone;

(5-Chloro-2-fluoro-phenyl)-{4-[4-(4-chloro-phenyl)-5-[1,2,3]triazol-2-ylmethyl-4H-[1,2,4]triazol-3-yl]-piperidin-1-yl}-methanone;

{4-[4-(4-Chloro-phenyl)-5-[1,2,3]triazol-2-ylmethyl-4H-[1,2,4]triazol-3-yl]-piperidin-1-yl}-(3,5-difluoro-phenyl)-methanone;

{4-[4-(4-Chloro-phenyl)-5-[1,2,3]triazol-2-ylmethyl-4H-[1,2,4]triazol-3-yl]-piperidin-1-yl}-(3-fluoro-phenyl)-methanone;

{4-[4-(4-Chloro-phenyl)-5-[1,2,3]triazol-2-ylmethyl-4H-[1,2,4]triazol-3-yl]-piperidin-1-yl}-(2,3-difluoro-phenyl)-methanone;

(3-Chloro-2-fluoro-phenyl)-{4-[4-(4-chloro-phenyl)-5-[1,2,3]triazol-2-ylmethyl-4H-[1,2,4]triazol-3-yl]-piperidin-1-yl}-methanone;

(3-Chloro-4-fluoro-phenyl)-{4-[4-(4-chloro-phenyl)-5-[1,2,3]triazol-2-ylmethyl-4H-[1,2,4]triazol-3-yl]-piperidin-1-yl}-methanone;

{4-[4-(4-Chloro-phenyl)-5-[1,2,3]triazol-2-ylmethyl-4H-[1,2,4]triazol-3-yl]-piperidin-1-yl}-(4-trifluoromethyl-phenyl)-methanone;

{4-[4-(4-Chloro-phenyl)-5-[1,2,3]triazol-2-ylmethyl-4H-[1,2,4]triazol-3-yl]-piperidin-1-yl}-(3-trifluoromethyl-phenyl)-methanone;

{4-[4-(4-Chloro-phenyl)-5-[1,2,3]triazol-2-ylmethyl-4H-[1,2,4]triazol-3-yl]-piperidin-1-yl}-(2-trifluoromethyl-phenyl)-methanone;

(3-Chloro-5-fluoro-phenyl)-{4-[4-(4-chloro-phenyl)-5-[1,2,3]triazol-2-ylmethyl-4H-[1,2,4]triazol-3-yl]-piperidin-1-yl}-methanone;

{4-[4-(4-Chloro-phenyl)-5-[1,2,3]triazol-2-ylmethyl-4H-[1,2,4]triazol-3-yl]-piperidin-1-yl}-(4-difluoromethyl-phenyl)-methanone;

{4-[4-(4-Chloro-phenyl)-5-[1,2,3]triazol-2-ylmethyl-4H-[1,2,4]triazol-3-yl]-piperidin-1-yl}-(1H-indazol-3-yl)-methanone;

or a pharmaceutically acceptable salt thereof.

10. {4-[4-(4-Chloro-phenyl)-5-[1,2,3]triazol-2-ylmethyl-4H-[1,2,4]triazol-3-yl]-piperidin-1-yl}-(3,5-difluoro-phenyl)-methanone, or a pharmaceutically acceptable salt thereof.

11. A method of treating cardiovascular disease, primary dysmenorrhea, secondary dysmenorrhea, premature labor or Raynaud's disease comprising administering a therapeutically effective amount of a compound, or a pharmaceutically acceptable salt thereof, according to claim 1.

12. The method according to claim 11, wherein primary dysmenorrhea or secondary dysmenorrhea is treated.

13. A pharmaceutical composition comprising a compound according to claim 1, or a pharmaceutically acceptable salt thereof, and a pharmaceutically acceptable excipient, diluent or carrier.

14. The pharmaceutical composition according to claim 13 wherein the compound is {4-[4-(4-Chloro-phenyl)-5-[1,2,3]triazol-2-ylmethyl-4H-[1,2,4]triazol-3-yl]-piperidin-1-yl}-(3,5-difluoro-phenyl)-methanone, or a pharmaceutically acceptable salt thereof.

15. The method according to claim 11 wherein the compound is {4-[4-(4-Chloro-phenyl)-5-[1,2,3]triazol-2-ylmethyl-4H-[1,2,4]triazol-3-yl]-piperidin-1-yl}-(3,5-difluoro-phenyl)-methanone, or a pharmaceutically acceptable salt thereof.

* * * * *